(12) United States Patent
Yedgar et al.

(10) Patent No.: US 7,034,006 B2
(45) Date of Patent: Apr. 25, 2006

(54) USE OF LIPID CONJUGATES IN THE TREATMENT OF DISEASE

(75) Inventors: Saul Yedgar, Jerusalem (IL); David Shuseyov, Carmei Yossef (IL); Gershon Golomb, Efrat (IL); Reuven Reich, Rehovot (IL); Isaac Ginsburg, Jerusalem (IL); Abd-al-Roof Higazi, Shimshon (IL); Moshe Ligumski, Jerusalem (IL); Miron Krimsky, Jerusalem (IL); David Ojcius, Vincennes (FR); Benito Antonio Yard, Freinsheim (DE); Fokko Johannes van der Woude, Hirschberg-Leutershausen (DE); Edit Schnitzer, Tel Aviv (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 433 days.

(21) Appl. No.: 09/756,765

(22) Filed: Jan. 10, 2001

(65) Prior Publication Data

US 2002/0049183 A1 Apr. 25, 2002

Related U.S. Application Data

(60) Provisional application No. 60/174,907, filed on Jan. 10, 2000, and provisional application No. 60/174,905, filed on Jan. 10, 2000.

(51) Int. Cl.
*A61K 31/70* (2006.01)
*A61K 31/715* (2006.01)
*C08B 37/08* (2006.01)
*C08B 37/10* (2006.01)
*C07H 5/06* (2006.01)

(52) U.S. Cl. .............................. 514/42; 514/53; 514/54; 514/56; 514/61; 514/62; 536/18.7; 536/20; 536/21; 536/22.1; 536/29.1; 536/29.13; 536/123.1; 536/123.13

(58) Field of Classification Search .................. 514/42, 514/54, 53, 56, 61, 62; 536/123.1, 29.13, 536/18.7, 20, 21, 22.1, 29.1
See application file for complete search history.

(56) References Cited

U.S. PATENT DOCUMENTS

| | | | | |
|---|---|---|---|---|
| 5,064,817 A | | 11/1991 | Yedgar et al. ................. | 514/78 |
| 6,162,787 A | * | 12/2000 | Sorgente et al. ............... | 514/2 |
| 6,171,614 B1 | * | 1/2001 | Chaikof et al. ............. | 424/450 |

OTHER PUBLICATIONS

Group V Phospholipase $A_2$–mediated Oletic Acid Mobilization in Lipopolysaccharide–stimulated P388D$_1$ Macrophages; Balsinde Jesus, Balboa Maria A., Yedgar Saul, and Dennis Edward A., The Journal of Biological Chemistry, vol. 275, Feb. 18 pp4783–4786.

Inhibition of LPS–induced chemokine production in human lund endothelial cells by lipid conjugates achored to the membrane Beck, G. Ch, Yard B.A. Schulte J., Oberacker. R, Van Ackern K, Van Der Woude F.J, Krimsky M, Kaszkin M and Yedgar Y.; British Journal of Pharmacology (2002) 135, 1665–1674. Control of capillary formation by membrane-–anchored extracellular Inhibitor of phospholipase $A_2$; Chem, W.M,
Soria J, Coria C, Krimsky M and Yedgar S.; FEBS 26215 letters 522 (2002) 113–118.
Interaction of hyacluronic acid–linked phophatidylethonolmine (HyPE) with LDL and its effect on the susceptibility of LDL lips to oxidation; Schnitzer Edit, Dagan Arie, Krimsky Miron, Lichtenberg Dov, Pinchuk Ilya, Shinar Hadassa, Yedgar Saul; CPL 104 (2000) 149–160.
Inhibition of phopholipase A2 as a therapeutic target; Yedgar Saul, Lichtenberg Dov, Schnitzer Edit, BBA Biochimica et Biophyscia Acta 1488 (2000) 182–187.
Modulation of IFN–GAMMA–induced immunogenicity by phosphatidylethanolamine–linked hyaluronic acid; Yard Benito A., Yedgar Saul, Scheele Martin, Van Der Woulde Diane, Beck Grietje, Heidrich Barbel, Krimsky Miron,. Van Der Woulde Fokko J, and Post Stefan TRANSPLANTATION vol. 73, 984–992, No. 6, Mar. 27, 2002.

* cited by examiner

*Primary Examiner*—Peter O'Sullivan
(74) *Attorney, Agent, or Firm*—Eitan, Pearl, Latzer & Cohen Zedek, LLP; Mark S. Cohen

(57) ABSTRACT

The invention provides novel methods for treating disease based upon the medicinal use of lipids and phospholipids covalently bound to physiologically acceptable monomers or polymers. Phosphatidylethanolamine moieties conjugated to physiologically acceptable monomers and polymers (PE conjugates) manifest an unexpectedly wide range of pharmacological effects, including stabilizing cell membranes; limiting oxidative damage to cell and blood components; limiting cell proliferation, cell extravasation and (tumor) cell migratory behavior; suppressing immune responses; and attenuating physiological reactions to stress, as expressed in elevated chemokine levels. The surprisingly manifold pharmacological properties of the PL-conjugates allow for the invention, disclosed herein, of novel methods for the treatment of a diverse range of disease states, including obstructive respiratory disease, including asthma; colitis and Crohn's disease; central nervous system insult, including blood brain barrier compromise, ischemic stroke, and multiple sclerosis; contact dermatitis; psoriasis; cardiovascular disease, including ischemic conditions and prophylaxis for invasive vascular procedures; cellular proliferative disorders, including anti-tumor vasculogenesis, invasiveness, and metastases; anti-oxidant therapy; hemolytic syndromes; sepsis; acute respiratory distress syndrome; tissue transplant rejection syndromes; autoimmune disease; viral infection; and hypersensitivity conjunctivitis. The therapeutic methods of the invention include administration of phosphatidylethanolamine bound to carboxymethylcellulose, heparin, hyaluronic acid, polyethylene glycol, and hemaccel. Disclosed herein are also new compounds comprised of phospholipid moieties bound to low molecular weight monomers and dimers, including mono- and disaccharides, carboxylated disaccharides, mono- and dicarboxylic acids, salicylates, bile acids, and fatty acids.

5 Claims, 55 Drawing Sheets

A

B

Each datum is Mean+SEM for 9 mice.
* $p < 0.001$;  $p < 0.005$; * $p < 0.01$; # not significant.

A. control
B. LPS
C. HYPE-40 10 μM
D. HYPE-40 20 μM
E. HYPE-80 10 μM
F. HYPE-80 20 μM Legend
A - Basal, serum defficient DMEM
B - Control, thrombin
C - Thrombin, no wash-out, and after 6 hours add 50μM HYPE
D - Thrombin+50μM HYPE
E - Thrombin,6 hours, then wash-out of thrombin, further incubation with DMEM
F - Thrombin, 6 hours, wash-out of thrombin, add 50μM HYPE
G - Thrombin, 6 hours ,then harvest and counting
H - DMEM+10% fetal calf serum 1, medium alone

2, LPS

3, LPS + HyPE

NF-kB →

PROSTAGLANDIN $E_2$ AND LEUKOTRIENE $B_4$ LEVELS IN
THE CORNEA OF GUINEA PIGS WITH ALLERGIC CONJUNCTIVITIS

USE OF LIPID CONJUGATES IN THE TREATMENT OF DISEASE

CROSS-REFERENCE TO RELATED APPLICATIONS

This application claims priority from a Provisional Application U.S. Ser. No. 60/174,907, filed Jan. 10, 2000, which is hereby incorporated by reference.

FIELD OF THE INVENTION

The present invention provides administrating a class of pharmaceutically active lipid conjugate compounds directed to treating disease, including obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, chlamydia infection, and hypersensitivity conjunctivitis.

BACKGROUND OF THE INVENTION

Some high molecular weight conjugates have been described in U.S. Pat. No. 5,064,817, and in the publications referenced herein, in particular wherein the conjugated moiety is dodecandioic, dextrane, dextranamide, carboxymethylcellulose, carboxymethylcellulose-acyl, poly-D-glutamic acid, polyacrylic acid, polyethylene glycol, hydroxyethyl starch, heparin, hyaluronic acid, and polygleatin ('hemacell'), but these compounds were not known to be of wide-spectrum pharmacological effectiveness. These compounds are known to have the pharmacological activity of inhibiting the enzyme phospholipase $A_2$ ($PLA_2$, EC 3.1.1.4), which catalyzes the breakdown of phospholipids at the sn-2 position to produce a fatty acid and a lysophospholipid. The activity of this enzyme has been correlated with various cell functions, particularly with secretory processes such as exocytosis and eicosanoid production (prostaglandins, thromboxanes and leukotrienes). The biological activity ascribed to these mostly phospholipid derivatives was limited to inhibition of platelet aggregation, thromboxane secretion, and selective inhibition of phospholipase $A_2$. Accordingly, the use of $PLA_2$-inhibitors was proposed for treatment of diseases which are associated with enhanced cellular secretions, such as in allergy and inflammation. Thus phosphatidylethanolamine-conjugates (PE-conjugates) of high molecular weight, and related phospholipid conjugate compounds (PL-conjugates), were judged to be useful in the treatment of $PLA_2$-related conditions, particularly since their relatively high molecular size renders them useful as selective inhibitors of this hydrolase enzyme activity at the level of the cell membrane. Thus the presumed medical use of these compounds was necessarily limited to the treatment of $PLA_2$-related pathological conditions. Since their inception, the PL-conjugates have been subjected to intensive laboratory investigation directed towards establishing new methods of treating common but severe diseases which, being of multifactorial origins, continue to account for considerable morbidity and mortality worldwide. From these studies there has emerged for the PL-conjugates a wide spectrum of potent and useful biological action and which, in terms of the treatment of specific disease, the role of these compounds has not heretofore been introduced to the medical art.

SUMMARY OF THE INVENTION

This invention provides lipid conjugates, primarily comprised from phospholipids, such as phosphatidylethanolamine, and related phospholipids, such as phosphatidylserine, which when appropriately prepared by conjugation to a physiologically compatible monomer, dimer, oligomer or polymeric moiety, display an unexpected wide range and potency of pharmacological activities. Administration of these compounds comprises effective treatment of a subject afflicted with disease including obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, chlamydia infection, and hypersensitivity conjunctivitis. For these diseases, use of the PL-conjugates as pharmacological therapy represents a new class of drugs, conferring benefit to many patients who currently continue to suffer from their affliction despite rigorous compliance to the conventional regimens prescribed by their physicians.

In one embodiment of the invention, a PL-conjugate is administered as an anti-tumor necrosis factor (TNF) agent to a subject in suffering from dysregulation of this cytokine.

In another embodiment, a PL-conjugate is administered as an anti-proliferative agent of smooth muscle proliferation and as an anti-angiogenesis agent, to a subject suffering from dysregulation of smooth muscle growth or angiogenesis, as may occur in vascular disease or metastatic cancer growths.

In another embodiment, a PL-conjugate is administered as an anti-spasmic, anti-cytokine, immunosuppressive, and anti-infiltrative agent to a subject afflicted with obstructive respiratory disease, including asthma and chronic obstructive pulmonary disease.

In another embodiment, PL-conjugate is administered as a cytoprotective, anti-cytokine and immunosupppressive agent to a subject afflicted with colitis or Crohn's disease.

In another embodiment, a PL-conjugate is administered as an anti-nitric oxide, anti-dopamine, anti-oxidant, anti-cytokine, and blood brain barrier stabilizing neuroprotective agent to a subject afflicted with an acute or degenerative brain insult, including ischemic stroke, tumor, trauma, infection, hyperdomainergic states, schizophrenia, Huntington's chorea, and multiple sclerosis.

In another embodiment, PL-conjugate is administered as an immunosuppressive, anti-proliferative, anti-cytokine, blood brain barrier stabilizing and neuroprotective agent to a subject afflicted with multiple sclerosis.

In another embodiment, a PL-conjugate is administered as an immunosuppressive and anti-cytokine agent to a subject afflicted with a cutaneous hypersensitivity reaction, including contact dermatitis.

In another embodiment, a PL-conjugate is administered as an anti-proliferative and anti-cytokine agent to a subject afflicted with psoriasis.

In another embodiment, a PL-conjugate is administered as an anti-proliferative, anti-oxidant, anti-migratory, and anti-atherogenesis agent, to a subject afflicted with cardiovascular disease, including acute or chronic ischemic vascular disease, diffuse atherosclerotic lesions, and reperfusion injury associated with ischemic events.

In another embodiment, a PL-conjugate is administered as an anti-stenosis agent to a subject undergoing an invasive medical procedure, in particular arterial or venous catheterization.

In another embodiment, a PL-conjugate is administered as anti-proliferative, anti-vasculogenesis, anti-cytokine, anticell matrix degradation, and anti-migratory agent to a subject afflicted with an invasive cellular proliferative disorder, including metastatic or pre-metastatic cancer.

In another embodiment, a PL-conjugate is administered as an anti-oxidant agent to a subject as prophylaxis from oxidative tissue damage, including the damage associated with physiological stress, irradiation, and aging.

In another embodiment, a PL-conjugate is administered as membrane-stabilizing and anti-oxidant agent to a subject afflicted with hemolysis, including hemolytic anemia of toxic, infectious, or genetic origin.

In another embodiment, a PL-conjugate is administered as an anti-chemokine, anti-cytokine agent, and anti-nitric oxide agent to a subject afflicted with septicemia.

In another embodiment, a PL-conjugate is administered as an anti-chemokine and anti-spasmodic agent to a subject afflicted with acute respiratory distress syndrome.

In another embodiment, a PL-conjugate is administered as an immunosuppressive, cytoprotective, anti-cytokine and anti-reperfusion injury agent to a subject undergoing tissue or organ transplantation.

In another embodiment, a PL-conjugate is administered as an immunosuppressive, anti-cytokine and anti-proliferative agent to a subject afflicted with autoimmune disease.

In another embodiment, a PL-conjugate is administered as an anti-viral therapy to a subject afflicted with a viral infection, including the retrovirus known as HIV.

In another embodiment, a PL-conjugate is administered as an anti-cytokine agent to a subject afflicted with hypersensitivity conjunctivitis.

In another embodiment, a PL-conjugate is added as a preservative to a tissue or organ removed from the body for the purpose of storage or transplantation.

In another embodiment, a PL-conjugate is administered as a therapeutic agent to a subject afflicted with chlamydia infection.

The route of administration and dosage of the PL-conjugate administered can be easily determined by a skilled clinician depending upon the nature of the disease and the medical state of the patient being treated. In some cases, more than one type of PL-conjugate will be administered, through one or more different routes of administration, as either prophylaxis to a subject at risk or in response to the appearance of the signs and symptoms of the disease. The use of PL-conjugates in the treatment of disease does not preclude additional modes of therapy, and it may be expected that concomitant administration of a PL-conjugate may allow for additional modifications, for example, a reduction in the dosage of the other medications prescribed.

In another aspect of the invention, new compounds are provided, representing low molecular weight PL-conjugates, in particular phospholipids bound through their polar head group to a mono- or disaccharide, a carboxydisaccharide, a mono- or dicarboxylic acid, a salicylate, an amino acid, a dipeptide, an oligopeptide, a bile acid, a fatty acid, cholesterylhemisuccinate, a trisaccharide, or a di- or trisaccharide unit monomer of a polyglycosaminoglycan, including repeating units of heparin, heparan sulfate, hyaluronic acid, dextran, chondroitin, chondroitin-4-sulfate, chondroitin-6-sulfate, keratin, keratan sulfate, dermatin, and dermatan sulfate. These new compounds, as representative of the class of PL-conjugates of low molecular weight, exhibit the same wide range and potency of pharmaceutical activities manifested by the higher molecular weight PL-conjugates described herein. Introduction of these novel compounds here expands the range of useful PL-conjugates as novel therapeutic drugs in the treatment of specific diseases.

In another embodiment of the invention, phosphatidylserine may be employed as an alternative to phosphatidylethanolamine in preparation and use of therapeutic compounds, wherein the phospholipid is bound through the polar head group to a physiologically acceptable monomer or polymer.

In another embodiment of the invention, phosphatidylcholine, phosphatidylinositol, phosphatidylglycerol, and related polar phospholipids may be employed as an alternative to phosphatidylethanolamine in preparation and use of therapeutic compounds, wherein the phospholipid is bound through the polar head group to a physiologically acceptable monomer or polymer. When acylglycerols are used, such as monoacylglycerol, diacylglycerol, and triacylglycerol, the polar head group is a hydroxyl group. Other lipids which enable the methods of the invention are sphingomyelin, sphingosine, and ceramide.

In another embodiment of the invention, phospholipid derivatives bearing ether or alkyl bonds instead of ester bonds at the C1 and C2 positions of the glycerol backbone of the phospholipid may be used as the therapeutic phospholipid-conjugate compound.

In another aspect of the invention, the PL-conjugates described herein are used in a process for manufacture of a pharmaceutical composition for treating a subject afflicted with obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, chlamydia infection, or hypersensitivity conjunctivitis.

In another embodiment, the PL-conjugates described herein are used in a process for manufacture of a pharmaceutical composition for preserving a tissue or organ removed from the body for the purpose of storage or transplantation.

Based on the nature of the present disclosure, wherein many diseases traditionally considered to be unrelated in etiology and epidemiology may now be amenable to drug therapy with PL-conjugates, it is reasonable to anticipate that further experimentation will lead to a more extensive scope of the invention, allowing for additional medicinal modalities based upon treatment of biological tissues and living subjects with PL-conjugates.

DETAILED DESCRIPTION OF THE INVENTION

Figure 1:
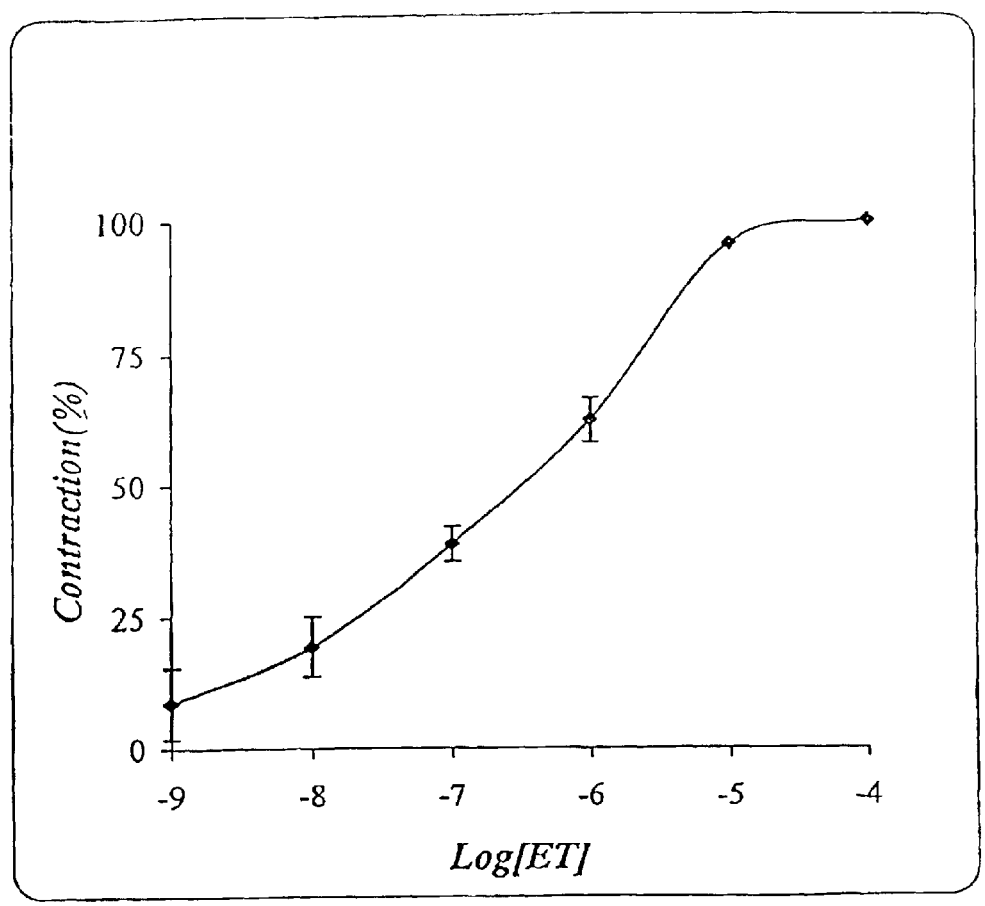
FIG. 1. Tracheal Contraction Assay

The invention provides PL-conjugates which display a wide-range and unusual combination of cytoprotective pharmacological activities. These compounds can alleviate airway obstruction in asthma, protect mucosal tissue in gastrointestinal disease, suppress immune responses, alleviate cutaneous hypersensitivity reactions, inhibit cell proliferation associated with vascular injury and immunological responses, inhibit cell migration associated with vascular and central nervous system disease, attenuate oxidative damage to tissue proteins and cell membranes, interfere with viral spread, reduce tissue destroying enzyme activity, and reduce intracellular levels of chemokines and cytokines. Thus these compounds are useful in the treatment of a diversity of disease states, including obstructive respiratory disease, colitis, Crohn's disease, central nervous system insult, multiple sclerosis, contact dermatitis, psoriasis, cardiovascular disease, invasive medical procedures, invasive cellular proliferative disorders, anti-oxidant therapy, hemolytic syndromes, sepsis, acute respiratory distress syndrome, tissue transplant rejection syndromes, autoimmune disease, viral infection, and hypersensitivity conjunctivitis.

Obstructive respiratory disease is a disease of luminal passages in the lungs, marked by dyspnea, tachypnea, or ausculatory or radiological signs of airway obstruction. While asthma is a prototypical disorder for obstructive respiratory disease, this condition is encountered clinically also in acute pulmonary infections, acute respiratory distress syndrome, and as chronic obstructive pulmonary disease. The pathophysiology is attributed to obstruction of air flow due to constriction of airway lumen smooth muscle and accumulation of infiltrates in and around the airway lumen.

Colitis is a chronic disease of the gastrointestinal lumen, marked by abdominal discomfort, diarrhea and, upon radiological or histological diagnosis, characteristic signs of mucosal damage including epithelial denudation. Crohn's disease is a related disorder affecting typically the small intestine but which may involve any region of the gastrointestinal tract.

Multiple sclerosis is a disease of white matter, marked by motor weakness or sensory disturbance, or both, usually diagnosed by spinal fluid analysis or magnetic resonance imaging. Visual disturbance, including blindness, is common as well. In regions of disease activity, the blood brain barrier is impaired.

Skin hypersensitivity reactions, otherwise known as contact dermatitis, are marked by external signs of tissue irritation such as localized redness, swelling, and pruritis. Virtually any substance may produce the condition, and it is one of the most common complaints diagnosed by dermatologists.

Psoriasis is also one of the most common dermatologic diseases, affecting 1 to 2 percent of people. The most common areas of involvement are the elbows, knees, gluteal cleft, and the scalp. In active lesions of psoriasis, the rate of epidermal cell replications is accelerated. Long-term use of topical glucocorticoids is often accompanied by loss of effectiveness.

Cardiovascular disease refers to both disorders of blood vessel lumen narrowing as well as to resultant ischemic syndromes of the target organs they supply, such as heart, kidney, and brain. Ischemia, or reduced of blood supply, results from the narrowing of a blood vessel. The signs and symptoms of cardiovascular disease include, among others, angina pectoris, weakness, dyspnea, transient ischemic attacks, stroke, and renal insufficiency. Diagnosis is based on clinical grounds in conjunction with ancilliary diagnostic tests, such as blood tests, electrocardiograms, echography, and angiography. Atherosclerosis is a common element in cardiovasular disease in which narrowing of the blood vessel lumen is due to scar-like plaques formed from reactive, migrating, and proliferating cells and from local incorporation of blood fat, cholesterol, and lipoprotein. Of particular significance in this respect is the accumulation of low density lipoprotein (LDL), which may be accelerated when damaged by oxidation. Plaques are considered to be the sites for both acute and chronic stenotic lesions, wherein the risk of tissue ischemia rises.

Stenotic or narrowing lesions of blood vessels occur not only in atherosclerosis but in other systemic cardiovascular disorders as well. Among these are arterial hypertension, vasculitides, including the vasculitis associated with transplanted organs, and coagulative disorders. Many of these disorders, particularly hypertension, atherosclerosis, and vasculitis occur concommitantly in the same patient.

Reperfusion injury refers to the tissue injury and initiation of necrosis following the resumption of blood flow to a previously ischemic tissue. This phenomenon is recognized as an important component of ischemic and post-ischemic types of injury, particularly to brain and heart tissue. One pathophysiological mechanism which predominates in reperfusion is the damaging effect of reactive oxygen species, otherwise known as oxidative damage or free radial injury. Nitric oxide and its radicals are also implicated in the pathophysiology. The production of these noxious chemical species is attributed to the local accumulation, adhesion, and transmigration of leukocytes at the lesion site.

Invasive medical procedures, such as catheterization of arteries or veins or open surgery are frequently associated with tissue ischemia due to blood vessel injury as well as to reperfusion injury, both of which may arise in the course of an invasive procedure. Thus preservation of blood vessel patency and prevention of reperfusion injury are the subject of intense investigation in medical science. Such procedures are performed for both diagnostic and therapeutic purposes, and adjuvant drugs are commonly prescribed to prevent complications of blood vessel injury or restenosis. Formation of these lesions involves a multiplicity of participants, including coagulative elements of the blood, blood cells, and the structural elements and cells of the blood vessel lumen wall. For example, arterial restenosis appearing after successful balloon angioplasty is frequently due to the narrowing of the inner diameter of the artery by the growth (proliferation) of smooth muscle cells in the areas of irritation caused by the balloon angioplasty. This new stenotic lesion may be comprised from other cell types as well, including leukocytes, accumulating at the lesion site through processes of migration and local proliferation. The two events (cell migration and proliferation) are almost certainly due to the coordinated interaction of a number of different cytokines likely released by early accumulation of macrophages at the site of original tissue injury. Thus leukocytes contribute to stenotic lesion formation through the processes of migration, local proliferation, passage through endothelial barriers, accumulation of cholesterol-rich lipoprotein, conversion to foam cells, and secretion of cytokines. This proliferation of cells and narrowing of the vascular lumen is not however restricted or limited to the coronary arteries or cerebral circulation. It can also occur post-operatively causing restenosis in, for example, peripheral vascular systems.

In the context of the present invention, the term cardiovascular disease refers to blood vessel lumen narrowing arising in the course of atherosclerosis, vasculitis, invasive procedures, particularly catheterization of an artery or vein, and the ischemic syndromes associated with them.

Transplantation of tissue, grafts, and organs is frequently complicated by the appearance of host-versus-graft and graft-versus-host disease, both of which may occur acutely or chronically in the recipient of the graft. The source of the graft may be allogeneic (from the same species) or xenogeneic (from another species). Whether as complication due to the induced hyperactive immune response, or through another mechanism, vasculitis remains a frequently encountered complication of tissue transplantation procedures. Moreover, vascular damage due to reperfusion injury is considered to be a major factor in the post-surgical malfunctioning of tissue and organ transplants.

Autoimmune diseases are conditions in which the change in clinical state of the subject is attributed to aberrant cellular and/or humoral immune responses. The most common autoimmune diseases in the U.S. are juvenile diabetes, Hashimoto's and Grave's thryroiditis, rheumatoid arthritis, Crohn's disease and ulcerative colitis, chronic active hepatitis, vitaligo, glomerulonephritis, uveitis, multiple sclerosis, scleroderma, hemolytic anemia, idiopathic thrombocytopenic purpura, myasthenia gravis, systemic lupus erythematosis, and pemphigus.

Hyperproliferative cellular disorders, such as cancer cells arising at primary organ sites or at other loci of spread (metastases), are one of the leading causes of death in the U.S. Cancers are frequently highly resistant to all forms of treatment including therapy with potent anti-proliferative drugs and radiation. Increasingly the medical community is becoming aware of the critical role played by the vasculature associated with both the primary and metastatic forms of disease. Like any cell cluster, cancer cells are dependent upon a reliable blood supply and in fact, cancer cells are known to encourage the process of de novo vascularization through elaboration of growth factors which act on endothelial cells and smooth muscle cells to form new blood vessels, thus supplying the cancerous growth.

Metastasis, the spread of cancer cells to ectopic sites, is frequently a vasculature dependent process as well, often referred to as hematogenous spread. The physiological barrier imposed by the blood vessel wall, comprised from elements such as endothelial cells and basement membrane substance, is normally highly selective to the passage of cells. However, metastatic cells abrogate this barrier, employing a variety of mechanisms, some of which have been established in the scientific literature. For example, such abnormal cells produce hydrolytic enzymes which degrade the extracellular matrix and associated components of the vascular barrier, such as collagenase, heparinase, and hyaluronidase. Thus a critical factor in the metastatic process is the ability of cancer cells to intrude through or permeate the wall of the blood vessel lumen, thus arriving to invade a new tissue site after travel through the circulation. Cancer cells also elaborate messenger chemicals, known as cytokines and chemokines, which enable the metastatic process, from many aspects, including angiogenesis.

Cellular elaboration of cytokines and chemokines serve an important regulatory function in health; however, when a hyperactive response to stress or disease is triggered, these proteins may present in excess and damage tissue, thereby pushing the disease state toward further deterioration. Two examples in which this occurs are systemic infection, in particular when due to blood born bacteria (septicemia), and in the pulmonary condition known as acute (or adult) respiratory distress syndrome (ARDS). In ARDS, lung spaces fill with fluid, impeding gas exchange and producing respiratory failure. Although platelet aggregation occurs, the major offenders appear to be monocytic phagocytes and leukocytes that adhere to endothelial surfaces and undergo a respiratory burst to inflict oxidant injury and release chemokines such as Gro α, ENA-78, CX3X and MCP-1, in addition to leukotrienes, thromboxanes, and prostaglandins. The monocytic phagocytes, mainly macrophages in the alveoli and those lining the vasculature, also release oxidants, mediators, and a series of degradative enzymes that directly damage endothelial cells and cause leukocytes to release their lysosomal enzymes. The mortality rate is over 50%. The most common causes of ARDS are infection, aspiration, smoke and toxin inhalation, as well as systemic processes initiated outside the lung, including bacterial septicemia. The sepsis syndrome and shock are triggered by the interactions of various microbial products in the blood, in particular, gram-negative endotoxins, with host mediator systems. The incidence is estimated to be up to 500,000 cases per year in the U.S. alone, a Fig. which is considered to rise due to the increasing prevalence of antibiotic resistant organisms. A variety of host mediators have been implicated in the pathogenesis of septicemia and septic shock (referred to collectively herein as sepsis) including factors released from stimulated cells, in particular, cytokines, tumor necrosis factor-α (TNF), Gro α,ENA-78, CX3X and MCP-1, NFκβ transcription factor, lysosomal enzymes and oxidants from leukocytes, and products of the metabolism of arachidonic acid, among others.

Red blood cell lysis, or hemolysis, may be an inherited or acquired disorder, giving rise to anemia, iron deficiency, or jaundice. Among the acquired syndromes are membrane anomalies due to direct toxic effects of snake bites or of infectious agents, including viral, bacterial and parasitic etiologies, particularly malaria; exposure to oxidizing substances through ingestion or disease; or as a result of mechanical trauma within abnormal blood vessels. This latter condition, known as microangiopathic hemolysis, is considered to be related in mechanism to the hemolysis produced from blood passage through prosthetic implants, such as heart valves. Inherited red blood cell membrane fragility often occurs due to intracorpuscular enzyme and structural defects, such as glucose 6-phosphatase deficiency, sickle cell anemia, and thalessemia. Red blood cell lysis is one of the limiting factors in the storage life of blood products, particularly when subjected to free-radical forming photodynamic virocidal treatments, such as γ-irradiation.

The acquired immunodeficiency syndrome is considered to be a rapidly growing global epidemic and one route of spread is through contaminated blood products. Transmission and progression of this disease is dependent upon the infective activity of the human immunodeficiency virus. Current therapies are limited primarily to the administration of reverse transcriptase inhibitors, drugs of high expense and low patient tolerability.

Oxidative injury refers to the effect of peroxidation and free radical production on body tissues. To some extent, peroxide production is a normal, physiological process, attributed, for example, a role in immune defense. However, in stress and disease states, or over the natural course of time, as in physiological senescence, the accumulative addition of these unstable chemical moieties to tissue structures, including membrane components and blood proteins, leads to an irreversible pattern of injury. Agents that act as anti-oxidants can protect against oxidative damage. Such protection has been the subject of numerous scientific publications.

Intracellular bacterial parasites are one of the most prevelant forms of sexually transmitted disease and are frequently intractable to conventional antibiotic therapy. Vaginal infection with chlamydia species are a salient example.

The present invention offers methods for the treatment of disease based upon administration of phospholipids covalently conjugated through their polar head group to a physiologically acceptable chemical moiety which may be of high or low molecular weight.

The phospholipid compounds (PL-conjugates) of the present invention are described by the general formula:

[phosphatidylethanolamine-Y—]$_n$—X

[phosphatidylserine-Y—]$_n$—X

[phosphatidylcholine-Y—]$_n$—X

[phosphatidylinositol-Y—]$_n$—X

[phosphatidylglycerol-Y—]$_n$—X wherein

Y is either nothing or a spacer group ranging in length from 2 to 30 atoms; and

X is either a physiologically acceptable monomer, dimer, or oligomer, wherein n is unity, or a physiologically acceptable polymer, wherein n is a number from 1 to 1,000.

These phospholipid compounds, known herein as phospholipid conjugates (PL-conjugates) are now disclosed to possess an unusual combination of multiple and potent pharmacological effects in addition to the ability to inhibit the extracellular form of the enzyme phospholipase $A_2$. The set of compounds comprising phosphatidylethanolamine covalently bound to a physiologically acceptable monomer or polymer, is referred to herein as the PE-conjugates. Related derivatives, in which either phosphatidylserine, phosphatidylcholine, phosphatidylinositol, or phosphatidylglycerol are employed in lieu of phosphatidylethanolamine as the phospholipid moiety provide equivalent therapeutic results, based upon the biological experiments described below for the PL-conjugates and the structural similarities shared by these compounds. Other phospholipid-conjugate derivatives relevant to this invention are PL-conjugates wherein at least one of the fatty acid groups of the phospholipid moieties at position C1 or C2 of the glycerol backbone are substituted by a long chain alkyl group attached in either ether or alkyl bonds, rather than ester linkage.

As defined by the structural formulae provided herein for the PL-conjugates, these compounds may contain between one to one thousand phospholipid moieties bound to a single physiologically acceptable polymer molecule.

Administration of the PL-conjugates in a diversity of animal and cell models of disease invokes remarkable, and unexpected, cytoprotective effects, which are useful in the treatment of disease. They are able to stabilize biological membranes; inhibit cell proliferation; suppress free radical production; suppress nitric oxide production; reduce cell migration across biological barriers; influence chemokine levels, including MCP-1, ENA-78, Gro α, and CX3C; affect gene transcription and modify the expression of MHC antigens; bind directly to cell membranes and change the water structure at the cell surface; inhibit the uptake of oxidized lipoprotein; prevent airway smooth muscle constriction; suppress neurotransmitter release; reduce expression of tumor necrosis factor-α (TNF-α); modify expression of transcription factors such as NFκβ; inhibit extracellular degradative enzymes, including collagenase, heparinase, hyaluronidase, in addition to that of $PLA_2$; and inhibit viral infection of white cells. Thus the PL-conjugates provide far-reaching cytoprotective effects to an organism suffering from a disease wherein one or more of the presiding pathophysiological mechanisms of tissue damage entails either oxidation insult giving rise to membrane fragility; hyperproliferation behavior of cells giving rise to stenotic plaque formation in vascular tissue, angiogenesis and benign or malignant cancer disease, or psoriasis; aberrant cell migration giving rise to brain injury or tumor cell metastases; excessive expression of chemokines and cytokines associated with central nervous system (CNS) insult, sepsis, ARDS, or immunological disease; cell membrane damage giving rise to CNS insult, CVS disease, or hemolysis; peroxidation of blood proteins and cell membranes giving rise to atherosclerosis or reperfusion injury; excessive nitric oxide production giving rise to CNS insult, reperfusion injury, and septic shock; interaction with major histocompatability antigens (MHC) associated with autoimmune diseases and alloimmune syndromes, such as transplant rejection.

In the present invention the useful pharmacological properties of the PL-conjugates are reduced to clinical use and disclosed herein as methods for treatment of disease. The biological basis of these methods may be readily demonstrated by standard cellular and animal models of disease as described below.

While pharmacological activity of the PL-conjugates described herein may be due in part to the nature of the phospholipid moiety, the multiple and diverse combination of pharmacological properties observed for the PL-conjugates emerges ability of the compound structure to act essentially as several different drugs in one chemical entity. Thus, for example, internal mucosal injury, as may occur in colitis or Crohn's disease, may be attenuated by any one or all of the pharmaceutical activities of immune suppression, anti-inflammation, anti-oxidation, nitric oxide production, or membrane stabilization. Protection of blood vessels from periluminal damage, as may occur in atherosclerosis, may entail activity from anti-proliferative, anti-chemokine, antioxidant, or antimigratory effects. Treatment of obstructive respiratory disease may involve any one of the many activities of the PL-conjugates ranging from suppression of nitric oxide, anti-chemokine, anti-proliferative, or membrane stabilization effects.

Proliferation of vascular tissue is an element of both the atherogenesis of sclerotic plaques as well as a feature of primary and metastatic cancer lesion growth. Stabilization of biological membranes may prevent hemolysis as well as mucosal bowel injury. Attenuation of chemokine levels may ameliorate ARDS as well as militate against atherogenesis. Anti-oxidant activity protects may protect against reperfusion injury as well as CNS insult, atherosclerosis, and hemolysis. These and other advantages of the present invention will be apparent to those skilled in the art based on the following description.

In another embodiment, the invention provides a method of treating a subject afflicted with chlamydia infection, comprising the steps of administering to a subject an effective amount of a lipid or phospholipid moiety bonded to a physiologically acceptable monomer, dimer, oligomer, or polymer, thereby treating the subject afflicted with chlamydia infection.

In another embodiment, the invention provides a method of treating a subject afflicted with chlamydia infection, comprising the steps of administering to a subject an effective amount of a lipid or phospholipid moiety bonded to a physiologically acceptable monomer, dimer, oligomer, or polymer, wherein the physiologically acceptable monomer is either a salicylate, salicylic acid, aspirin, a monosaccharide, lactobionic acid, maltose, an amino acid, glycine, carboxylic acid, acetic acid, butyric acid, dicarboxylic acid, glutaric acid, succinic acid, fatty acid, dodecanoic acid, didodecanoic acid, bile acid, cholic acid, cholesterylhemmisuccinate; or wherein the physiologically acceptable dimer or oligomer is a dipeptide, a disaccharide, a trisaccharide, an oligopeptide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid; or wherein the physiologically acceptable polymer is a glycosaminoglycan, polygelin ('hemaccell'), alginate, hydroxyethyl starch (hetastarch), polyethylene glycol, polycarboxylated polyethylene glycol, chondroitin-6-sulfate, chondroitin-4-sulfate, keratin, keratin sulfate, heparan sulfate, dermatin, dermatan sulfate, carboxymethylcellulose, heparin, dextran, or hyaluronic acid.

In another embodiment, the invention provides a method of treating a subject afflicted with chlamydia infection, comprising the steps of administering to a subject an effective amount of a lipid or phospholipid moiety bonded to a physiologically acceptable monomer, dimer, oligomer, or polymer, wherein the lipid or phospholipid moiety is either phosphatidic acid, an acyl glycerol, monoacylglycerol, diacylglycerol, triacylglycerol, sphingosine, sphingomyelin, chondroitin-4-sulphate, chondroitin-6-sulphate, ceramide, phosphatidylethanolamine, phosphatidylserine, phosphatidylcholine, phosphatidylinositol, or phosphatidylglycerol, or an ether or alkyl phospholipid derivative thereof, and the physiologically acceptable monomer or polymer moiety is either aspirin, lactobionic acid, maltose, glutaric acid, polyethylene glycol, carboxymethylcellulose, heparin, dextran, hemacell, hetastarch, or hyaluronic acid.

The use of a single chemical entity with potent anti-oxidant, membrane-stabilizing, anti-proliferative, anti-chemokine, anti-migratory, and anti-inflammatory activity provides increased cytoprotection relative to the use of several different agents each with a singular activity. The use of a single agent having multiple activities over a combination or plurality of different agents provides uniform delivery of an active molecule, thereby simplifying issues of drug metabolism, toxicity and delivery. The compounds of the present invention also exhibit properties present only in the combined molecule, not in the individual components.

The compounds may be used for acute treatment of temporary conditions, or may be administered chronically, especially in the case of progressive, recurrent, or degenerative disease. The concentrations of the compounds will depend on various factors, including the nature of the condition to be treated, the condition of the patient, the route of administration and the individual tolerability of the compositions.

The present invention also provides low-molecular weight phospholipid-conjugates, previously undisclosed and unknown to possess pharmacological activity, of the general formula Phosphatidylethanolamine-Y—X Phosphatidylserine-Y—X Phosphatidylcholine-Y—X Phosphatidylinositol-Y—X Phosphatidylglycerol-Y—X wherein
Y is either nothing or a spacer group ranging in length from 2 to 30 atoms; and
X is either a mono- or disaccharide, carboxylated mono- of disaccharide, a mono- or dicarboxylic acid, a salicylate, salicylic acid, aspirin, an amino acid, a dipeptide, or an oligopeptide, a bile acid, a fatty acid, or a di- or trisaccharide monomer unit of heparin, heparan sulfate, hyaluronic acid, chondroitin, chondroitin-6-sulfate, chondroitin-4-sulfate dermatin, dermatan sulfate, keratin, or keratan sulfate.

These low-molecular weight PL-conjugate derivatives also possess wide-spectrum pharmacological activity and, as pharmaceutical agents administered to treat disease, are considered analogous to the PL-conjugates comprised from high molecular weight polymers. Other phospholipid-conjugate derivatives relevant to this invention are phospholipid moieties in which at least one of the two long chain alkyl groups in position C1 and C2 of the glycerol backbone are attached in ether or alkyl bonds, rather than ester linkage.

The present invention is further illustrated in the following examples of the therapeutic PL-conjugate compounds, their chemical preparation, their anti-disease activity, and methods of use as pharmaceutical compositions in the treatment of disease.

Preferred Compounds

In the methods of the present invention, the PL-conjugates administered to the subject are comprised from at least one phospholipid moiety covalently bound through an atom of the polar head group to a monomer or polymeric moiety (referred to herein as the conjugated moiety) of either low or high molecular weight. When desired, an optional bridging moiety can be used to link the PL moiety to the monomer or polymeric moiety. The conjugated moiety may be a low molecular weight carboxylic acid, dicarboxylic acid, fatty acid, dicarboxylic fatty acid, acetyl salicylic acid, cholic acid, cholesterylhemisuccinate, or mono- or di-saccharide, an amino acid or dipeptide, an oligopeptide, a glycoprotein mixture, a di- or trisaccharide monomer unit of a glycosaminoglycan such as a repeating unit of heparin, heparan sulfate, hyaluronic acid, chondrotin-sulfate, dermatan, keratan sulfate, or a higher molecular weight peptide or oligopeptide, a polysaccharide, polyglycan, protein, glycosaminoglycan, or a glycoprotein mixture. From a composition aspect, phospholipid-conjugates of high molecular weight, and associated analogues, are the subject of U.S. Pat. No. 5,064,817, as well as the publications cited herein.

When the conjugated carrier moiety is a polymer, the ratio of PL moieties covalently bound may range from one to one thousand PL residues per polymer molecule, depending upon the nature of the polymer and the reaction conditions employed. For example, the relative quantities of the starting materials, or the extent of the reaction time, may be modified in order to obtain PL-conjugate products with either high or low ratios of PL residues per polymer, as desired.

The term "moiety" means a chemical entity otherwise corresponding to a chemical compound, which has a valence satisfied by a covalent bond.

Examples of polymers which can be employed as the conjugated moiety for producing PL-conjugates for use in the methods of this invention are physiologically acceptable polymers, including water-dispersible or -soluble polymers of various molecular weights and diverse chemical types, mainly plasma expanders, food and drug additives, natural and synthetic polyglycosaminoglycans, including "Hemaccell" (degraded gelatin polypeptide crosslinked via urea bridges, produced by "Behring"), "hydroxyethylstarch" (HES), polyaminoacids, hydrocarbon polymers (e.g., polyethylene), polystyrenes, polyesters, polyamides, polyethylene oxides (e.g. polyethyleneglycols, polycarboxyethyleneglycol), polyvinylpyrrolidones, polysaccharides, soluble cellulose derivatives (e.g., methylcellulose, carboxymethylcellulose), alginates, assimilable gums (e.g., xanthan gum), peptides, injectable blood proteins (e.g., serum albumin), dextrans, cyclodextrin, hyaluronic acid, heparin, heparin sulfate, chondrotin sulfate, chondrotin-6-sulfate, chondroitin-4-sulfate, keratin sulfate, dermatin sulfate and derivatives thereof.

Examples of monomers, dimers, and oligomers which can be employed as the conjugated moiety for producing PL-conjugates for use in the methods of the invention are mono- or disaccharides, carboxylic acid, dicarboxylic acid, fatty acid, dicarboxylic fatty acid, acetyl salicylic acid, cholic acid, cholesterylhemisuccinate, and di- and trisaccharide unit monomers of glycosaminoglycans including heparin, heparan sulfate, hyaluronic acid, chondrotin, chondroitin-6-sulfate, chondroitin-4-sulfate, dermatin, dermatan sulfate, keratin, keratan sulfate, or dextran.

In some cases, the monomer or polymer chosen for preparation of the PL-conjugate may in itself have select biological properties. For example, both heparin and hyaluronic acid are materials with known physiological functions. In the present invention, however, the PL-conjugates formed from these substances as starting materials display a new and wider set of pharmaceutical activities than would be predicted from administration of either heparin or hyaluronic acid which have not been bound by covalent linkage to a phospholipid. It can be shown, by standard comparative experiments as described below, that PE-carboxymethylcellulose (referred to as CMPE and CMC-PE), PE-hyaluronic acid (referred to as HYPE, HyPE, and Hyal-PE) and PE-heparin (referred to as HEPPE, HepPE, and heparin-linked PE) are far superior in terms of potency and range of useful pharmaceutical activity to either carboxymethylecellulose (CMC), heparin, or hyaluronic acid, respectively. In fact, these latter two substances are, in general, not considered useful in methods for treatment of most of the diseases described herein, and for those particular cases wherein their use is medically prescribed, such as ischemic vascular disease, the concentrations for their use as drugs are are several orders of magnitude higher. Thus, the combination of a phospholipid such as phosphatidylethanolamine, or related phospholipids which differ with regard to the polar head group, such as phosphatidylserine (PS), phosphatidylcholine (PC), phosphatidylinositol (PI), and phosphatidylglycerol (PG), results in the formation of a compound which has novel pharmacological properties when compared to the starting materials alone.

The biologically active phospholipid conjugates described herein can have a wide range of molecular weight, e.g., above 50,000 (up to a few hundred thousands) when it is desirable to retain the PL conjugate in the vascular system and below 50,000 when targeting to extravascular systems is desirable. The sole limitation on the molecular weight and the chemical structure of the conjugated moiety is that it does not result in a PL-conjugate devoid of the desired biological activity, or lead to chemical or physiological instability to the extent that the PL-conjugate is rendered useless as a drug in the method of use described herein.

PE-conjugates are defined herein as compounds of the structure

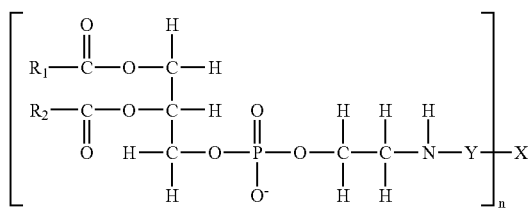

(I)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Y is either nothing or a spacer group ranging in length from 2 to 30 atoms; and
X is either a physiologically acceptable monomer, dimer, oligomer, wherein n is unity, or a physiologically acceptable polymer, wherein n is a number from 1 to 1,000.

Preferred compounds for use in the methods of the invention comprise one of the following as the conjugated moiety X: acetate, butyrate, glutarate, succinate, dodecanoate, didodecanoate, maltose, lactobionic acid, dextran, alginate, aspirin, cholate, cholesterylhemisuccinate, carboxymethyl-cellulose, heparin, hyaluronic acid, hemaccell, polyethyleneglycol, and polycarboxylated polyethylene glycol. The polymers used as starting material to prepare the PE-conjugates may vary in molecular weight from 1 to 2,000 kDa.

Examples of phosphatidylethanolamine (PE) moieties are analogues of the phospholipid in which the chain length of the two fatty acid groups attached to the glycerol backbone of the phospholipid varies from 2–30 carbon atoms length, and in which these fatty acids chains contain saturated and/or unsaturated carbon atoms. In lieu of fatty acid chains, alkyl chains attached directly or via an ether linkage to the glycerol backbone of the phospholipid are included as analogues of PE. According to the present invention, a most preferred PE moiety is dipalmitoylphosphatidylethanolamine.

Phosphatidyl-ethanolamine and its analogues may be from various sources, including natural, synthetic, and semi-synthetic derivatives and their isomers.

Phospholipids which can be employed in lieu of the PE moiety are N-methyl-PE derivatives and their analogues, linked through the amino group of the N-methyl-PE by a covalent bond; N,N-dimethyl-PE derivatives and their analogues linked through the amino group of the N,N-dimethyl-PE by a covalent bond, phosphatidylserine (PS) and its analogues, such as palmitoyl-stearoyl-PS, natural PS from various sources, semisynthetic PSs, synthetic, natural and artifactual PSs and their isomers. Other phospholipids useful as conjugated moieties in this invention are phosphatidylcholine (PC), phosphatidylinositol (PI), and phosphoatidylglycerol (PG), as well as derivatives thereof comprising either phospholipids, lysophospholipids, phosphatidylic acid, sphingomyelins, lysosphingomyelins, ceramide, and sphingosine.

For PE-conjugates and PS-conjugates, the phospholipid is linked to the conjugated monomer or polymer moiety through the nitrogen atom of the phospholipid polar head group, either directly or via a spacer group. For PC, PI, and PG conjugates, the phospholipid is linked to the conjugated monomer or polymer moiety through either the nitrogen or one of the oxygen atoms of the polar head group, either directly or via a spacer group.

PS-conjugates are defined herein as compounds of the structure

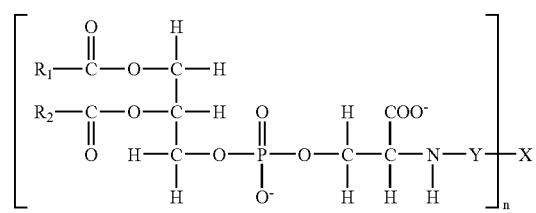

(II)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is either a physiologically acceptable monomer, dimer, oligomer, or a physiologically acceptable polymer wherein n is a number from 1 to 1,000.

PC, PI, and PG conjugates are herein defined as compounds of the general structure (III)

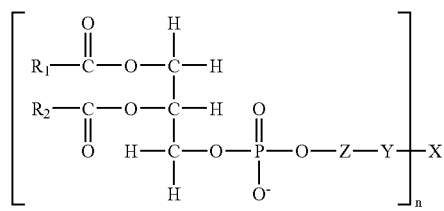

(III)

wherein $R_1$ is a linear, saturated, mono-unsaturated, or polyunsaturated, alkyl chain ranging in length from 2 to 30 carbon atoms;

$R_2$ is a linear, saturated, mono-unsaturated, or polyunsaturated, alkyl chain ranging in length from 2 to 30 carbon atoms;

Z is either inositol, choline, or glycerol;

Y is either nothing or a spacer group ranging in length from 2 to 30 atoms; and

X is either a physiologically acceptable monomer, dimer, oligomer, wherein n is unity, or a physiologically acceptable polymer, wherein n is a number from 1 to 1,000.

Examples of suitable divalent groups forming the optional bridging group Y are straight- or branched-chain alkylene, e.g., of 2 or more, preferably 4 to 30 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 30 atoms in the chain, —(—O—CH(CH$_3$)CH$_2$—)$_x$— wherein X is an integer of 1 or more.

In addition to the traditional phospholipid structure, related derivatives for use in this invention are phospholipids modified at the C1 or C2 position to contain an ether or alkyl bond instead of an ester bond. The alkyl phospholipid derivatives and ether phospholipid derivatives are exemplified by the general formulae

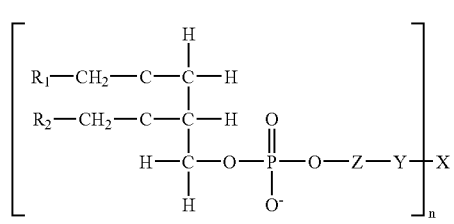

(IV)

or

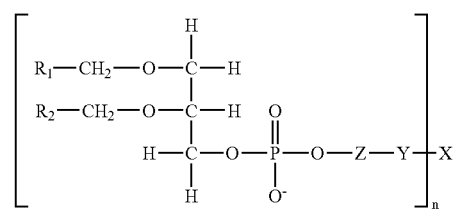

(V)

wherein $R_1$ is a linear, saturated, mono-unsaturated, or polyunsaturated, alkyl chain ranging in length from 2 to 30 carbon atoms;

$R_2$ is a linear, saturated, mono-unsaturated, or polyunsaturated, alkyl chain ranging in length from 2 to 30 carbon atoms;

Z is either ethanolamine, serine, inositol, choline, or glycerol;

Y is either nothing or a spacer group ranging in length from 2 to 30 atoms; and

X is either a physiologically acceptable monomer, dimer, oligomer, wherein n is unity, or a physiologically acceptable polymer, wherein n is a number from 1 to 1,000.

Illustrative of preferred PL-conjugates for use in the methods of this invention are those in which the PL moiety is linked directly or indirectly through a bridging moiety listed below.

| phospholipid | spacer | polymer (m.w.) | abbreviation |
|---|---|---|---|
| PE | Dicarboxylic acid + Diamine | Polygeline (4–40 kDa) | HeMPE; HemPE |
| PE | None | Carboxymethylcellulose (60–200 kDa) | CMPE; CMC-PE |
| PE | None | Hyaluronic acid (20–120 kDa) | HYPE (HyPE) |
| PE | Dipalmitoic acid | Hyaluronic acid (30 kDa) | HYPE-dipalmitate |
| PE | None | Polyethylene | |
| PE | Y | Hydroxyethylstarch | HESPE; HesPE |
| PE | Dicarboxylic acid + Diamine | Dextran (1–2,000 kDa) | DEXPE |
| PE | None | Albumin | |
| PE | None | Alginate | |
| PE | None | Polyaminoacid | |
| PE | None | Lactobionic acid | |
| PE | None | Acetylsalicylate | |
| PE | None | Cholesteryl-hemmisuccinate | |
| PE | None | Maltose | |
| PE | Y | None | Cholic acid |
| PE | None | Polycarboxylated polyethylene glycol | |
| PE | None | Heparin (0.5–110 kDa) | HEPPE; HEPE; HepPE |
| Dimyristoyl-PE | Y | Variable | DMPE |
| Dimyristoyl-PE | Y | Hyaluronic acid | HyDMPE |
| PS | Y | Polygeline (hemaccell) | |
| PS | Y | Heparin | |
| PS | Y | Hyaluronic acid | |
| PC | Y | Polygeline | |
| PC | Y | Heparin | |
| PC | Y | Hyaluronic acid | |

-continued

| phospholipid | spacer | polymer (m.w.) | abbreviation |
|---|---|---|---|
| PI | Y | Polygeline | |
| PI | Y | Heparin | |
| PI | Y | Hyaluronic acid | |
| PG | Y | Polygeline | |
| PG | Y | Heparin | |
| PE | Y | Chondoitin sulfate | CSAPE |
| PE | Y | Hemaccel | |
| PG | Y | Hyaluronic acid | |

In particularly preferred modes of the invention, the compounds administered are hemacell-PE, hetastarch-PE, chondrotin-sulphate-PE, spirin-PE, hyaluronic acid_PE, CMPE, HEPE, HYPE, and DEXPE, and pharmaceutically acceptable salts thereof, in combination with a physiologically acceptable carrier or solvent. These polymers, when chosen as the conjugated moiety, may vary in molecular weights from 500 to 2,000,000 daltons. Various molecular weight species have been shown to have the desired biological efficacy, as shown in the section below.

In addition to the compounds of the Examples, further illustrative compounds of this invention are set forth in the section below.

Novel Compounds

Low molecular weight PL-conjugates, in which the conjugated moiety is a monomer such as a salicylate, a bile acid, or cholesterylhemmisuccinate, or a di- or trisaccaharide unit monomer of a polyglycosoaminoglycan such as heparin, heparan sulfate, chondrotin-6-sulfate, chondroitin-4-sulfate, hyaluronic acid, kearatin, keratan sulfate, dermatin, or dermatan sulfate, have not been described before. These new compounds display a similar biological activity profile as demonstrated below for the other PL-conjugates and have the general formula Phosphatidylethanolamine-Y—X Phosphatidylserine-Y—X Phosphatidylcholine-Y—X Phosphatidylinositol-Y—X Phosphatidylglycerol-Y—X wherein Y is either nothing or a spacer group ranging in length from 2 to 30 atoms; and X is either a mono- or disaccharide, carboxylated disaccharide, mono- or dicarboxylic acid, salicylate, acetyl salicylate, aspirin, amino acid, di-amino acid, oligopeptide, bile acid, fatty acid, or a di- or trisaccaride monomer unit of heparin, heparan sulfate, hyaluronic acid, chondroitin-6-sulfate, chondroitin-4-sulfate, dermatan, dermatan sulfate, keratin, or keratan sulfate.

Low molecular weight PE-conjugates are defined herein as compounds of the structure

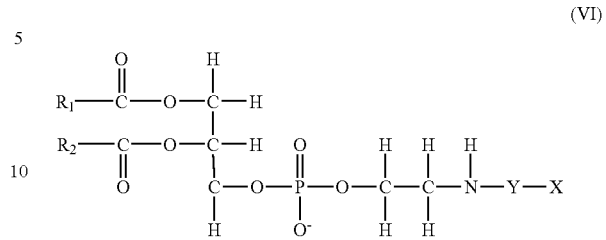

(VI)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is either a mono- or disaccharide, carboxylated disaccharide, mono- or dicarboxylic acid, salicylate, acetyl salicylate, aspirin, amino acid, di-amino acid, or oligopeptide, bile acid, fatty acid, or di- or trisaccharide monomer unit of heparin, heparan sulfate, hyaluronic acid, chondroitin-6-sulfate, dermatan, or keratan sulfate.

Low molecular weight PS-conjugates are defined herein as compounds of the structure

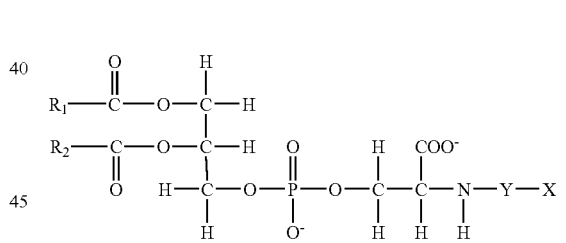

(VII)

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Y is either nothing or a spacer group ranging in length from 2 to 30 atoms; and

X is either a mono- or disaccharide, carboxylated disaccharide, mono- or dicarboxylic acid, salicylate, acetyl salicylate, aspirin, amino acid, di-amino acid, or oligopeptide, bile acid, fatty acid, or di- or trisaccharide monomer unit of heparin, heparan sulfate, hyaluronic acid, chondroitin-6-sulfate, dermatan, or keratan sulfate.

Low molecular weight PC, PI, and PG conjugates are herein defined as compounds of the structure

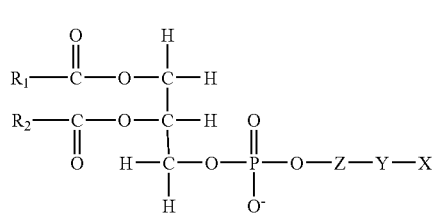

(VIII)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is inositol, choline, or glycerol;
Y is either nothing or a spacer group ranging in length from 2 to 30 atoms; and
X is either a mono- or disaccharide, carboxylated disaccharide, mono- or dicarboxylic acid, salicylate, acetyl salicylate, aspirin, amino acid, di-amino acid, or oligopeptide, bile acid, fatty acid, or di- or trisaccharide monomer unit of heparin, heparan sulfate, hyaluronic acid, chondroitin-6-sulfate, dermatan, or keratan sulfate.

Examples of suitable divalent groups forming the optional bridging group Y are straight- or branched-chain alkylene, e.g., of 2 or more, preferably 4 to 18 carbon atoms, —CO-alkylene-CO, —NH-alkylene-NH—, —CO-alkylene-NH—, cycloalkylene, wherein alkylene in each instance, is straight or branched chain and contains 2 or more, preferably 2 to 18 carbon atoms in the chain, —(—O—CH(CH$_3$)CH$_2$—)$_x$— wherein x is an integer of 1 or more.

In addition to the traditional phospholipid structure, related derivatives for use in this invention are phospholipids modified at the C1 or C2 position to contain an ether or alkyl bond instead of an ester bond. These derivatives are exemplified by the general formulae

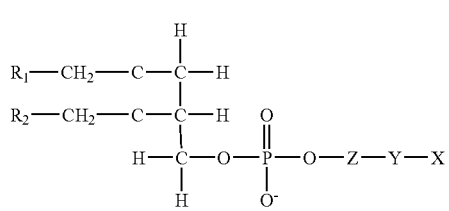

(IX)

or

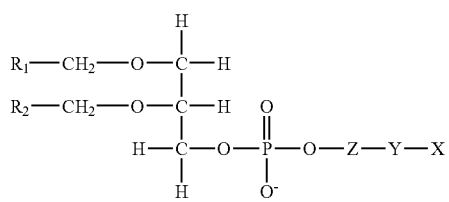

(X)

wherein
$R_1$ is a linear, saturated, mono-unsaturated, or poly-unsaturated, alkyl chain ranging in length from 2 to 30 carbon atoms;
$R_2$ is a linear, saturated, mono-unsaturated, or poly-unsaturated, alkyl chain ranging in length from 2 to 30 carbon atoms;
Z is either, ethanolamine, serine, inositol, choline, or glycerol;
Y is either nothing or a spacer group ranging in length from 2 to 30 atoms; and
X is either a mono- or disaccharide, carboxylated disaccharide, mono- or dicarboxylic acid, salicylate, acetyl salicylate, aspirin, amino acid, di-amino acid, or oligopeptide, bile acid, fatty acid, or di- or trisaccharide monomer unit of heparin, heparan sulfate, hyaluronic acid, chondroitin-6-sulfate, dermatan, or keratan sulfate.

Preparation of Compounds

The preparation of some high molecular weight PL-conjugates is the subject of U.S. Pat. No. 5,064,817, which is incorporated herein by reference. These synthetic methods are reiterated below and are considered to be applicable as well to the preparation of low molecular, i.e. PL-conjugates comprising monomers and dimers as the conjugated moiety, with modifications in the procedure as readily evident to one skilled in the art.

When the starting compound chosen for the conjugated moiety has a substituent which is or can be rendered reactive to a substituent on the starting PL compound, the conjugated carrier moiety may be linked directly to PL to produce the PL-conjugate. When it does not, a bifunctional linking starting material can be used to link the two molecules indirectly.

PL-conjugates are prepared by linking a polar conjugate, e.g., a monomer or polymer, directly or indirectly to a PL moiety according to the general reaction schemes delineated in U.S. Pat. No. 5,064,817.

For example, with acylated PE used as precursor for the PE conjugate, various lengths of dicarboxylic acids can be used as spacers. These acids can be linked to natural, semi-synthetic or synthetic PE.

For example, PE can be linked to aminodextran indirectly as delineated in U.S. Pat. No. 5,064,817.

Polymers with carboxylic groups, such as polyamino acids, carboxymethyl cellulose or polymers to which fatty acids have been linked, can be linked directly to PE according to the scheme delineated in U.S. Pat. No. 5,064,817.

It is to be understood that these examples are given by way of illustration only and are not to be construed as limiting the invention either in spirit of in scope, as many modifications both in reagents and methods could be possible to those skilled in the art. Based on the wide spectrum of pharmacological properties exhibited by PL-conjugates, it is likely that compounds covered by Formula I-X, in addition to those explicitly described above, have the same valuable biological activities demonstrate to be useful in the methods of treating disease described below.

Methods of Treating Disease Based on PL Conjugates

The PL-conjugates described herein can be used to treat disease, through exerting at least one of their many pharmacological activities, among which are amelioration, or prevention, of tissue injury arising in the course of pathological disease states by stabilizing cell membranes; limiting oxidative damage to cell and blood components; limiting cell proliferation, cell extravasation and (tumor) cell migratory behavior; suppressing immune responses; or attenuating physiological reactions to stress, as expressed in elevated chemokine levels. The medicinal properties of these compounds is readily exemplified in using animal models of the particular disease in which it is desired to use the drug. The patients to whom the PL conjugates should be administered are those that are experiencing symptoms of disease or who are at risk of contracting the disease or experiencing a recurrent episode or exacerbation of the disease.

The efficacy of these compounds in cellular and animal models of disease are described below in The Examples.

The combination of phospholipids, in particular phosphatidylethanolamine and phosphatidylserine, with additional monomer or polymer moieties, is thus a practical route to the production of new drugs for medical purposes, provided that the resultant chemical composition displays the desired range of pharmacological properties. In the cases described herein, the diversity of biological activities and the effectiveness in disease exhibited by the compounds far exceed the properties anticipated by use of the starting materials themselves, when administered alone or in combination. However, it is likely that the PL conjugate compounds, alone or in combination, will prove to be valuable drugs when adapted to methods of disease treatment other to those conditions specifically described herein.

The present invention provides a method of treating a subject requiring anti-oxidant therapy, comprising the steps of administering to a subject an effective amount of a lipid or phospholipid moiety bonded to a physiologically acceptable monomer, dimer, oligomer, or polymer, thereby treating the subject requiring anti-oxidant therapy.

The present invention provides a method of treating a subject requiring anti-TNF therapy, comprising the steps of administering to a subject an effective amount of a lipid or phospholipid moiety bonded to a physiologically acceptable monomer, dimer, oligomer, or polymer, thereby treating the subject requiring anti-TNF therapy.

The present invention provides a method of treating a subject suffering from a disorder of smooth muscle cell proliferation, comprising the steps of administering to a subject an effective amount of a lipid or phospholipid moiety bonded to a physiologically acceptable monomer, dimer, oligomer, or polymer, thereby treating the subject with a disorder of smooth muscle cell proliferation.

The present invention provides a method of treating a subject undergoing vascular catheterization, comprising the steps of administering to a subject an effective amount of a lipid or phospholipid moiety bonded to a physiologically acceptable monomer, dimer, oligomer, or polymer, thereby treating the subject undergoing vascular catheterization.

The present invention provides a method of treating a subject suffering from metastatic cancer, comprising the steps of administering to a subject an effective amount of a lipid or phospholipid moiety bonded to a physiologically acceptable monomer, dimer, oligomer, or polymer, thereby treating the subject with metastatic cancer.

The present invention provides a method of treating a subject suffering from obstructive respiratory disease, comprising the steps of administering to a subject an effective amount of a lipid or phospholipid moiety bonded to a physiologically acceptable monomer, dimer, oligomer, or polymer, thereby treating the subject with obstructive respiratory disease.

The present invention provides a method of treating a subject suffering from colitis, Crohn's disease, or another form of intestinal mucosal injury, comprising the steps of administering to a subject an effective amount of a lipid or phospholipid moiety bonded to a physiologically acceptable monomer, dimer, oligomer, or polymer, thereby treating the subject with intestinal mucosal injury, including colitis or Crohn's disease.

The present invention provides a method of treating a subject suffering from cardiovascular disease, comprising the steps of administering to a subject an effective amount of a lipid or phospholipid moiety bonded to a physiologically acceptable monomer, dimer, oligomer, or polymer, thereby treating the subject with cardiovascular disease.

The present invention provides a method of treating a subject suffering from atherosclerosis, comprising the steps of administering to a subject an effective amount of a lipid or phospholipid moiety bonded to a physiologically acceptable monomer, dimer, oligomer, or polymer, thereby treating the subject with atherosclerosis.

The present invention provides a method of treating a subject suffering from central nervous system tissue insult, comprising the steps of administering to a subject an effective amount of a lipid or phospholipid moiety bonded to a physiologically acceptable monomer, dimer, oligomer, or polymer, thereby treating the subject with central nervous system insult.

The present invention provides a method of treating a subject suffering from multiple sclerosis, comprising the steps of administering to a subject an effective amount of a lipid or phospholipid moiety bonded to a physiologically acceptable monomer, dimer, oligomer, or polymer, thereby treating the subject with multiple sclerosis.

The present invention provides a method of treating a subject suffering from contact dermatitis, comprising the steps of administering to a subject an effective amount of a lipid or phospholipid moiety bonded to a physiologically acceptable monomer, dimer, oligomer, or polymer, thereby treating the subject with contact dermatitis.

The present invention provides a method of treating a subject suffering from psoriasis, comprising the steps of administering to a subject an effective amount of a lipid or phospholipid moiety bonded to a physiologically acceptable monomer, dimer, oligomer, or polymer, thereby treating the subject with psoriasis.

The present invention provides a method of treating a subject suffering from a cellular proliferative disorder, comprising the steps of administering to a subject an effective amount of a lipid or phospholipid moiety bonded to a physiologically acceptable monomer, dimer, oligomer, or polymer, thereby treating the subject with a cellular proliferative disorder.

The present invention provides a method of treating a subject suffering from sepsis, comprising the steps of administering to a subject an effective amount of a lipid or phospholipid moiety bonded to a physiologically acceptable monomer, dimer, oligomer, or polymer, thereby treating the subject with sepsis.

The present invention provides a method of treating a subject suffering from ARDS, comprising the steps of administering to a subject an effective amount of a lipid or phospholipid moiety bonded to a physiologically acceptable monomer, dimer, oligomer, or polymer, thereby treating the subject with ARDS.

The present invention provides a method of treating a subject suffering from autoimmune disease, comprising the steps of administering to a subject an effective amount of a lipid or phospholipid moiety bonded to a physiologically acceptable monomer, dimer, oligomer, or polymer, thereby treating the subject with autoimmune disease.

The present invention provides a method of treating a subject suffering from hemolysis, comprising the steps of administering to a subject an effective amount of a lipid or phospholipid moiety bonded to a physiologically acceptable monomer, dimer, oligomer, or polymer, thereby treating the subject with hemolysis.

The present invention provides a method of treating a subject undergoing tissue transplantation or allograft rejection, comprising the steps of administering to a subject an effective amount of a lipid or phospholipid moiety bonded to a physiologically acceptable monomer, dimer, oligomer, or polymer, thereby treating the subject undergoing tissue transplantation or allograft rejection.

The present invention provides a method of treating a subject afflicted with HIV infection, comprising the steps of administering to a subject an effective amount of a lipid or phospholipid moiety bonded to a physiologically acceptable monomer, dimer, oligomer, or polymer, thereby treating the subject afflicted with HIV infection.

The present invention provides a method of treating a subject afflicted with conjunctivitis, comprising the steps of administering to a subject an effective amount of a lipid or phospholipid moiety bonded to a physiologically acceptable monomer, dimer, oligomer, or polymer, thereby treating the subject afflicted with conjunctivitis.

The present invention provides a method for extracorporeal tissue preservation, comprising the step of adding to a tissue preparation or organ an effective amount of a lipid or phospholipid moiety bonded to a physiologically acceptable monomer, dimer, oligomer, or polymer, thereby extending the viability of the tissue preparation or organ within a donor subject.

The present invention provides a method of treating a subject afflicted with chlamydia infection, comprising the steps of administering to a subject an effective amount of a lipid or phospholipid moiety bonded to a physiologically acceptable monomer, dimer, oligomer, or polymer, thereby treating the subject afflicted with chlamydia infection.

The present invention provides a compound according to the formula

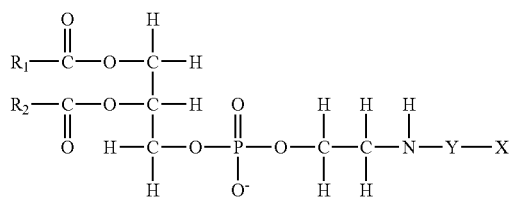

wherein
  $R_1$ is a linear, saturated, mono-unsaturated, or poly-unsaturated, alkyl chain ranging in length from 2 to 30 carbon atoms;
  $R_2$ is a linear, saturated, mono-unsaturated, or poly-unsaturated, alkyl chain ranging in length from 2 to 30 carbon atoms;
  Y is either nothing or a spacer group ranging in length from 2 to 30 atoms; and
  X is either a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisacharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid.

The present invention provides a compound according to the formula

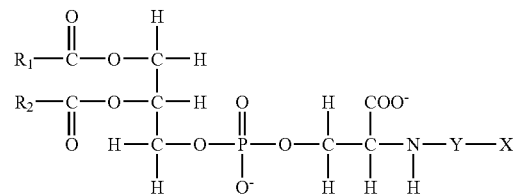

wherein
  $R_1$ is a linear, saturated, mono-unsaturated, or poly-unsaturated, alkyl chain ranging in length from 2 to 30 carbon atoms;
  $R_2$ is a linear, saturated, mono-unsaturated, or poly-unsaturated, alkyl chain ranging in length from 2 to 30 carbon atoms;
  Y is either nothing or a spacer group ranging in length from 2 to 30 atoms; and
  X is either a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid.

The present invention provides a compound according to the formula

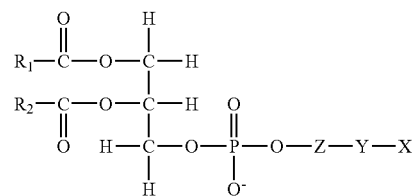

wherein
  $R_1$ is a linear, saturated, mono-unsaturated, or poly-unsaturated, alkyl chain ranging in length from 2 to 30 carbon atoms;
  $R_2$ is a linear, saturated, mono-unsaturated, or poly-unsaturated, alkyl chain ranging in length from 2 to 30 carbon atoms;
  Z is either choline, inositol, or glycerol;
  Y is either nothing or a spacer group ranging in length from 2 to 30 atoms; and
  X is either a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid.

The present invention provides a compound according to the formula

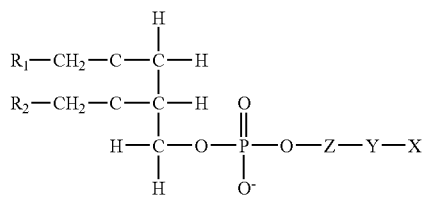

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either ethanolamine, serine, inositol, choline, or glycerol;

Y is either nothing or a spacer group ranging in length from 2 to 30 atoms; and

X is either a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid.

The present invention provides a compound according to the general formula

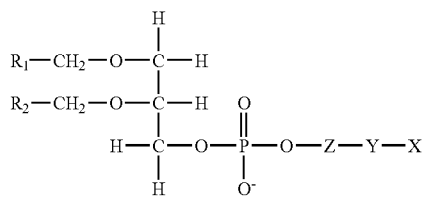

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either lethanolamine, serine, inositol, choline, or glycerol;

Y is either nothing or a spacer group ranging in length from 2 to 30 atoms; and X is either a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid.

The present invention provides a compound according to the formula

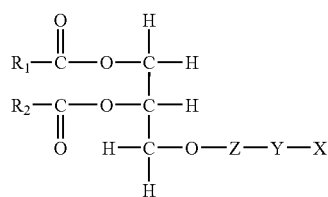

wherein $R_1$ is a linear, saturated, mono-unsaturated, or poly-unsaturated, alkyl chain ranging in length from 2 to 30 carbon atoms;

$R_2$ is a linear, saturated, mono-unsaturated, or poly-unsaturated, alkyl chain ranging in length from 2 to 30 carbon atoms;

Z is either choline, inositol, or glycerol;

Y is either nothing or a spacer group ranging in length from 2 to 30 atoms; and

X is either a mono- or disaccharide, carboxylated disaccharide, mono- or dicarboxylic acids, a salicylate, salicylic acid, aspirin, lactobionic acid, maltose, an amino acid, glycine, acetic acid, butyric acid, dicarboxylic acid, glutaric acid, succinic acid, fatty acid, dodecanoic acid, didodecanoic acid, bile acid, cholic acid, cholesterylhemmisuccinate, a di- or tripeptide, an oligopeptide, a trisaccharide, or a di- or trisaccharide monomer unit of heparin, heparan sulfate, keratin, keratan sulfate, chondroitin, chondoitin-6-sulfate, chondroitin-4-sulfate, dermatin, dermatan sulfate, dextran, or hyaluronic acid.

The present invention provides for use of a phospholipid moiety bonded to a physiologically acceptable monomer, dimer, oligomer, or polymer, in the preparation of a pharmaceutical composition for treating a subject afflicted with obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, and hypersensitivity conjunctivitis.

The present invention provides use of a pharmaceutical composition according to the present invention for treating a subject afflicted with obstructive respiratory disease, colitis, Crohn's disease, central nervous system insult, multiple sclerosis, contact dermatitis, psoriasis, cardiovascular disease, including prophylaxis for invasive procedures, invasive cellular proliferative disorders, anti-oxidant therapy, hemolytic syndromes, sepsis, acute respiratory distress syndrome, tissue transplant rejection syndromes, autoimmune disease, viral infection, or hypersensitivity conjunctivitis, wherein the composition is prepared for administration by topical, oral, nasal, aerosol, intravenous, intraocular, intra-arterial, subcutaneous, or suppository routes.

Dosages and Routes of Administration

The methods of this invention can be adapted to use of the therapeutic compositions comprising PL-conjugates in admixture with conventional excipients, i.e. pharmaceutically acceptable organic or inorganic carrier substances suitable for parenteral, enteral (e.g., oral) or topical application which do not deleteriously react with the active compounds. Suitable pharmaceutically acceptable carriers include but are not limited to water, salt solutions, alcohols, gum arabic, vegetable oils, benzyl alcohols, polyethylene glycols, gelatine, carbohydrates such as lactose, amylose or starch, magnesium stearate, talc, silicic acid, viscous paraffin, white paraffin, glycerol, alginates, hyaluronic acid, collagen, perfume oil, fatty acid monoglycerides and diglycerides, pentaerythritol fatty acid esters, hydroxy methylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

While the examples provided herein describe use of the PL conjugates in subcutaneous, intraperitoneal or topical administration the success described affords good evidence to suppose that other routes of administration, or combinations with other pharmaceutical preparations, would be at least as successful. The route of administration (e.g., topical, parenteral, enteral, intravenous, vaginal, or oral) and the dosage regimen will be determined by skilled clinicians, based on factors such as exact nature of the condition being treated, the severity of the condition, the age and general physical condition of the patient, and so on.

In general, the doses utilized for the above described purposes will vary, but will be in an effective amount to exert the desired anti-disease effect. As used herein, the term "pharmaceutically effective amount" refers to an amount of a compound of formulae I-X which will produce the desired alleviation in symptoms or signs of disease in a patient. The doses utilized for any of the above-described purposes will generally be from 1 to about 1000 milligrams per kilogram of body weight (mg/kg), administered one to four times per day, or by continuous IV infusion. When the compositions are dosed topically, they will generally be in a concentration range of from 0.1 to about 10% w/v, administered 1–4 times per day.

As used herein, the term "pharmaceutically acceptable carrier" refers to any formulation which is safe, and provides the appropriate delivery for the desired route of administration of an effective amount of at least one compound of the present invention. As such, all of the above-described formulations of the present invention are hereby referred to as "pharmaceutically acceptable carriers." This term refers to as well the use of buffered formulations wherein the pH is maintained at a particular desired value, ranging from pH 4.0 to pH 9.0, in accordance with the stability of the compounds and route of administration.

For parenteral application, particularly suitable are injectable, sterile solutions, preferably oily or aqueous solutions, as well as suspensions, emulsions, or implants, including suppositories. Ampoules are convenient unit dosages.

For application by inhalation, particularly for treatment of airway obstruction or congestion, solutions or suspensions of the compounds mixed and aerosolized or nebulized in the presence of the appropriate carrier suitable.

For topical application, particularly for the treatment of contact dermatitis, admixture of the compounds with conventional creams or delayed release patches is acceptable.

For enteral application, particularly suitable are tablets, dragees, liquids, drops, suppositories, or capsules. A syrup, elixir, or the like can be used when a sweetened vehicle is employed. When indicated, suppositories or enema formulations may be the recommended route of administration.

Sustained or directed release compositions can be formulated, e.g., liposomes or those wherein the active compound is protected with differentially degradable coatings, e.g., by microencapsulation, multiple coatings, etc. It is also possible to freeze-dry the new compounds and use the lyophilisates obtained, for example, for the preparation of products for injection.

Thus, the present invention provides for use of the PL-conjugates in various dosage forms suitable for aerosol, rectal, vaginal, conjunctival, intravenous, intra-arterial, and sublingual routes of administration.

It will be appreciated that the actual preferred amounts of active compound in a specific case will vary according to the specific compound being utilized, the particular compositions formulated, the mode of application, and the particular situs and organism being treated. Dosages for a given host can be determined using conventional considerations, e.g., by customary comparison of the differential activities of the subject compounds and of a known agent, e.g., by means of an appropriate, conventional pharmacological protocol.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

EXAMPLE 1

Obstructive Respiratory Disease

PE conjugates are effective in the treatment of obstructive respiratory disease. This is demonstrated for asthma in the Experiments 1–7 below. In asthma, the impeded airflow is due to airway obstruction which is the result of constriction and obstruction of luminal vessels of the lungs. One widely accepted experimental system to investigate airway constriction is to induce muscle preparations isolated from airways to contract in the absence and presence of the drug. Another widely accepted test of anti-asthma drug action is to use live animals which have asthma. This disease is present in animals which have been sensitized to an antigen and which can be monitored for exacerbation and recovery from asthmatic breathing using a body plethysmography.

In Experiments 1–4 the muscle preparation was isolated from rats and in Experiment 5 from guinea pigs. Muscle contraction is measured by attachment of the muscle to a pressure transducer, which works much like a spring. Induction of contraction occurs when asthmatogenic substances are administered such as acetylcholine and endothelin.

Experiment 1

Isolated rat tracheal ring was bathed in Krebs-Hanselet buffer (pH=7.4), and linked to a tension transducer. ET-1 was added to a final concentration as indicated, and the final contraction was determined by the change in the force applied to the tension transducer. Each datum (FIG. 1) is mean S.D. of four separate experiments (4 rats).

Experiment 2

Figure 2:
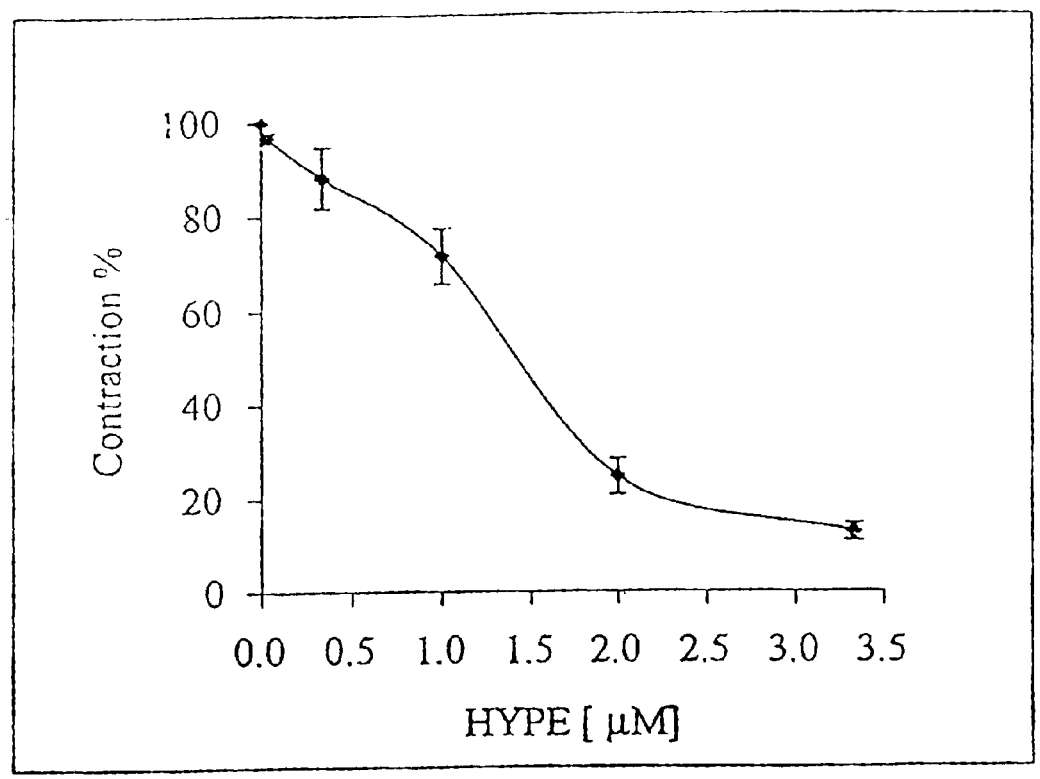
FIG. 2. Inhibition of Tracheal Contraction by HYPE

Rat trachea rings were incubated with HYPE at the indicated concentration for 1 hr. ET-1 was then added to a final concentration of 1 μM and the ring contraction (FIG. 2) was determined as in Experiment 1.

Experiment 3

Figure 3:
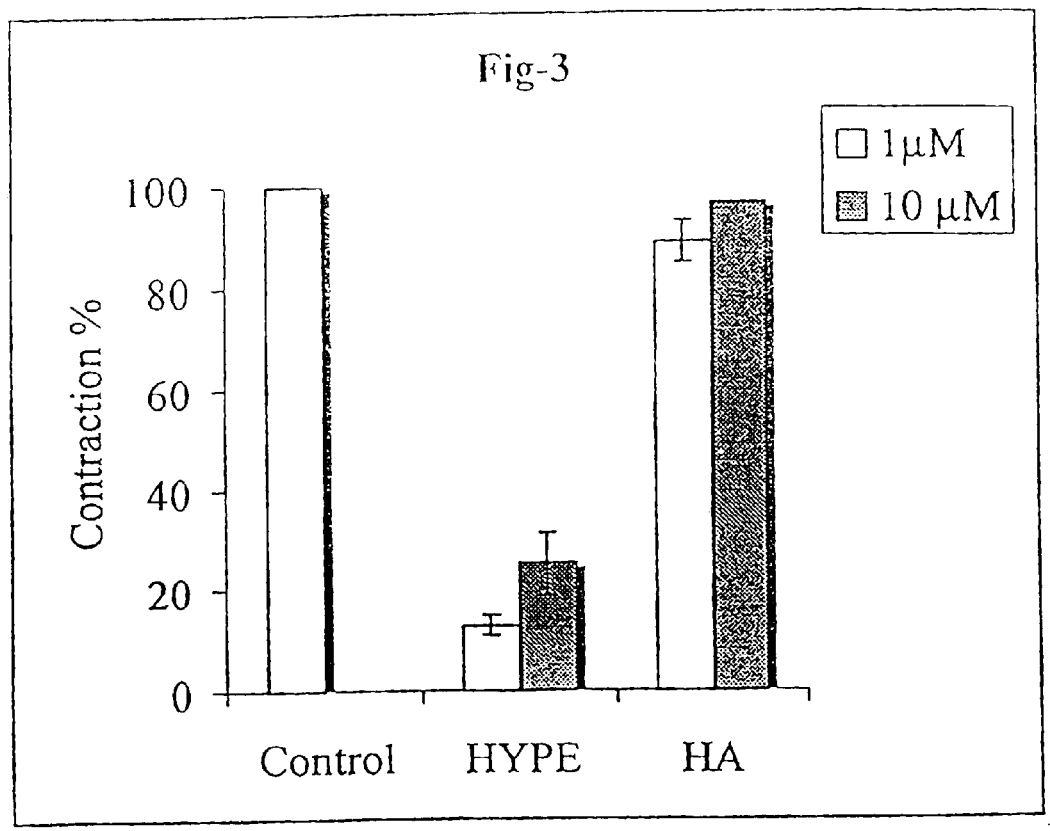
FIG. 3. Inhibition of Tracheal Contraction by HYPE vs Hyaluronic Acid

Rat trachea ring was incubated with 3 μM HYPE or HA for 1 hr. ET-1 was then added to a final concentration of 1 μM (empty bars) or 10 μM (full bars) and the ring contraction (FIG. 3) was determined as in the Experiment 1.

Experiment 4

Guinea pig tracheal rings (in a linear array), immersed in a ringer bath, were connected to an apparatus measuring the length of the ring chain. CMPE was added to the bath 1 h prior to the stimulation of contraction by either Crotalus atrox (type II) enzyme or endothelin-1 as indicated (Table 1).

TABLE 1

Inhibition of Tracheal Contraction by CMPE and HEPPE

| STIMULANT | PL-CONJUGATE | % INHIBITION |
|---|---|---|
| Phospholipase (crotalus atrox type II) 0.5 u/ml | CMPE (10 μM) | 100 |
| Histamine (20 μM) | CMPE (10 μM) | 69 ± 0.1 |
| Histamine (20 μM) | HEPPE (15 μM) | 56 ± 0.05 |
| Endothelin-1 (100 nM) | CMPE (10 μM) | 92 ± 1.1 |

Experiments 5–7 demonstrate the ability of PL conjugates to exert their pharmacological effect in live animals. In this case, the rats were sensitized by injection with ovalbumin and then tested for asthmatic disease upon re-exposure to the antigen through the respiratory route. For these experiments, asthma was induced in Brown Norway (BN) rats by subcutaneous (S.C.) injection of ovalbumin (OA) with aluminum hydroxide and intraperitoneal (I.P.) injection of heat-killed Bordatella Pertussis on day 1. Bronchoconstriction (challenge) was induced on days 14, 16 and 18 by aerosolic administration of OA. Pulmonary functions were tested with each rat in a body-box on day 18, 5 min. after challenge.

Experiment 5

Figure 4:
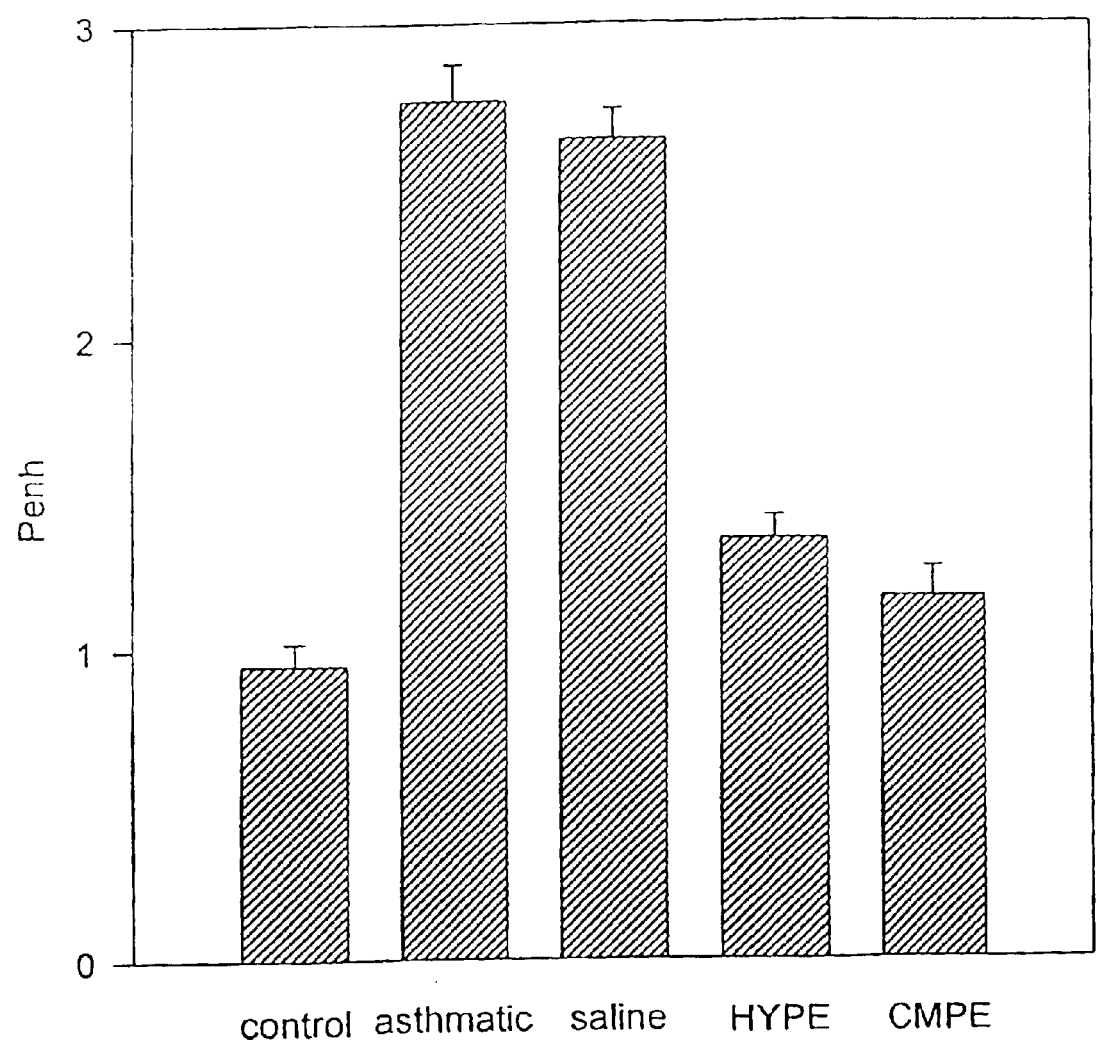
FIG. 4. Amelioration of Respiratory Function in Asthmatic Rats by Subcutaneous Administration of HYPE and CMPE FIG. 5 Amelioration of Respiratory Function in Asthmatic Rats by Aerosolic Administration of HYPE FIG. 6. Pathology of Rat Lungs with Chronic Asthma Treated by HYPE inhalation vs Dexamethasone FIG. 7. Reduction of Intestinal Damage Score by CMPE in Colitis—Type and Crohn's—Type Large and Small Bowel Pathology FIG. 8. Amelioration of Mucosal Damage in Crohn's—Type Small Bowel Disease FIG. 9. Reduction of Intestinal Permeation by CMPE in Colitis—Type and Crohn's—Type Large and Small Bowel Injury FIG. 10. Improvement of Disease Score by HYPE in Colitis FIG. 11. Improvement of Colon Length by HYPE in Colitis FIG. 12. Inhibition of Glial Cell $PGE_2$ Production by CMPE and HYPE FIG. 13. Inhibition of PC-12 Cell $PGE_2$ Production by CMPE and HEPE FIG. 14. Inhibition of Glial Cell Nitric Oxide Production by CMPE, HEPPE, and HYPE FIG. 15. Inhibition of Macrophage Nitric Oxide Production by HYPE FIG. 16. Inhibition of Phospholipase Release from Glial Cells by CMPE, HEPPE, and HYPE FIG. 17. Inhibition of PC-12 Cell Oleic Acid Release by CMPE FIG. 18. Inhibition of Macrophage Oleic Acid Release by CMPE FIG. 19. Inhibition of PC-12 Cell Dopamine Release by CMPE FIG. 20. Inhibition of PC-12 5-HETE Release by CMPE and HEPE FIG. 21. Inhibition of T-Cell Permeation Through Endothelial Monolayer by DEXPE and CMPE FIG. 22. Inhibition of Psoriatic Fibroblast Proliferation by CMPE FIG. 23. Inhibition of Smooth Muscle Cell Proliferation by HYPE FIG. 24. Inhibition of Stimulated Smooth Muscle Cell Proliferation by HYPE FIG. 25. Inhibition of Smooth Muscle Cell Proliferation by HEPPE FIG. 26. Inhibition of Oxidized LDL Uptake In Vivo by HYPE FIG. 27. Inhibition of LDL-Associated Phospholipase by CMPE, HEPPE, and HYPE FIG. 28. Protection of Endothelium by CMPE and DEXPE as Judged by Red Blood Cell Adhesion FIG. 29. Inhibition of Tumor Cell Invasion by HEPPE and HYPE FIG. 30. Inhibition of Hyaluronidase by HYPE FIG. 31. Inhibition of Collagenase by HYPE FIG. 32. Inhibition of Heparinase by CMPE and HYPE FIG. 33. Inhibition of Endothelial Cell Proliferation by HEPPE and CMPE FIG. 34. Protection of Cells From Oxidation Injury by CMPE As Judged by Arachidonic Acid Release FIG. 35. Protection of Cells From Oxidation Injury by CMPE as Judged by Sulfate Release FIG. 36. Inhibition of Copper Induced Oxidation of LDL by HYPE FIG. 37. Protection of Red Blood Cells to Irradiation and Storage Conditions by HEPPE and HYPE FIG. 38. Reduction of TNF-α Production in Whole Blood by HYPE FIG. 38a. Effect of PL-Conjugates on Expression of TNF FIG. 39. Reduction of TNF-α Production in Macrophages by HYPE FIG. 40. Suppression of Chemokine Production in Lung Endothelium by HYPE FIG. 41. Suppression of Chemokine Gene Expression by HYPE FIG. 41a. Effect of PL-Conjugates on Expression of IL-8

Treatment with PL-conjugates, dissolved in PBS, or the vehicle (control) was performed by S.C. injection (10 mg/100 g body weight) at 24 and 1 hour prior to challenge with OA (FIG. 4).

Experiment 6

Figure 5:
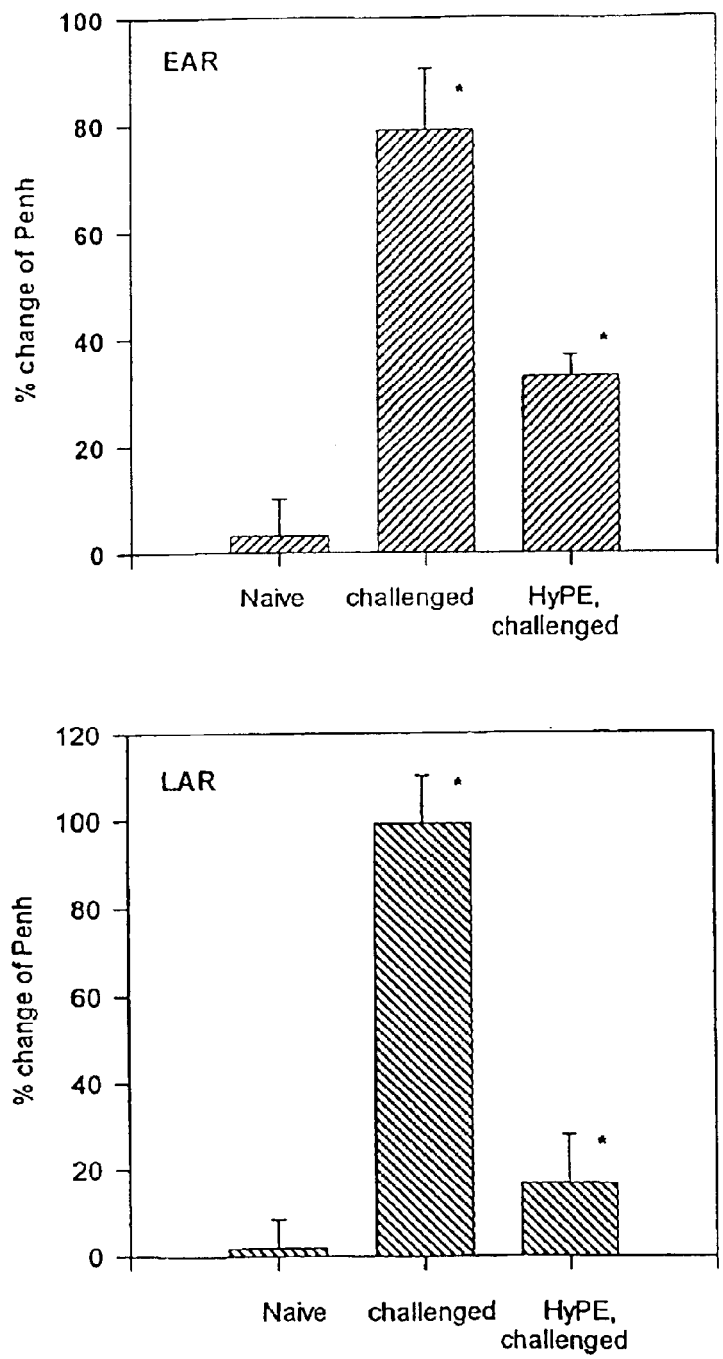

In each group, 5 rats in a 20 L cage, inhaled the aerosolic preparation of HYPE for 5 min, one day and 1 hour prior to challenge. Each datum is mean±SEM for 5 rats. *p<0.01. Penh, (pulmonary airflow obstruction in conscious rats) was determined using the method of Hamelmann, et al. Unrestrained conscious rats were placed in a whole-body plethysmograph (Buxco Electronics Inc., Troy, N.Y., USA) connected to a preamplifier (model MAX2270, Buxco Electronics). Analog signals from the amplifier are converted to a digital signal by an AD card (LPM-16 National Instruments Austin, Tex., USA). Calculations of the enhanced pause (Penh) of each breath are used as Bronchoconstriction measurements. Penh is the result of the formula: Penh=(PEF/PIF)×((Te-Tr)/Tr) where PEF=peak expiratory flow; PIF=peak inspiratory flow; Te=expiratory time; Tr=relaxation time [ibid.]. Each datum is mean±SEM for 5_rats. *,**p<0.005. The effect of the PL-conjugates on the asthmatic rats may be demonstrated by administering one of these agents prior to the ovalbumin-induced asthmatic attack. Significantly, PL-conjugates are effective in treating the asthma both when administered by parenteral (FIG. 4) and aerosol route (FIG. 5).

Experiment 7

Figure 6:
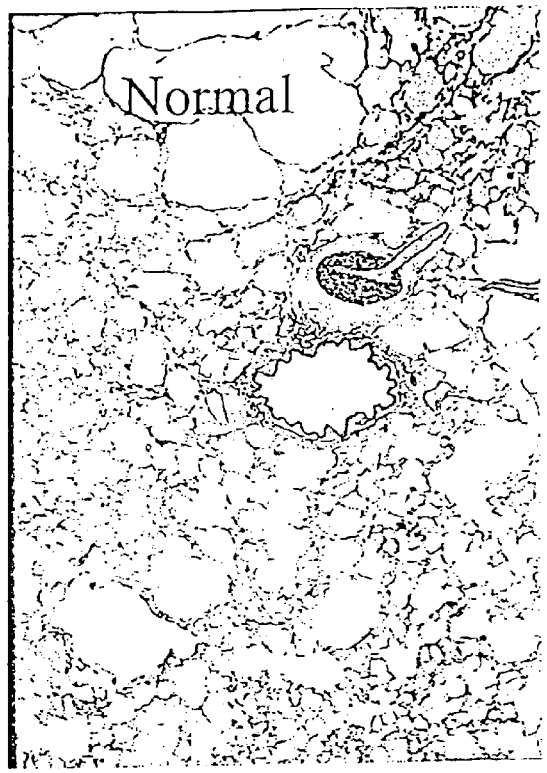
Figure 6:
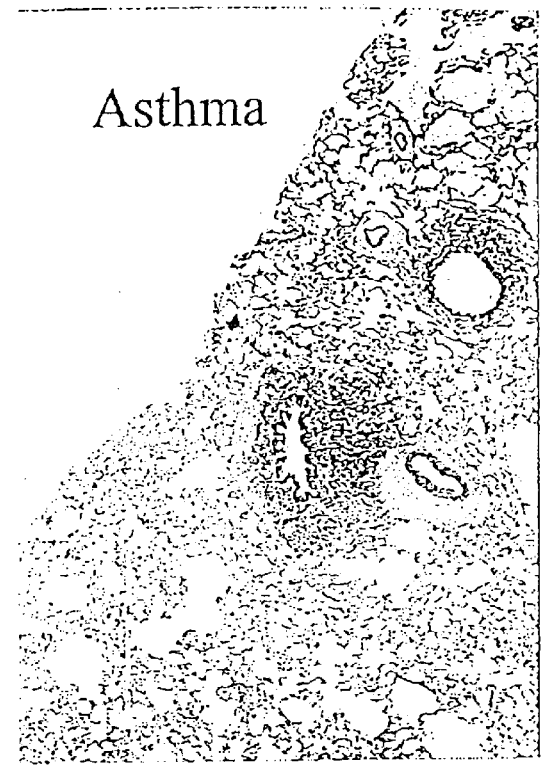
Figure 6:
Figure 6:

The in vivo effects of the PL-conjugates are demonstrated not only by their alleviation of the respiratory distress of sick animals but by histologic diagnosis as well (FIG. 6). Administration of PL-conjugates significantly reduces the physiological infiltrates of the airway lumen associated with asthmatic disease, and in this capacity are at least as effective as the standard steroid-based drug dexamethasone.

These experiments demonstrate that PL-conjugates may be used for the treatment of obstructive respiratory disease, alleviating airway narrowing by a plurality of mechanisms, including inhibition of contraction and reduction of airway obstructing infiltrates. Additional support for the utility of PL-conjugates in treating obstructive respiratory disease is provided by the results of Experiment 14, below, demonstrating inhibition of tracheal tissue $PGE_2$ and $TXB_2$ production by CMPE.

EXAMPLE 2

Colitis and Crohn's Disease

PL-conjugates are effective in the treatment of mucosal layer damage due to gastrointestinal tract disease. This is demonstrated in Experiments 8–11. Colitis and Crohn's disease are two examples of digestive tract disease in which the tissue barrier which lines the tract is damaged. One commonly accepted model of GI mucosal disease of this type is the damage to the physiological lining of the intestines produced in rodents which consume either high doses of the anti-inflammatory drug indomethasin (Crohn's disease), the toxin trinitrobenzene sulfonic acid (TNBS) (colitis), or the bowel irritant known as dextran sulfate sodium salt (DSS) (colitis). For experimental protocols see Materials and Methods.

Experiments 8 and 9

Figure 7:
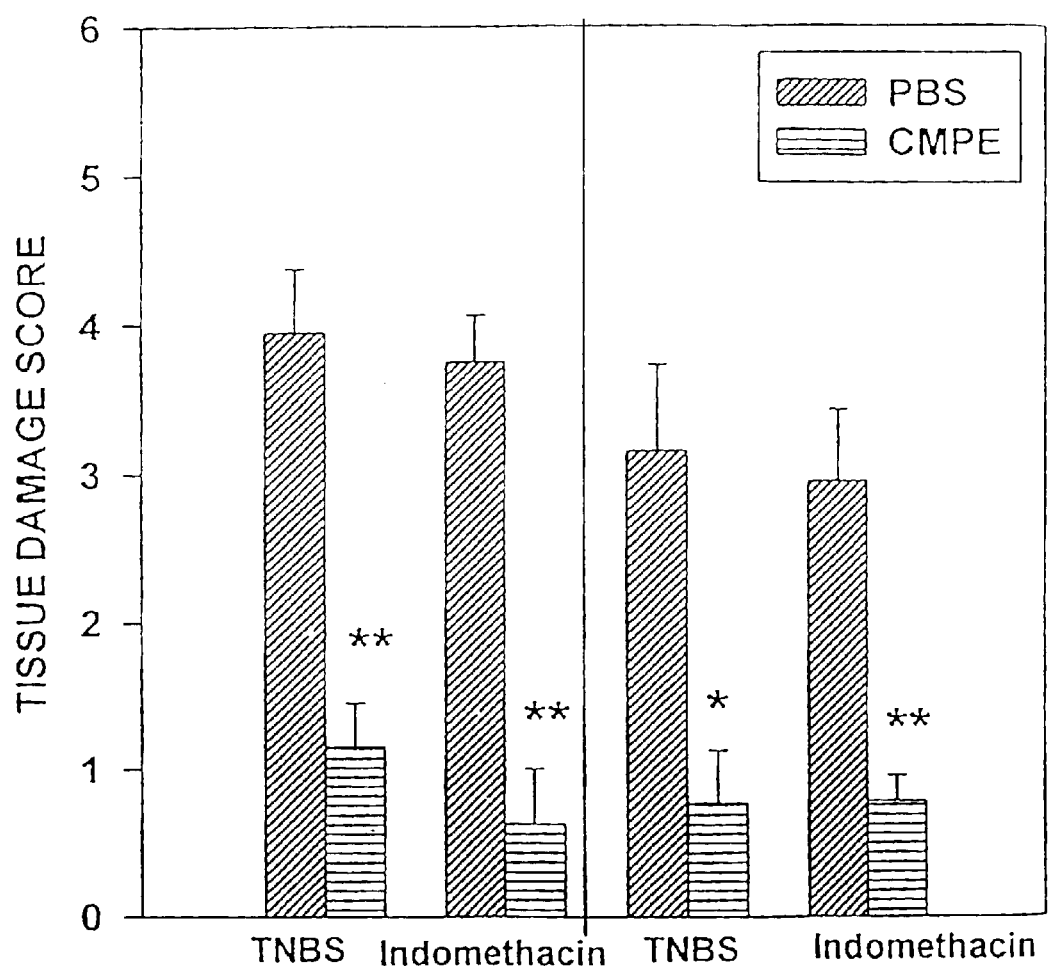
Figure 8:
Figure 8:
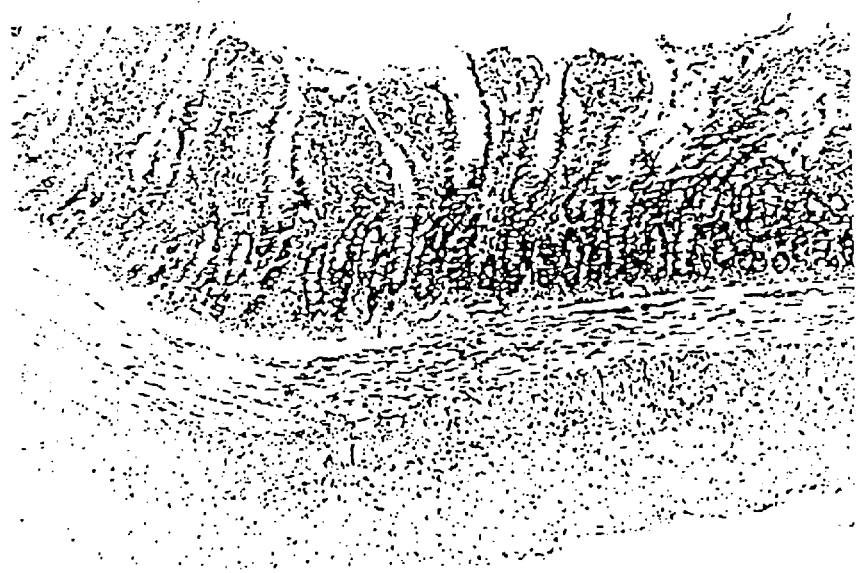

Rats with severe cases of intestinal bowel injury, as evidenced by the tissue damage score (FIG. 7) and histological diagnosis (FIG. 8), were significantly improved by administration of the PL-conjugate prior to the illness.

Experiment 10

Figure 9:
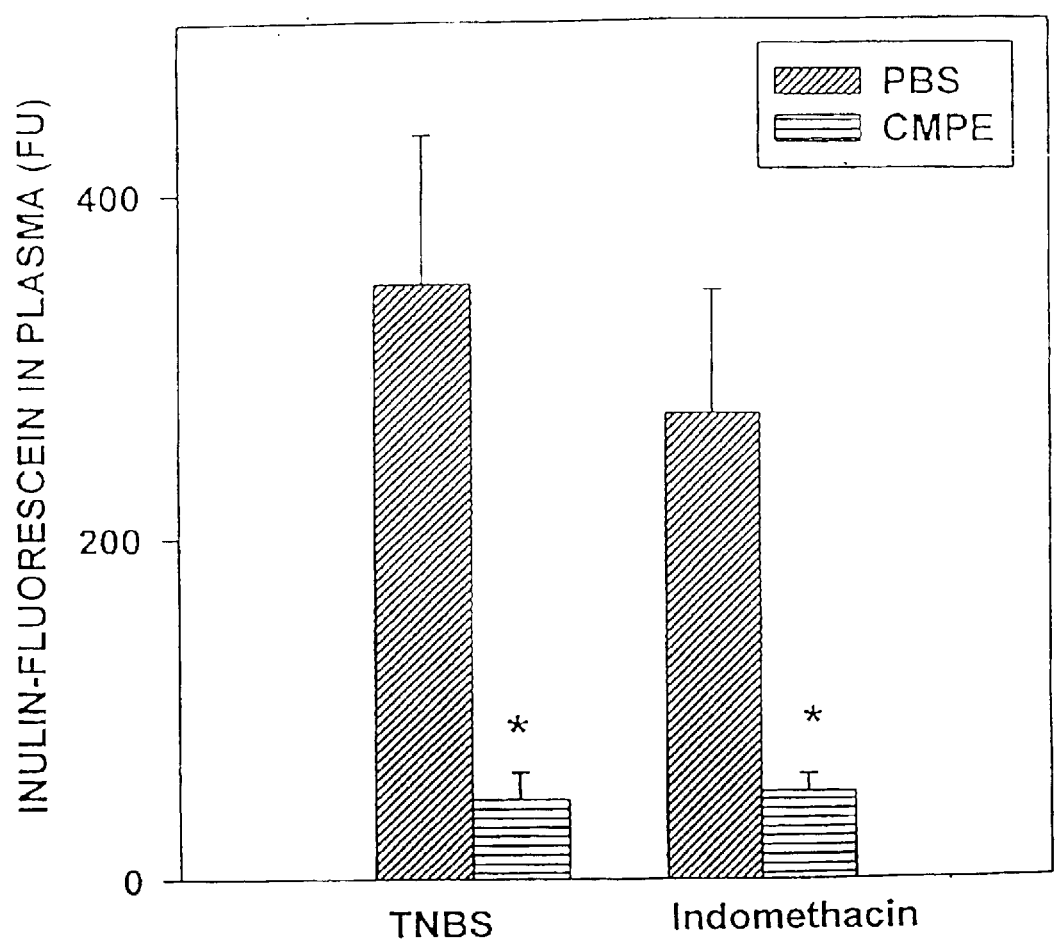

A similar sparing effect from drug or toxin inducing damage is seen not only on the histological level but functionally as well, evidenced by retention of the intestinal wall barrier to flourescent dye upon PL-conjugate treatment (FIG. 9). In addition, it was found that PL-CMC treatment considerably reduced the myeloperoxidase activity (MPO) in the colon of colitic rats who had survived. The respective MPO activity in the untreated and the PL-CMC treated groups was 19.1±2.6 AND 7.9±1.1 units/mg. Tissue (mean±SEM, n=6, p<0.01). In all the cases in which animals receive the drug, their illness is remarkably improved, as evidenced by the fact that most mice continued to live rather than die (Table 2 and Table 3).

TABLE 2

Reduced Mortality by CMPE in Colitis

| No. of dead rats / No. of rats in group treatment | | | % mortality treatment | |
|---|---|---|---|---|
| PBS | CMPE | | PBS | CMPE |
| 4/8 | 1/8 | | 50 | 12.5 |
| 4/10 | 0/10 | | 40 | 0 |
| 7/10 | 3/10 | | 70 | 30 |
| 5/8 | 1/8 | | 62 | 12.5 |
| 7/10 | 4/10 | | 70 | 40 |
| TOTAL 27/46 | 9/46 | MEAN | 58.4 | 19.0 |
| | | ±SEM | ±5.9 | ±7.1 |
| | | | | $P < 0.005$ |

TABLE 3

Indomethacin-Induced Small Intestinal Damage

| No. of dead rats / No. of rats in group treatment | | | % mortality treatment | |
|---|---|---|---|---|
| PBS | CMPE | | PBS | CMPE |
| 2/5 | 1/5 | | 40 | 20 |
| 2/5 | 1/5 | | 40 | 20 |
| 3/5 | 0/5 | | 60 | 0 |
| TOTAL 7/15 | 2/15 | MEAN | 46.7 | 13.3 |
| | | ±SEM | ±6.7 | ±6.7 |
| | | | | $P < 0.025$ |

Experiment 11

Figure 10:
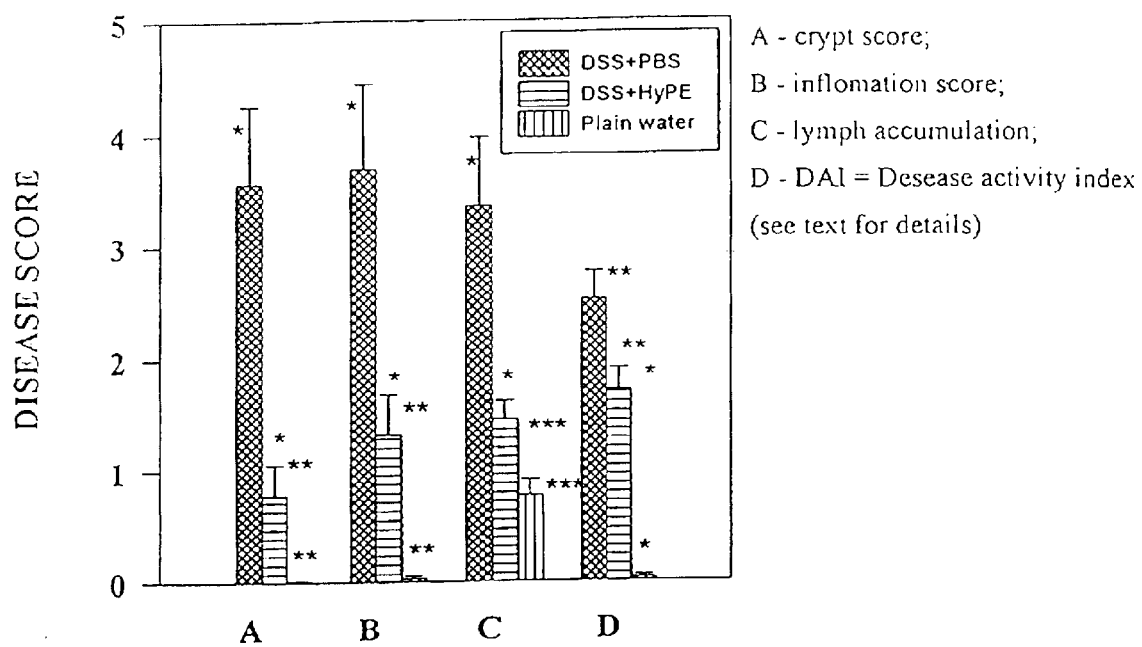
Figure 11:
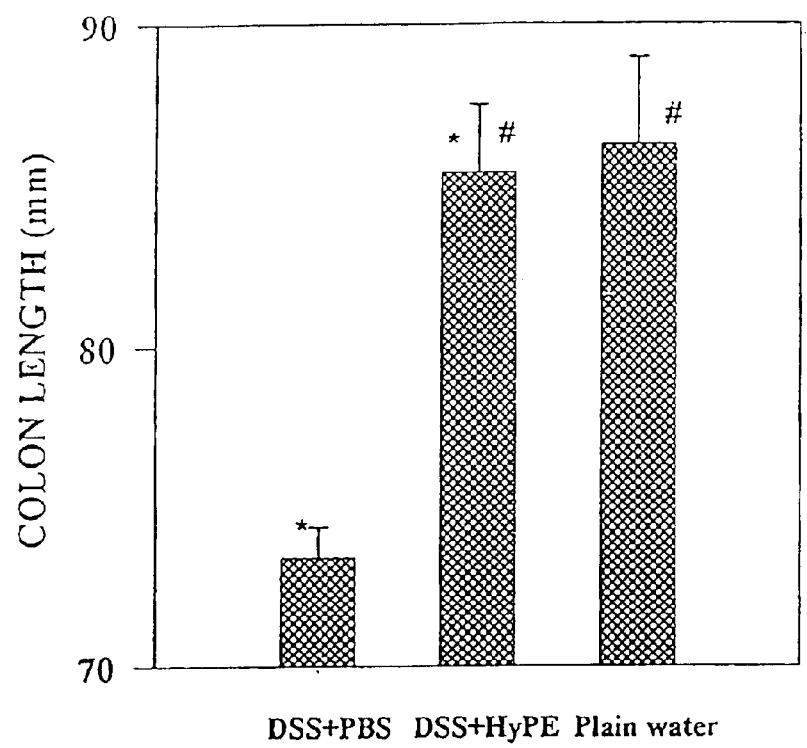

In dextran sulfate-induced colitis mortality was unchanged (3 out of 12 mice died in each case) but other parameters of disease activity were significantly improved, as evidenced by overall disease score (FIG. 10) and preservation of colon length (FIG. 11). These disease-sparing effects of the administered PL-conjugates are manifested whether the drug is provided by the parenteral or inhalation route.

These experiments demonstrate that PL-conjugates are effective therapy in the treatment of colitis and Crohn's disease, based upon the ability to preserve the mucosal barrier of the afflicted organ, through effects on both structural and functional features of the tissue.

EXAMPLE 3

Central Nervous System Insult

The PL-conjugates are effective as neurotoxic agents, preventing tissue damage following physiological insult to the central nervous system. This is demonstrated in experiments 12–22. Ischemic stroke, trauma, infection, cancer metastases, and degenerative disease exemplify physiological insults in which brain tissue injury may be severe and irreversible. Tissue injury typically evokes a myriad of physiological responses to stress, which in the central nervous system take the form of chemical substances released by support tissue. However, an excess of one, or more, of these potentially neurotoxic 'wound' chemicals may serve to further disrupt the healing process and contribute to the brain tissue damage. Commonly accepted models for assessing the neuroprotective ability of a new drug employ preparations of brain matrix cells (e.g., glial cells), cell lines derived from brain cells (e.g., P-12 cells), and migratory blood cells (macrophages and lymphocytes) which are typically recruited to the sites of damaged brain tissue. Tissue injury in the CNS is frequently compounded by local disruption of the blood brain barrier and subsequent passage of migratory blood cells which may exacerbate the effects of the original insult and lead to extension of the tissue damage. Cell migration through the intact and disrupted blood brain barrier is modeled in situ, employing measurement of T cell movements through endothelial cell layers.

In response to substances associated with stress and impending injury, such as the immunogen LPS, the cytokine TNF-α the neurotoxin pardaxin, matrix cells of the central nervous system activate a myriad of wound response substances, such as $PGE_2$, endothelin, oxygen radicals, thromboxane, dopamine, nitric oxide, 5-HETE, and $PLA_2$. When expressed in excess, these substances are either themselves neurotoxic or indicative of cotemporal neurotoxicity, thus their suppression is a frequently chosen target for developing neuroprotective drugs.

Experiments 12–14 demonstrate PL-conjugate inhibition of prostaglandin ($PGE_2$) release.

Experiment 12

Figure 12:
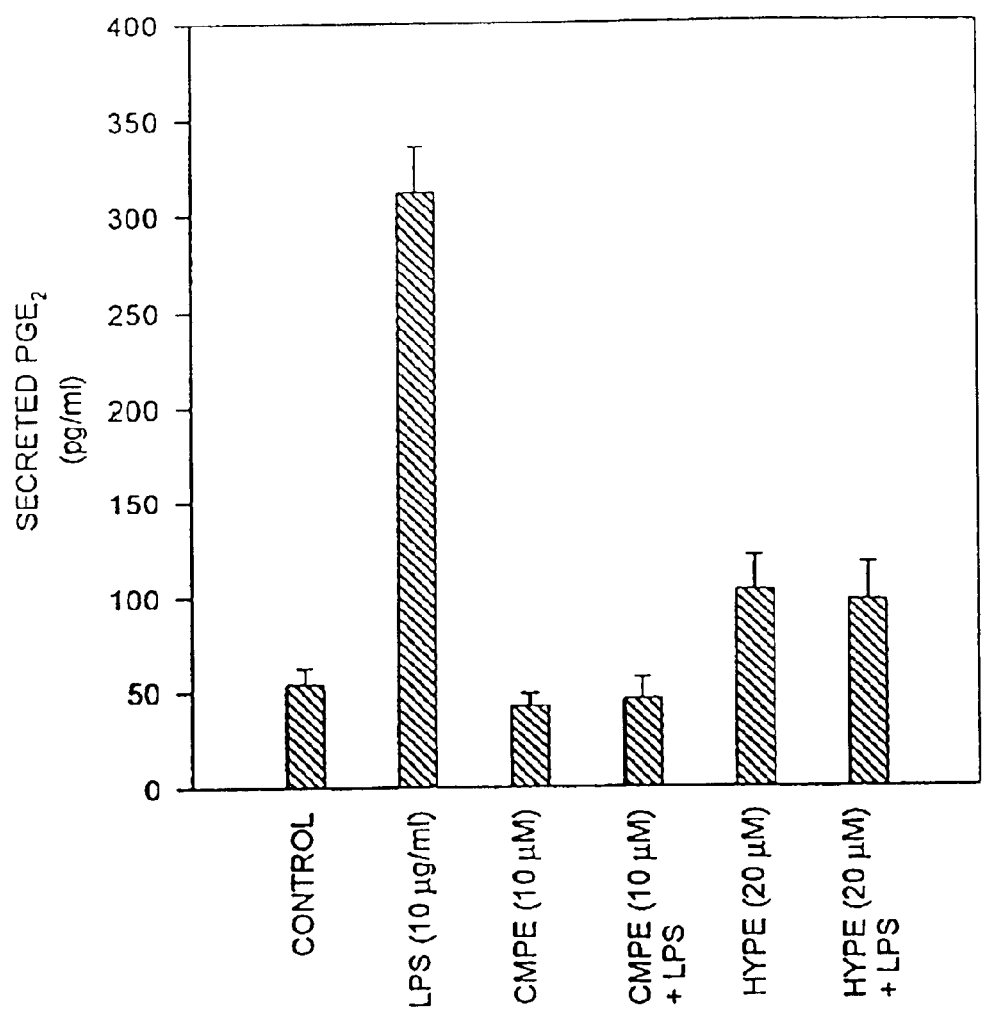

Glial cell media was replaced with fresh media prior to all experiments, supplemented with 10 μg/ml LPS. PL-conjugates were added 30 minutes before exposure to LPS. The tissue cultures were further incubated at 37° C. for 24 h. Then the medium was collected and the cells were incubated in fresh medium containing LPS and PL-conjugate. After an additional 24 h, supernatants were taken for determination of $PGE_2$ content by ELISA (FIG. 12).

Experiment 13

Figure 13:
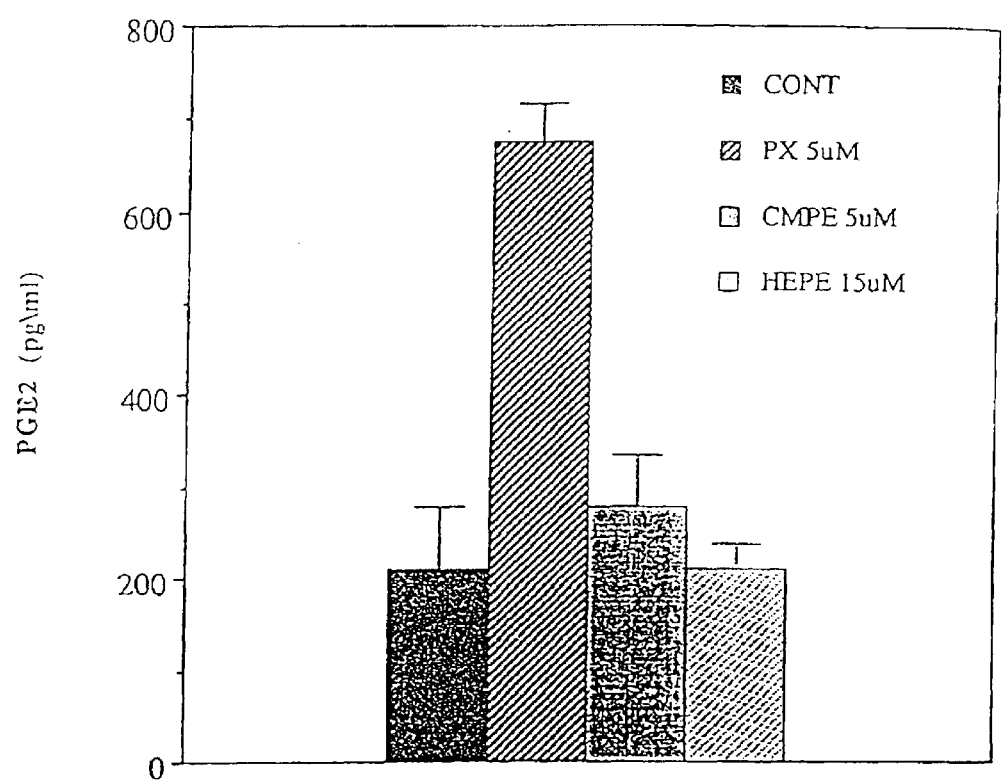

For PC-12 cells, following incubation with the indicated PL-conjugate, the cells were washed then stimulated with pardaxin (PX) for 30 minutes and the amount of $PGE_2$ released to the medium was determined by ELISA (FIG. 13).

Experiment 14

Guinea pig tracheal rings were incubated in test tubes with or without CMPE for 30 minutes prior to stimulation. The medium was collected after 30 minutes and $PGE_2$ and $TXB_2$ were determined by radioimmunoassay (Table 4). (n.d.=below limit of detection.)

TABLE 4

Inhibition of Tracheal Tissue $PGE_2$ and $TBX_2$ Production by CMPE

| STIMULANT | CMPE | $PGE_2$ (ng/ml) | $TXB_2$ (ng/ml) |
|---|---|---|---|
| Histamine (40 μM) | — | 5.1 | 5.6 |
| Histamine (40 μM) | 10 μM | n.d. | 1.75 |

Experiments 15 and 16

Figure 14:
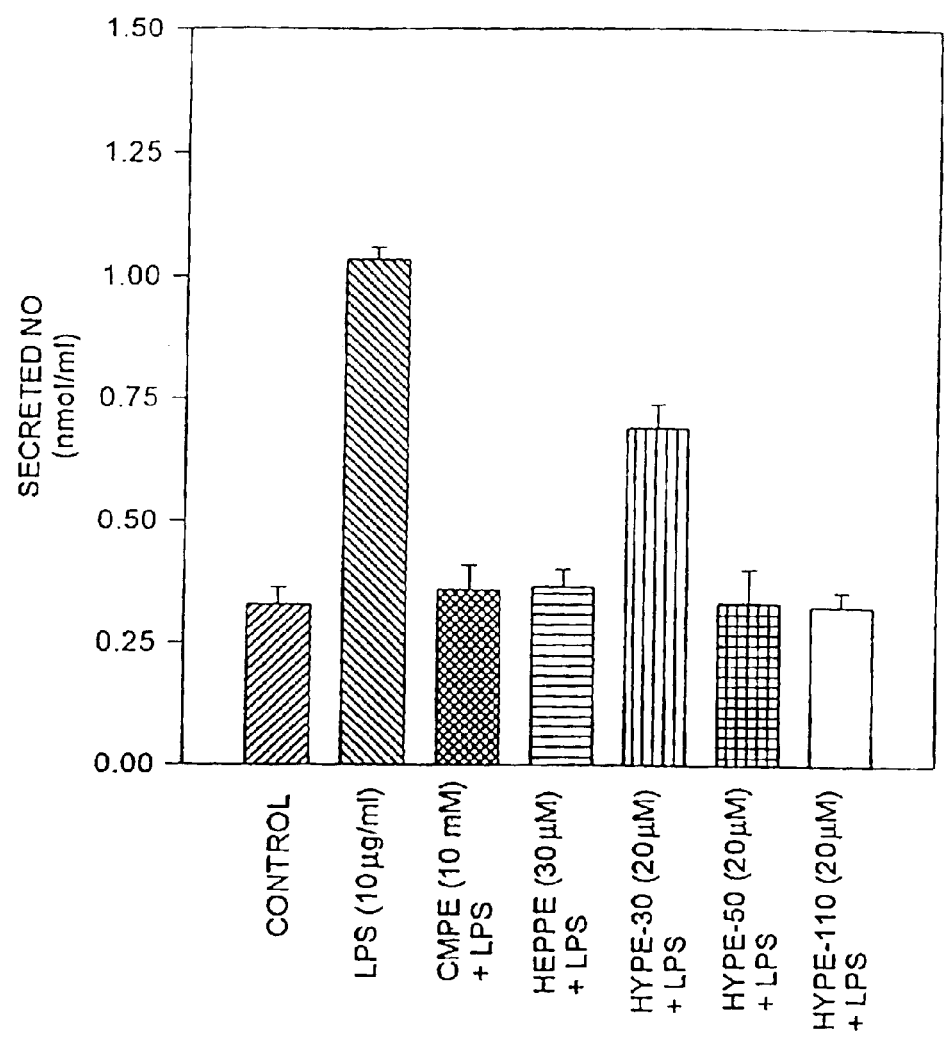
Figure 15:
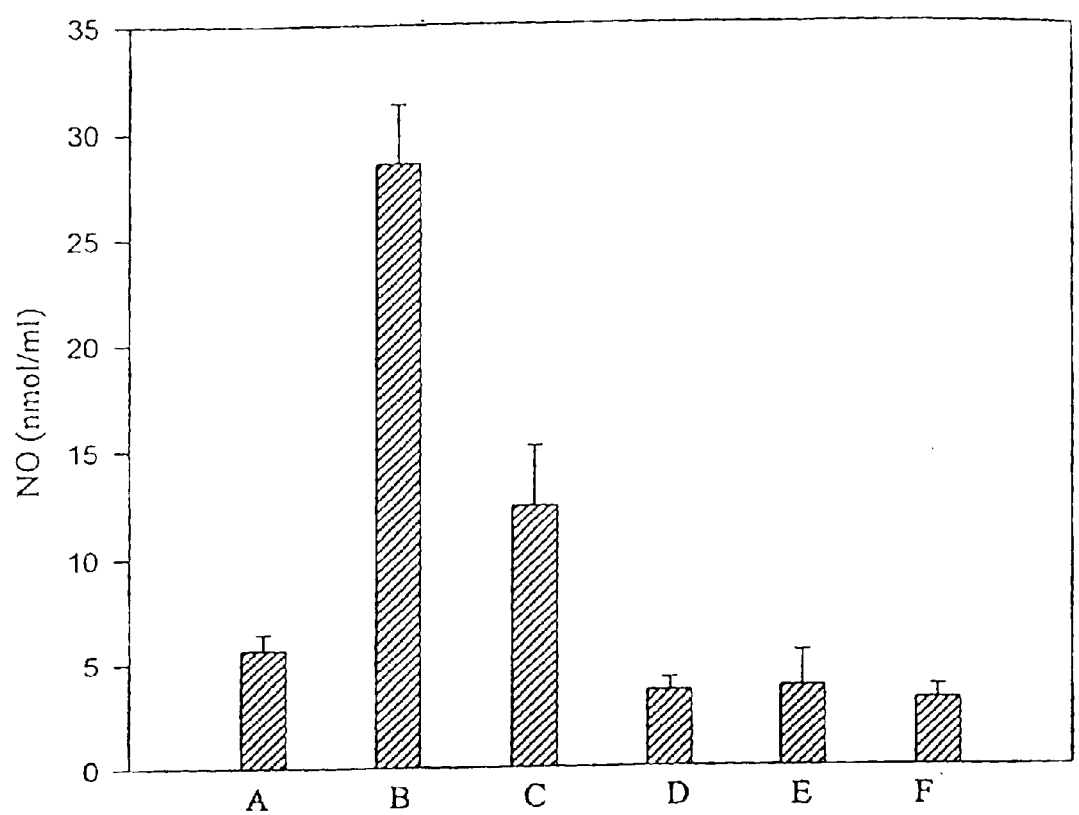

For demonstrating PL-conjugate suppression of nitric oxide production. Glial cell media was replaced with fresh media, supplemented with 10 μg/ml LPS. PL-conjugates were added 30 minutes before exposure to LPS. The tissue cultures were further incubated at 37° C. for 24–48 h. Supernatants were taken after 24 h for determination of NO by colorimetric measurement using the Griess reagent (FIG. 14). Alternately, primary mouse peritoneal macrophages were treated with PL-conjugates at the indicated concentration for 30 minutes (FIG. 15). Then LPS (1 μg/ml) was added to the culture either directly or after washing of the PL-conjugates. Nitric oxide was determined by the Griess calorimetric method.

Experiment 17

Figure 16:
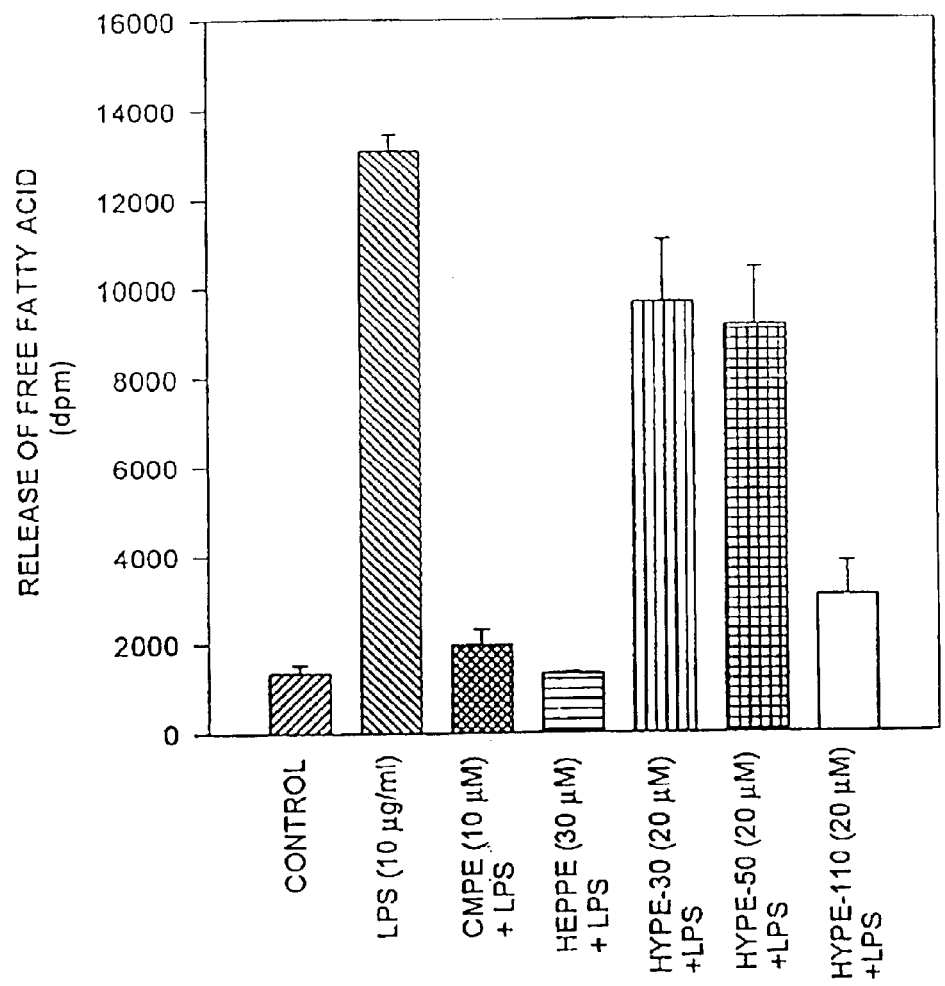

For demonstration of PL-conjugate inhibition of soluble phospholipase $A_2$ (sPLA$_2$) release from glial cells (FIG. 16). Prior to all experiments, glial cell media was replaced with fresh media, supplemented with 10 µg/ml LPS. PL-conjugates were added 30 minutes before exposure to LPS. The tissue cultures were further incubated at 37° C. for 24–48 h. Culture medium samples (after 24 h) were taken for determination of PLA$_2$ activity versus *E. coli* substrate.

Experiments 18 and 19

Figure 17:
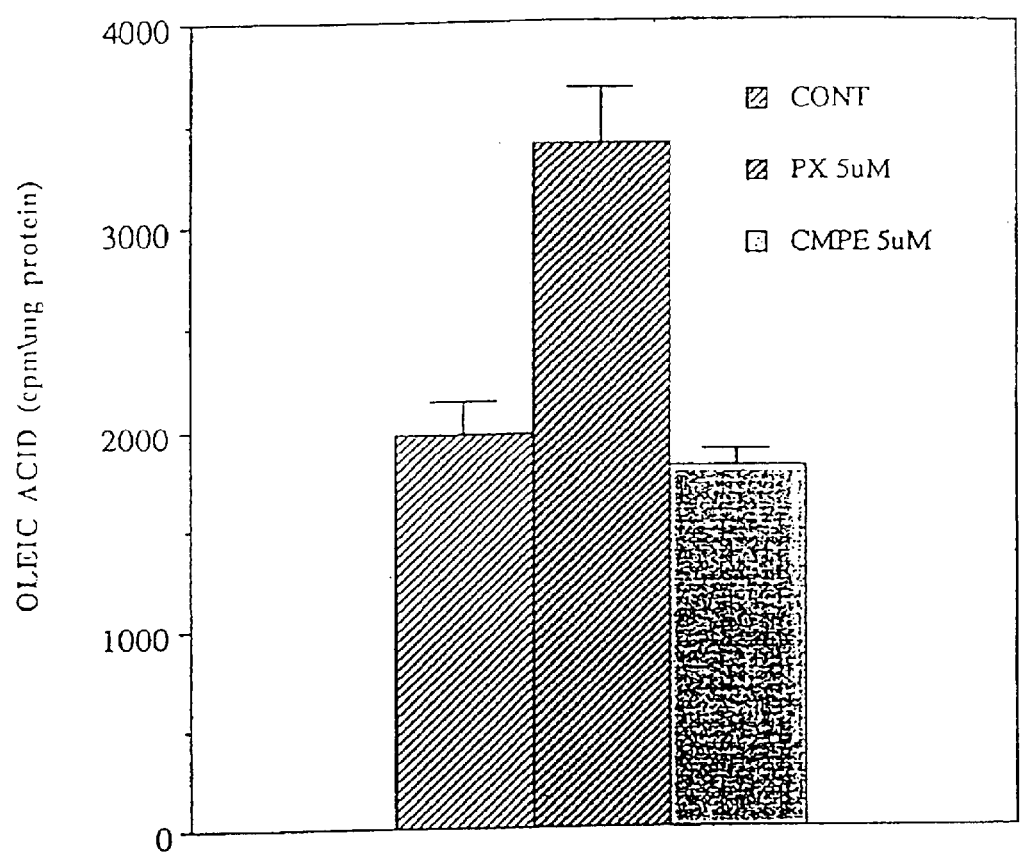
Figure 18:
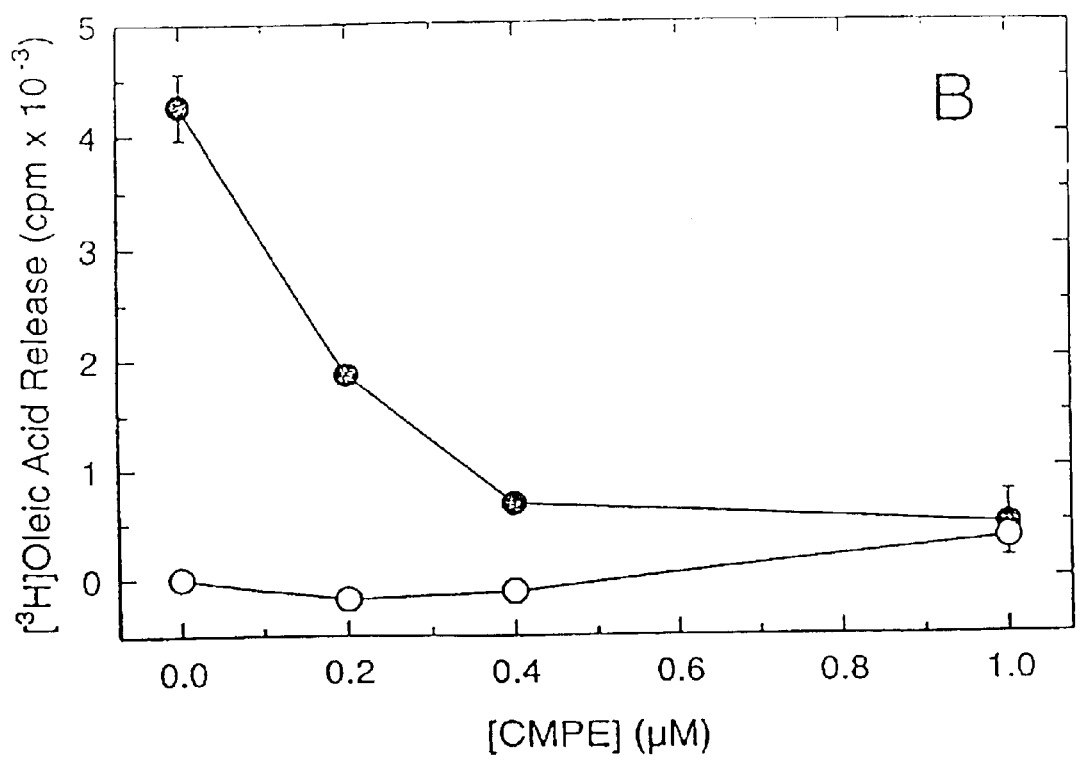

To demonstrate the ability of PL-conjugates to suppress phospholipase activation, measured as oleic acid release. For brain tissue, PC12 cells were metabolically labeled with $^3$H-arachidonic acid (ArAr) or $^3$H-oleic acid for at least 6 h, then washed and incubated with PL-conjugate as indicated for 30 minutes. The cells were then washed, stimulated with pardaxin (PX) for 30 minutes and the amount of $^3$H-fatty acid released to the medium was determined in a scintillation counter (FIG. 17). For release of oleic acid from macrophages (FIG. 18), murine P388D$_1$ cells were labeled and assayed in the presence (●) and absence (○) of LPS following pre-treatment with varying concentrations of a PL-conjugate as described in Materials and Methods below.

Experiment 20

Figure 19:
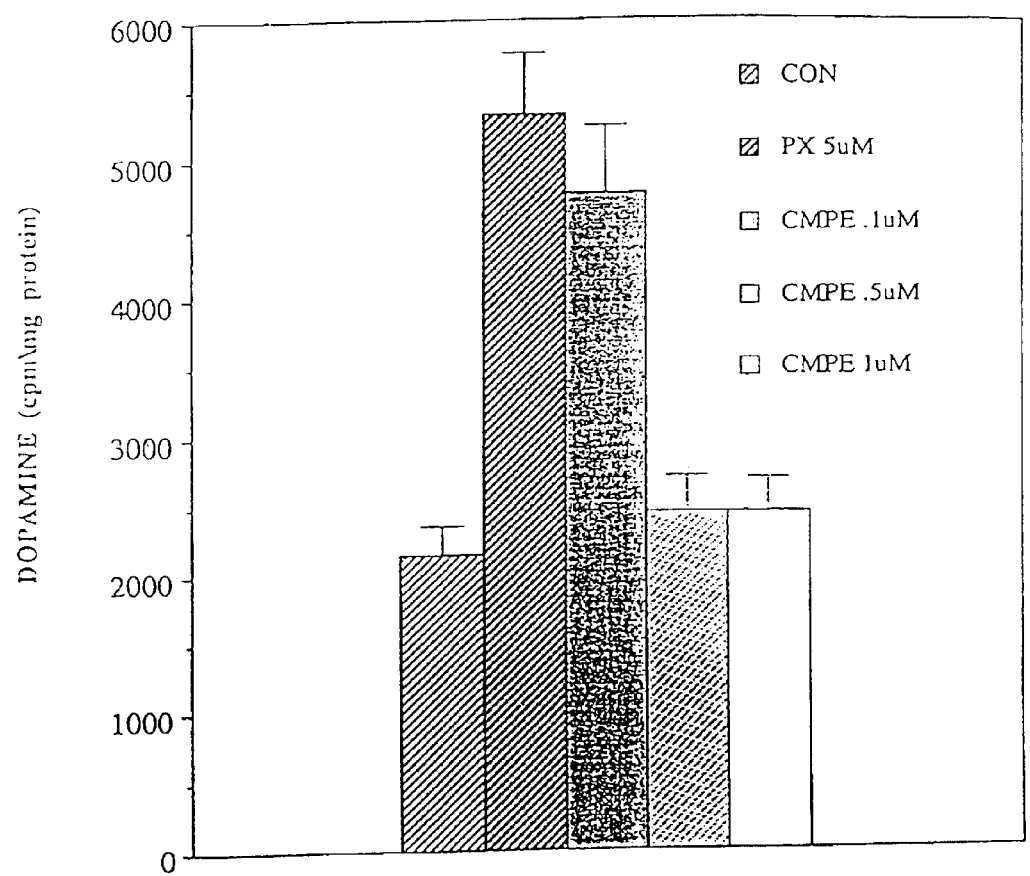

To demonstrates the ability of PL-conjugates to suppress dopamine release. PC12 cells (at confluence) were loaded with radioactive dopamine (DOPA) for 4 h, then washed (in the presence of antioxidant). The cells were then incubated with the indicated PL-conjugate for 30 min, then washed and stimulated with PX for 15 min. The amount of labeled DOPA released to the culture medium was determined in a scintillation counter (FIG. 19).

Experiment 21

Figure 20:
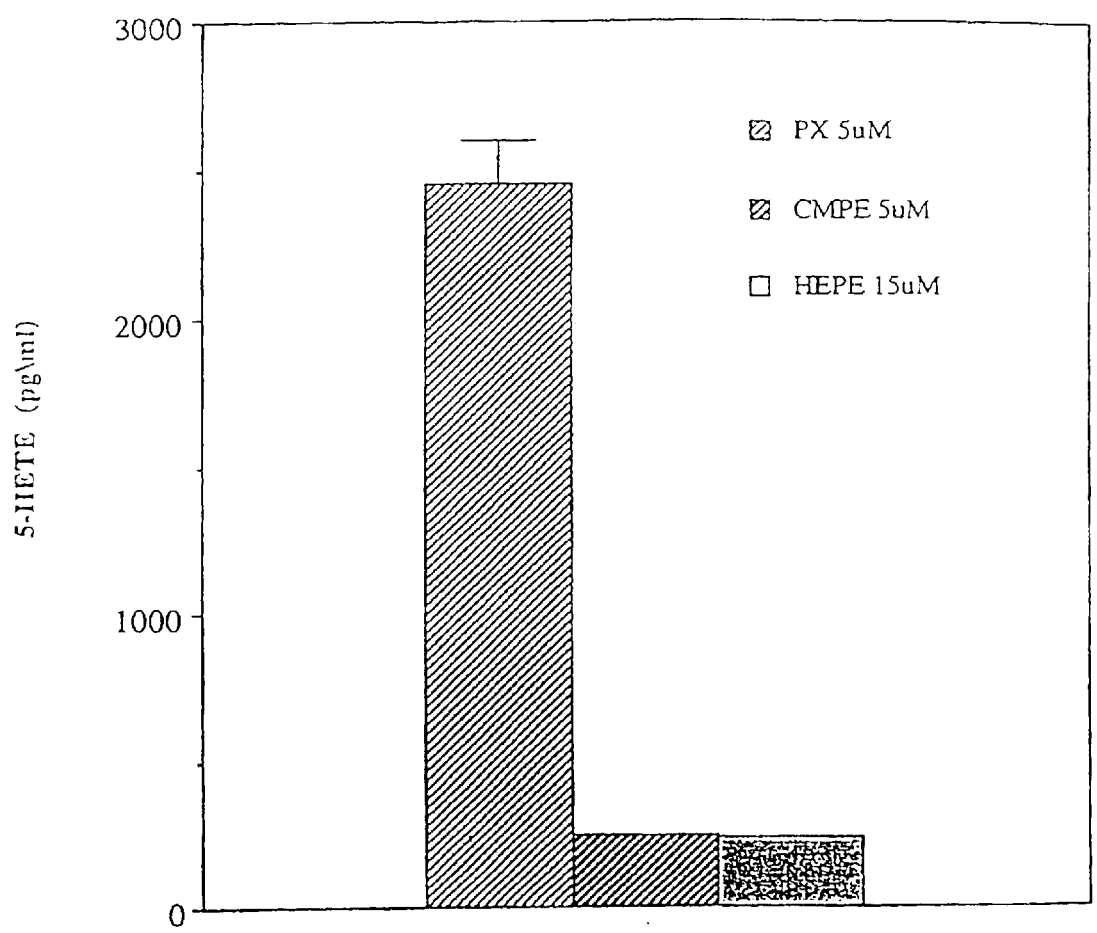

For demonstrating PL-conjugate suppression of 5-HETE release, PC-12 cells, under identical conditions to experiment 23, are incubated with the indicated PL-conjugate, followed by PX stimulation. The amount of 5-HETE released was determined by ELISA (FIG. 20).

Experiment 22

Figure 21:
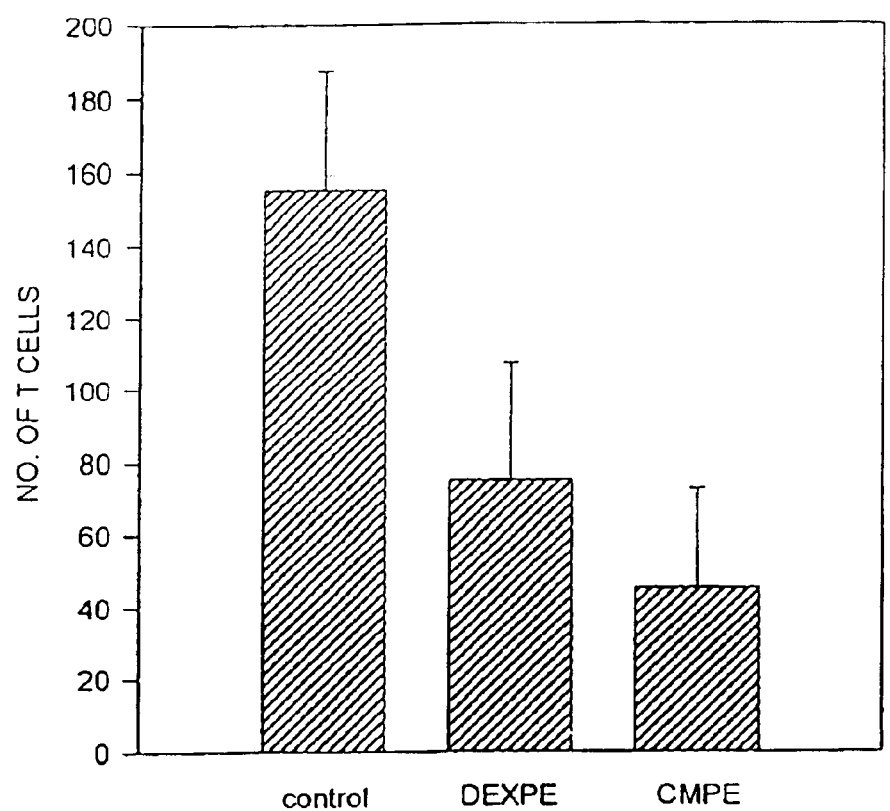

To demonstrate the potency of PL-conjugates to inhibit cell permeation through endothelial cell barrier. Using the T cell transendothelial migration assay (FIG. 21) primary pig brain endothelial cells (PBEC) were plated onto collagen coated 3.0 to the migration assay. Human peripheral blood T cells were prepared as described in Cabanas and Hogg (1993, PNAS 90: 5838–5842). The T cells were maintained in recombinant human IL-2 for up to 12 days prior to use. Approximately $1\times10^5$T cells were added to the upper chamber of the Transwells above the confluent PBEC monolayer and incubated at 37° C. for 5 h. Compounds for testing were also added to the PBEC monolayer at the same time as the T cells. Electrical resistance values were measured over this period at hourly intervals. At 5 hours the Transwells were briefly rinsed in warm medium and fixed in paraformaldeyde. The number of T cells which had migrated to the underside of the filter (i.e., through the PBEC monolayer) was counted as described in the report.

These experiments demonstrate that PL-conjugates are potent neuroprotective agents and useful when administered as therapy for the treatment of brain injury in settings such as stroke, tumor, trauma, infection and degenerative disease. Additional support for the efficacy of administering PL-conjugates as neuroprotective agents is found in the results of Experiments 57–58, below, demonstrating the efficacy of administering PL-conjugates for the treatment of stenosis/reperfusion injury.

EXAMPLE 4

Multiple Sclerosis

PL-conjugates are effective therapy for multiple sclerosis. This is demonstrated in experiments 23–24 below. Multiple sclerosis is a disease of white tissue in the central nervous system, marked by loss of neurological function. The commonly accepted animal model for this disease is experimental allergic encephalitis (EAE) which may be induced in rodents by subcutaneous sensitization to antigens of the nervous system, such as myelin basic protein. Clinical parameters are expressed by paralysis progressing from the rear limbs to the front limbs.

Experiments 23–24

To demonstrate that rats exposed to EAE-inducing agents are far less likely to develop the paralytic disease when treated concurrently with PL-conjugate administration. Both experiments employed groups of rats in which EAE had been induced by S.C. paw injection of 5 mg mouse spinal cord homogenate emulsified in 0.1 ml of CFA (1:1 in PBS buffer) enriched with inactivated mycobacterium tuberculosis 0.4 mg/ml, followed by tail vein injection of 200 ng in 0.2 ml of bordetella pertussis toxin 48 hours later. (see 'Materials and Methods' for scoring of disease severity).

In experiment 23, one group of rats received 20 mg CMPE every other day for two weeks starting from the first day of the experiment. The other group received the same dose, but only from the seventh day of the experiment (after the T-cells are activated). At the same time the respective control groups were injected with saline (Table 5).

TABLE 5

Amelioration of EAE (Multiple Sclerosis) by CMPE

|  | Incidence[1] | Severity score[2] | Duration[3] (days) |
|---|---|---|---|
| EAE control | 75% (6/8) | 3.5 ± 2.0 | 3.8 ± 2.6 |
| EAE + 20 mg/rat CMPE Day 1 | 38% (3/8) | 1.3 ± 1.7 | 2.1 ± 2.5 |
| EAE + 20 mg/rat CMPE Day 7 | 30% (3/10) | 1.1 ± 1.7 | 1.6 ± 2.5 |

In experiment 24, one group received 2 mg of CMPE every other day from Day 1 through the 14 days of the experiment. The other group of rats received 20 mg every other day from day 7, through the 14 days of the experiment (table 6).

TABLE 6

Amelioration of EAE (Multiple Sclerosis) by CMPE, Low vs High Dose

|  | Incidence[1] | Severity score[2] | Duration[3] (days) |
|---|---|---|---|
| EAE control | 70% (7/10) | 2.9 ± 1.4 | 3.7 ± 1.0 |
| EAE + 20 mg/rat CMPE Day 1 | 20% (2/10) | 0.5 ± 1.1 | 2.7 ± 1.4 |

Both experiments show that therapy with PL-conjugates results in a less severe course of disease and more complete recovery of motor function, as judged by the percentage of rats showing paralysis (incidence[1]), the degree of paralysis and progression towards the front limbs (severity score[2]), and the duration of paralysis until recovery (duration[3]). In addition, the results presented in table 6 demonstrate that the therapeutic effect of the PL-conjugates is dose-dependent.

Additional support for the efficacy of PL-conjugates in multiple sclerosis may be found in Experiments 15, 17, and 22, above, wherein the neuroprotective effect of the PL-conjugates is demonstrated.

EXAMPLE 5

Contact Dermatitis & Psoriasis

PL-conjugates are effective in the treatment cutaneous hypersensitivity reactions and psoriasis. This is demonstrated in experiments 25–29. Skin hypersensitivity reactions may occur in response to virtually any material and may present in both acute and chronic forms. Systemic sensitization to an antigen followed by its local application is a widely-accepted system for invoking the delayed type hypersensitivity response attributed to the mechanism of contact dermatitis. Psoriasis is a common form of dermatitis marked by plaque-like formations evident often prominent on extensor surfaces and, as a hyperproliferative disorder of epithelial cells, drug therapies are typically examined in cell cultures obtained from sufferers of the condition.

Experiments 25–28

To show that treatment of the animals afflicted with a hypersensitivity reaction readily respond to the administration of PL-conjugates, whether applied systemically (table 7), subcutaneously (table 8), or topically (tables 9–10), as both prophylactic and acute therapy.

Three modes of administration were performed: 1) The PL-conjugate in saline was injected intraperitoneally daily beginning day 0 until day 6 (table 7); 2) The PL-conjugate in saline was injected subcutaneously into the ear (adjacent to the challenged area) in two injections, either two h before application of oxalozone to the ear or 1 h after application of oxalozone to the ear (table 8); 3) EtOH:H$_2$O 1:1 was applied topically to both ears on top of the challenged area daily beginning day 0 until day 6 (table 9); 4) the PL-conjugate was applied topically only to the right ear for 5 times 4–6 hours following the challenge (table 10) using either 20 µL of 0.1% DEXPE in 50% EtOH or 20 µl of Dermovat (steroid ointment). In all experiments control Group A (late sensitized only) was treated by topical application of oxalozone to both sides of the ear 24 hours before measuring its swelling. Group B (fully sensitized+saline or EtOH 50% was treated by topical application of oxalozone to the shaved stomach and then on day 6 by topical application of oxalozone to both sides of the ear. Swelling was measured in 0.1 mm by subtracting normal ear width of each individual mouse from the width after treatment. Percent inhibition was calculated by the net swelling of the PL-conjugate-treated ear (over that of the control group A), divided by the net swelling of the fully sensitized ear. Significantly, although the topical administration of the drugs was unilateral in both cases, the steroid affected both ears, while the topically applied PL-conjugate affected only the area to which it was applied, indicative of a lack of systemic administration in this context.

TABLE 7

Attenuation of Dermal DTH Response by CMPE - Intraperitoneal Administration

| Group | Treatment | No. of Mice | Swelling after sensitization – Swelling of normal ear (0.1 mm) Mean ± S.D. (n = 12) | Percent inhibition |
|---|---|---|---|---|
| A | Control (late sensitized only) | 6 | 1.8 ± 1.0 | — |
| B | Fully sensitized + saline | 6 | 18.5 ± 0.97 | — |
| C | Fully sensitized + CMC 40 mg (0.4 µmol)/kg | 6 | 19.8 ± 1.13 | — |
| D | Fully sensitized + CMPE 40 mg (0.4 µmol)/kg | 6 | 7.9 ± 1.37 | 66 |
| E | Fully sensitized + betamethasone 5 mg (15 µmol)/kg | 6 | 6.5 ± 1.35 | 74 |

TABLE 8

Attentuation of Dermal DTH Response by CMPE - Subcutaneous Administration

| Group | Treatment | No. of Mice | Swelling after sensitization – Swelling of normal ear (0.1 mm) Mean ± S.D. (n = 12) | Percent inhibition |
|---|---|---|---|---|
| A | Control (late sensitized only) | 5 | 4.1 ± 0.82 | — |
| B | Fully sensitized + saline | 5 | 18.3 ± 0.82 | — |
| C | Fully sensitized + CMC (carrier polymer only) 40 mg (0.4 µmol)/kg | 5 | 13.5 ± 2.17 | 35 |
| D | Fully sensitized + CMPE 40 mg (0.4 µmol)/kg | 5 | 5.9 ± 1.52 | 87 |
| E | Fully sensitized + betamethasone 1 mg (3 µmol)/kg | 5 | 8.1 ± 1.19 | 72 |

TABLE 9

Attentuation of Dermal DTH Response by DEXPE - Topical Administration

| Group | Treatment | No. of Mice | Swelling after sensitization – Swelling of normal ear (0.1 mm) Mean ± S.D. (n = 12) | Percent inhibition |
|---|---|---|---|---|
| A | Control (late sensitized only) | 5 | 1.5 ± 0.70 | — |
| B | Fully sensitized + saline | 5 | 24.3 ± 1.56 | — |
| C | Fully sensitized + DEX (5) (carrier polymer only) (0.5 µmol)/kg | 5 | 24.4 ± 2.4 | — |
| D | Fully sensitized + DEXPE (5) (0.5 µmol)/kg | 5 | 12.17 ± 1.52 | 53 |

TABLE 9-continued

Attentuation of Dermal DTH Response
by DEXPE - Topical Administration

| Group | Treatment | No. of Mice | Swelling after sensitization − Swelling of normal ear (0.1 mm) Mean ± S.D. (n = 12) | Percent inhibition |
|---|---|---|---|---|
| E | Fully sensitized + betamethasone (3 μmol)/kg | 5 | 10.6 ± 0.84 | 60 |

TABLE 10

Attentuation of Dermal DTH Response by DEXPE - Unilateral Topical Administration vs Steroid Preparation

| Group | Treatment | No. of mice | Swelling after sensitization-Swelling of normal ear (0.1 mm) Mean ± S.D. (n = 10) | | | Percent inhibition | |
|---|---|---|---|---|---|---|---|
| | | | Left ear | Both ears | Right ear | Left ear | Right ear |
| A | Control (late sensitized only) | 10 | | 1.0 ± 2.0 | | — | — |
| B | Fully sensitized + vehicle | 10 | | 23.0 ± 4.0 | | — | — |
| C | Fully sensitized + DEXPE (5) only on right ear (swelling of right ear) | 7 | 20.0 ± 1.0 | | 11.0 ± 1.0 | 14 | 46 |
| D | Fully sensitized + Dermovat only on right ear (swelling of right ear) | 7 | 7.0 ± 1.0 | | 7.0 ± 1.0 | 63 | 63 |

Experiment 29

Figure 22:
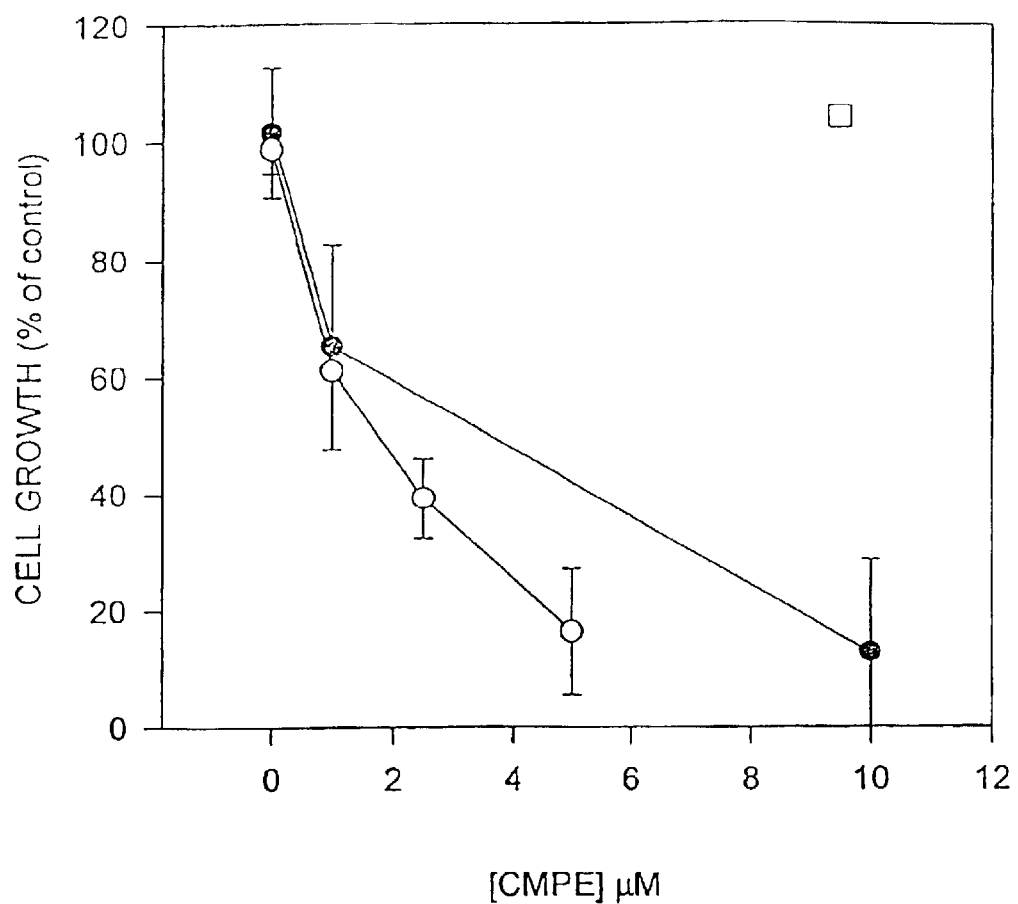

To show that PL-conjugates effectively inhibit the proliferation of cultured psoriatic skin fibroblasts and Swiss 3T3 cells. Fibroblasts of human psoriatic skin cells (dermis), (●) or Swiss 3T3 cells (○) were treated with CMPE at the indicated concentration for three days, after which the cells were counted (FIG. 22). The cell number of the control, untreated group at the end of the three day incubation was taken as 100%. For comparison, carboxymethylcellulose was tested alone (□).

These experiments demonstrate that PL-conjugates are effective remedies for the management of various forms of dermititis including skin hypersensitivity reactions and psoriasis.

EXAMPLE 6

Cardiovascular Disease

PL-conjugates are effective therapy for ischemic vascular disease, atherosclerosis, and reperfusion injury. This is demonstrated in experiments 30–36.

A prominent feature in the pathogenesis of atherosclerosis is the accumulation of blood lipoproteins, such as LDL, in cells lining vascular walls, and the proliferation of cells lining and within vascular walls, such as smooth muscle cells. The resultant narrowing of the blood vessel lumen at the site of the atherosclerotic lesion may give rise to varying degrees of tissue ischemia. While ischemic events may be reversible, either spontaneously or through medical intervention, the process of tissue injury may persist to the stage of reperfusion injury, in which the previously ischemic tissue is still at risk for damage, through several mechanisms, including oxidative damage.

Experiments 30–33 demonstrate the anti-proliferative effects of the PL-conjugates on arterial smooth muscle cells, unstimulated or stimulated by thrombin, and on the proliferation of human venous smooth muscle cells and aortic endothelial cells.

Experiment 30

Figure 23:
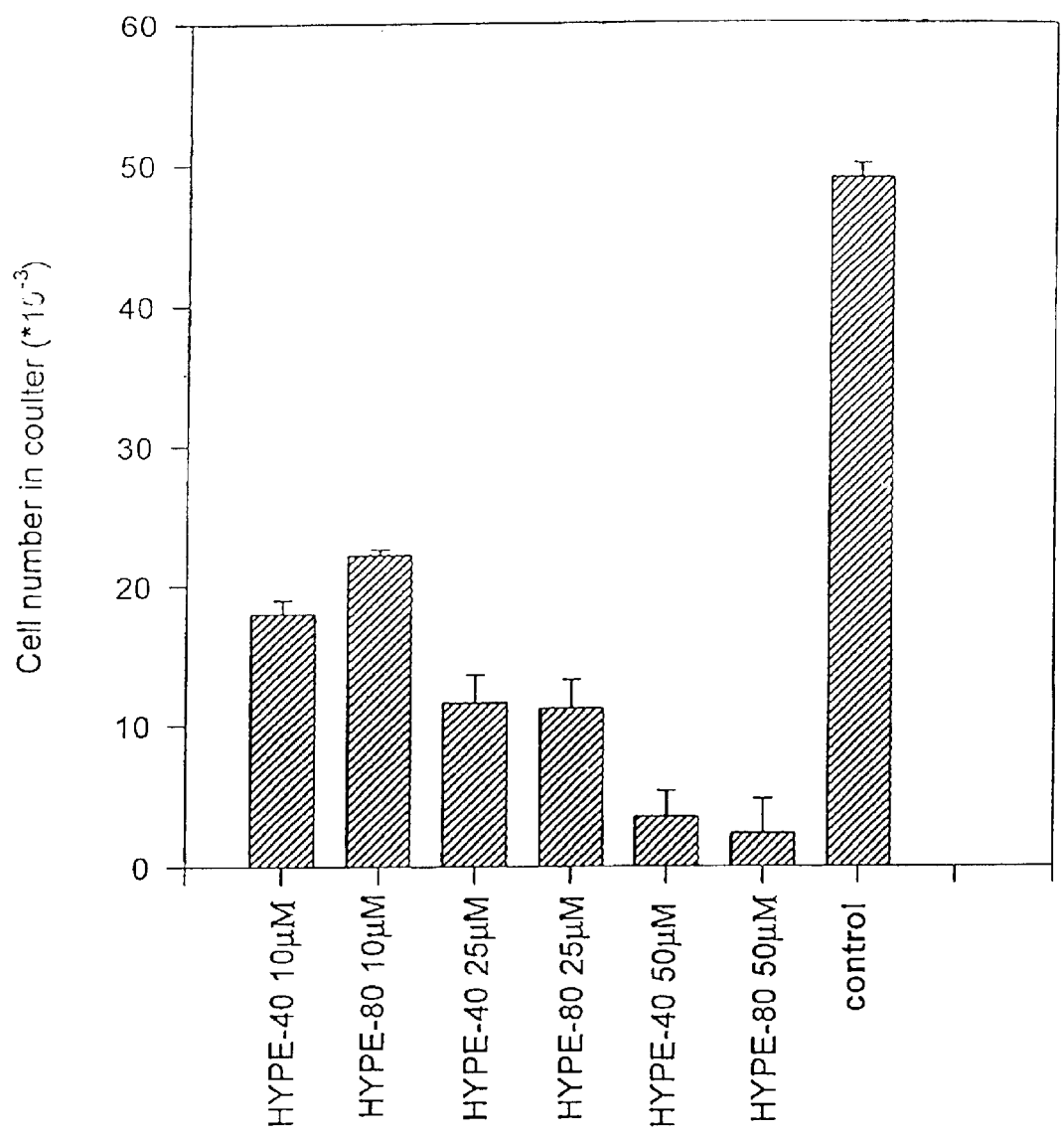

For unstimulated cells, bovine aortic smooth muscle cells were seeded at $7·10^3$ cells per well (in 24-well plates), in DMEM supplemented with 10% FCS, in the absence or presence of HYPE-40 or HYPE-80 (enriched with PE), grown for 72 h, and counted in coulter (FIG. 23).

Experiment 31

Figure 24:
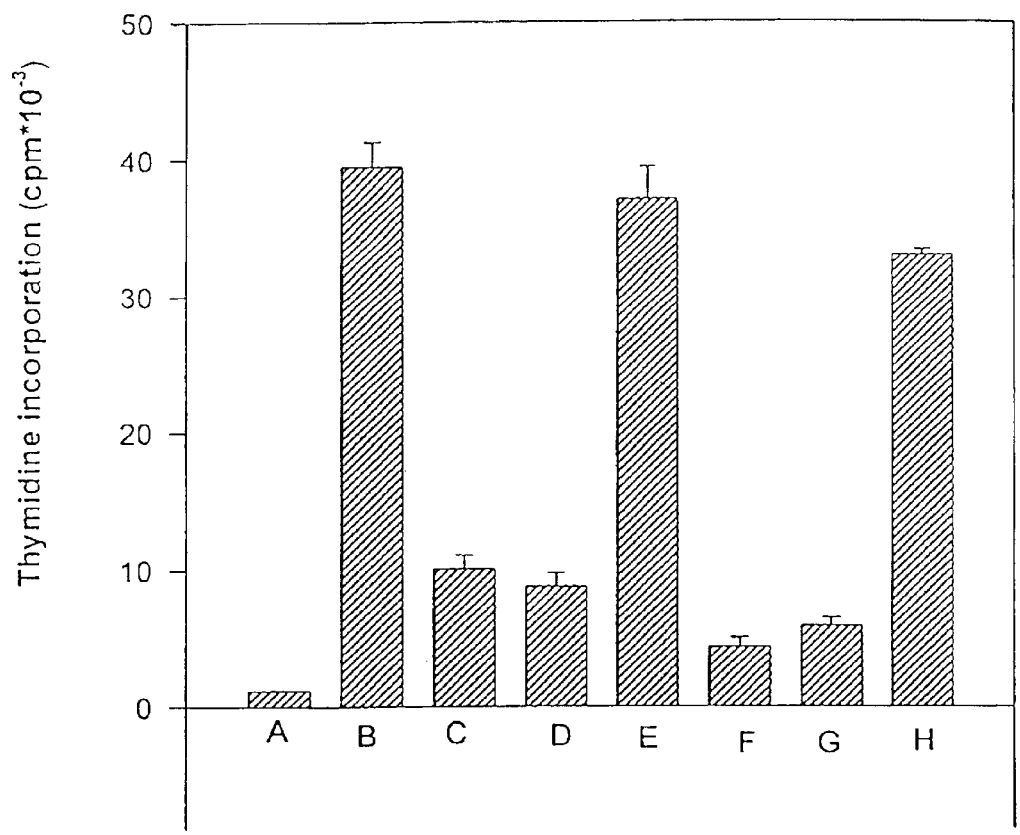

For stimulated cells, bovine aortic smooth muscle cells were grown under the conditions above for 48 h, following pre-incubation for 6 h, as indicated, with either thrombin, fetal calf serum, PL-conjugate, or both. Cell growth is represented as the amount of thymidine incorporation (FIG. 24).

Experiment 32

Figure 25:
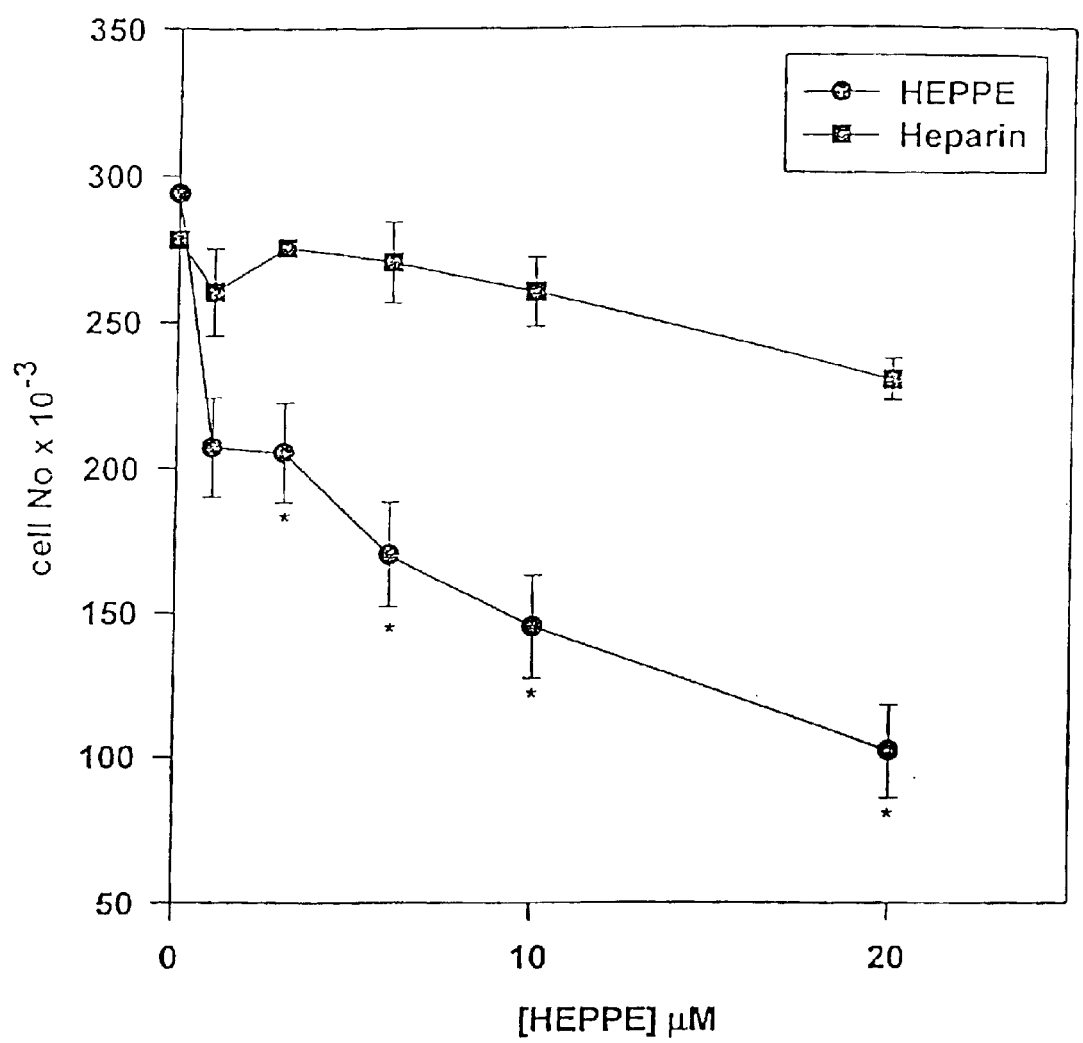

For assessing the effect of PL-conjugates on proliferation of human venous smooth muscle cells, smooth muscle cells (SMC) from human saphenous vein, were inoculated at $8×104/5$ mm culture dish, in DMEM supplemented with 5% fetal calf serum and 5% human serum. A day later the cells were washed and incubated in the same culture medium in the absence (control) or presence of the PL-conjugate (HEPE) or its polymeric carrier (heparin, at the same concentration as the HEPE). After 5 days the cells were harvested (by trypsinization) and counted (FIG. 25). Each datum is mean SEM for 3 replications (the same results were obtained in a second reproducible experiment). *$p<0.005$.

Experiments 33–34

To demonstrate inhibition of LDL uptake by cultured macrophages and in whole animals, human LDL (isolated by the conventional method of floatation) were subjected to $Cu^{2+}$-induced oxidation, and labeled with $^{125}I$. Confluent J774 macrophages were incubated with 100 μM $^{125}I$-oLDL and PL-conjugate at the indicated concentration in PBS buffer (pH=7.4) supplemented with 0.5% BSA, for 3 h. The cells were then washed 4 times with the PBS/BSA buffer, and subjected to lysis by 0.1 N NaOH for 30 min the cell lysate was collected and the $^{125}I$ content was determined in a radioactivity counter (Table 11).

TABLE 11

Inhibition of Macrophage Oxidized LDL Uptake by HYPE and HEPPE

| | Cell-associated $^{125}$I-oLDL (DPM × $10^{-3}$) | % Inhibition |
|---|---|---|
| Control | 92.2 ± 4.0 | |
| 10 µM HYPE | 20.9 ± 1.7 | 78% |
| 20 µm HEPPE | 59.2 ± 8.3 | 37% |

Figure 26:
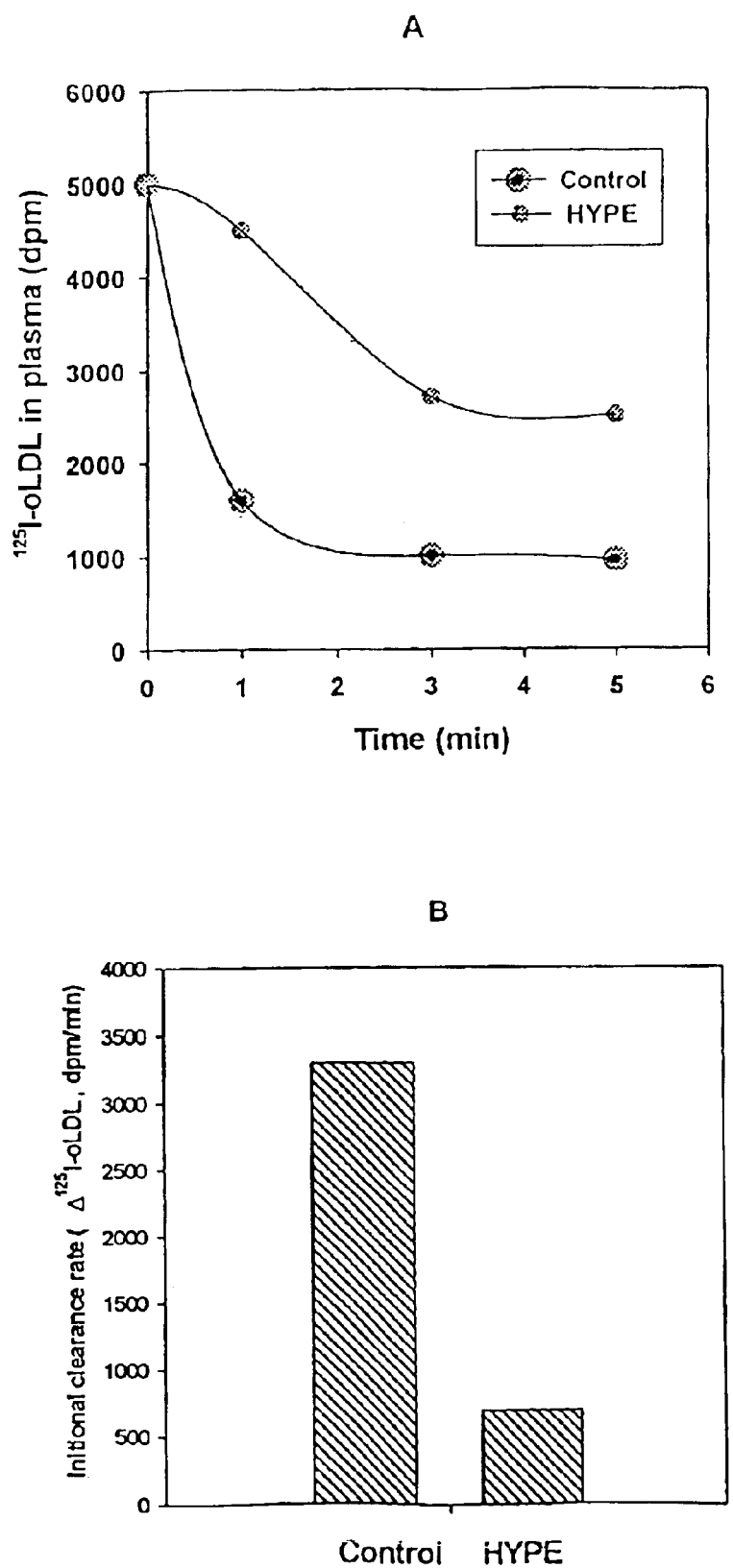

Rats weighing 200 g were injected I.V. with 0.4 ml containing 250 mmole of $Cu^{2+}$-induced oxidized LDL labeled with $^{125}$I, and 200 mmole of HYPE. Blood samples were drawn at the indicated time intervals and the $^{125}$I radioactivity in the plasma was counted (FIG. 26).

Experiment 35

Figure 27:
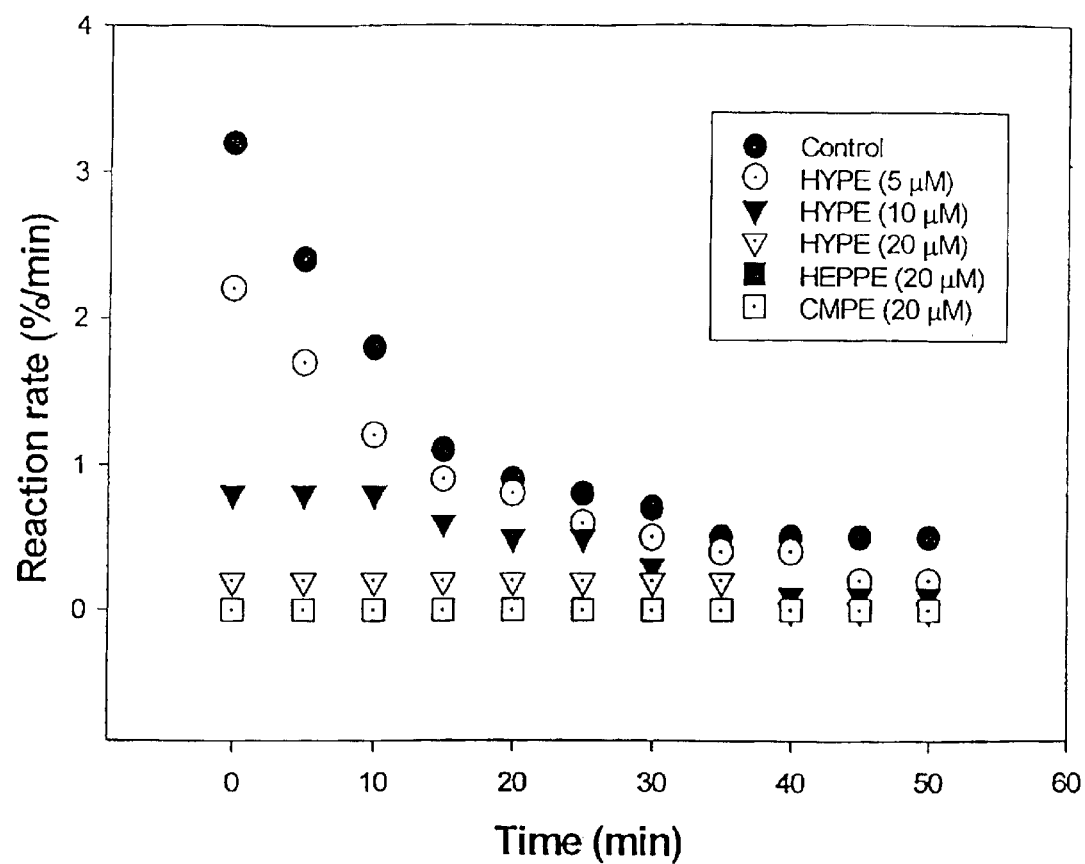

For demonstrating PL-conjugate inhibition of LDL-associated phospholipase activity. LDL (0.1 µM) was incubated for 15 min at 37° C. in the absence or presence of HYPE, HEPPE or CMPE at the concentrations indicated (FIG. 27). At time zero $C_6$-NBD-PC (0.5 µM) was added to the dispersion. This resulted in an instantaneous increase of fluorescence intensity (due to incorporation of NBD into lipidic cores). When LDL was incubated alone the increase of fluorescence was followed by time-dependent decrease of fluorescence intensity that can be attributed to hydrolysis of the LDL-associated PLA (and subsequent departure of the resultant NBD-caproic acid from the LDL particle to the aqueous medium). When LDL was incubated in the presence of HYPE, HEPPE or CMPE this time-dependent decrease was fully or partially inhibited.

Experiment 36

Figure 28:
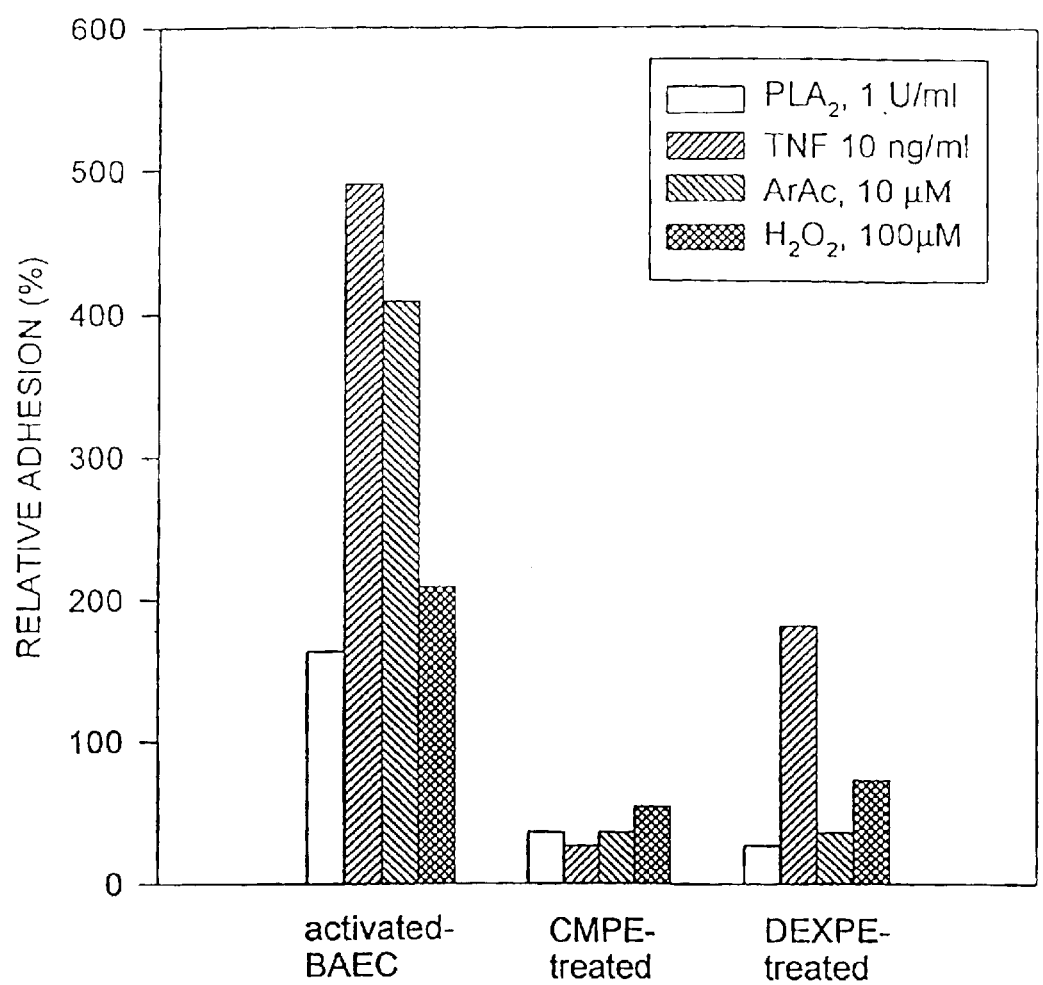

For demonstrating the protective effect of PL-conjugates on endothelium, bovine aortic endothelial cells were exposed to either tumor necrosis factor (TNF-α), phospholipase $A_2$, arachidonic acid, or hydrogen peroxide, and then assayed for cytodamage, as judged by adhesion of red blood cells as an index of endothelial intactness. Bovine aortic endothelial cells (BAEC) were pre-incubated for 30 min with either 5 µM CMPE or 20 µM DEXPE, then washed and stimulated for 18 h with TNF, ArAr, or $PLA_2$ at the indicated concentration. For stimulation with $H_2O_2$, the cells were treated with $H_2O_2$ for 20 min, then washed and incubated in the control culture medium for 18 h. The BAEC were washed and incubated with human red blood cells (RBC) for 30 min. The cultures were washed and the RBC which remained adhered to the BAEC were counted under a microscope (FIG. 28).

These experiments demonstrate that administration of PL-conjugates are effective therapy in the treatment of cardiovascular disease, including atherosclerosis and reperfusion injury, by a plurality of mechanisms, including inhibition of vascular smooth muscle cell proliferation, uptake of lipoprotein, and leukocyte activation in models of ischemia and reperfusion.

EXAMPLE 7

Prophylaxis For Invasive Surgical Procedures, Including Catheterization

PL-conjugates are effective in the treatment and prophylaxis for cardiovascular disease in many settings, including atherosclerosis, as described above, as well as in the setting of stenosis-restenosis known as reperfusion injury. In addition, these agents are effective for preventing the formation of stenotic lesions as may occur in the course of invasive surgical procedures which involve manipulation of vascular organs, in particular vascular catheterization.

Experiments 37–38

To demonstrate the efficacy of PL-conjugates in protocols for balloon induced stenosis in rats, in the carotid artery by both systemic (Table 12) and intravenous infusion (Table 12) administration. Rats were pre-treated with I.P. injection of 10 mg/100 g body weight of HYPE in PBS, or PBS alone, 1 day, and also 1–2 hours before injury. Injury was achieved using the standard Fogarty catheter. The rats were injected with the same amount of drug or vehicle every day for 3 days, and then every other day, for a total of 8 injections. Rat were sacrificed on the $14^{th}$ day, the arteries were processed according to standard procedure. Half of the rats were injected with bromodeoxyuridine (BrdU), fixed with formalin and triton, and processed for BrdU staining, areas of the indicated vascular structures measured for comparison (Table 12). The distal left common and external carotid arteries were exposed through a midline incision in the neck. The left common carotid artery was denuded of endothelium by the intraluminal passage of a 2F Fogarty balloon catheter (Baxter, Santa Anna, Calif.) introduced through the external carotid artery. The catheter was passed three times with the balloon distended sufficiently with saline to generate a slight resistance. The catheter was then removed and a polyethylene tube (PE-10) connected to a syringe was introduced into the common carotid artery. A segment of the common carotid artery was temporarily isolated by sliding ligature and vascular clamp. Approximately 50 µl of solution containing 10 nmole of CMPE was injected into isolated arterial segment and left in place for 15 min. The drug solution was then evacuated and the external carotid artery was ligated. The rats were sacrificed 2 weeks later, and the percent of luminal stenosis (in the damaged area) was determined by histological measurement of neointima to media area ratio (Table 12).

TABLE 12

Inhibition of Balloon-Induced Stenosis in Rats by PL-Conjugates

| Experiment | Treatment | % stenosis (Mean ± SEM) | p | N/M | p |
|---|---|---|---|---|---|
| 1. I.P. administration | Untreated (n = 7) | 53.96 ± 4.11 | 0.003 | 1.64 ± 0.12 | 0.001 |
| | HyPE (n = 6) | 53.96 ± 2.89 | | 1.0 ± 0.08 | |
| 2. IP. administration | Untreated (n = 6) | 41.53 ± 4.84 | 0.023 | 1.16 ± 0.12 | 0.036 |
| | CMPE (n = 8) | 21.89 ± 5.42 | | 0.64 ± 0.17 | |
| 3. Intra-arterial administration | Untreated (n = 4) | 53.12 ± 12.8 | 0.052 | 1.61 ± 0.17 | 0.008 |
| | CMPE (n = 6) | 29.64 ± 2.17 | | 0.99 ± 0.08 | |

These experiments demonstrate that administration of PL-conjugates are of both prophylactic and acute therapeutic benefit when administered in the course of invasive arterial procedures, particularly balloon angioplasty. Additional support of therapeutic benefit of the administration of PL-conjugates in cardiovascular disease therapy may be found in the demonstrated efficacy of LDL oxidation as shown in Experiment 46, below. Additional support for the utility of administration of PL-conjugates in cardiovascular disease therapy is shown in Experiment 43, below, demonstrating inhibition of endothelial cell proliferation by PL-conjugates, as well as in Experiments 57–58, below, demonstrating the efficacy of administering PL-conjugates for the treatment of stenosis/reperfusion injury.

EXAMPLE 8

Invasive Cellular Proliferative Disorders

The PL-conjugates are effective therapy for cellular proliferative disorders, such as cancer. This is demonstrated in experiments 30–33 above and 39–43 below. The process of cancer spread entails a multiple events, each of these is a worthy target for inhibitory drug action, including the rate of cell-proliferation, the rate of spread through blood vessels, the rate of invasiveness through contiguous and non-contiguous (metastases) tissues, and the rate of production of new blood vessels to supply the cancerous growth. Cancer cells frequently produce intracellular matrix tissue degrading enzymes which serve to enhance their invasive potential. Cancer is thus a multiphasic disease involving the process of tissue invasiveness, spread through tissue channels, angiogenesis and tumor vascularization. These latter processes depend upon the rates of proliferation of smooth muscle and endothelial cells.

Experiment 39

Figure 29:
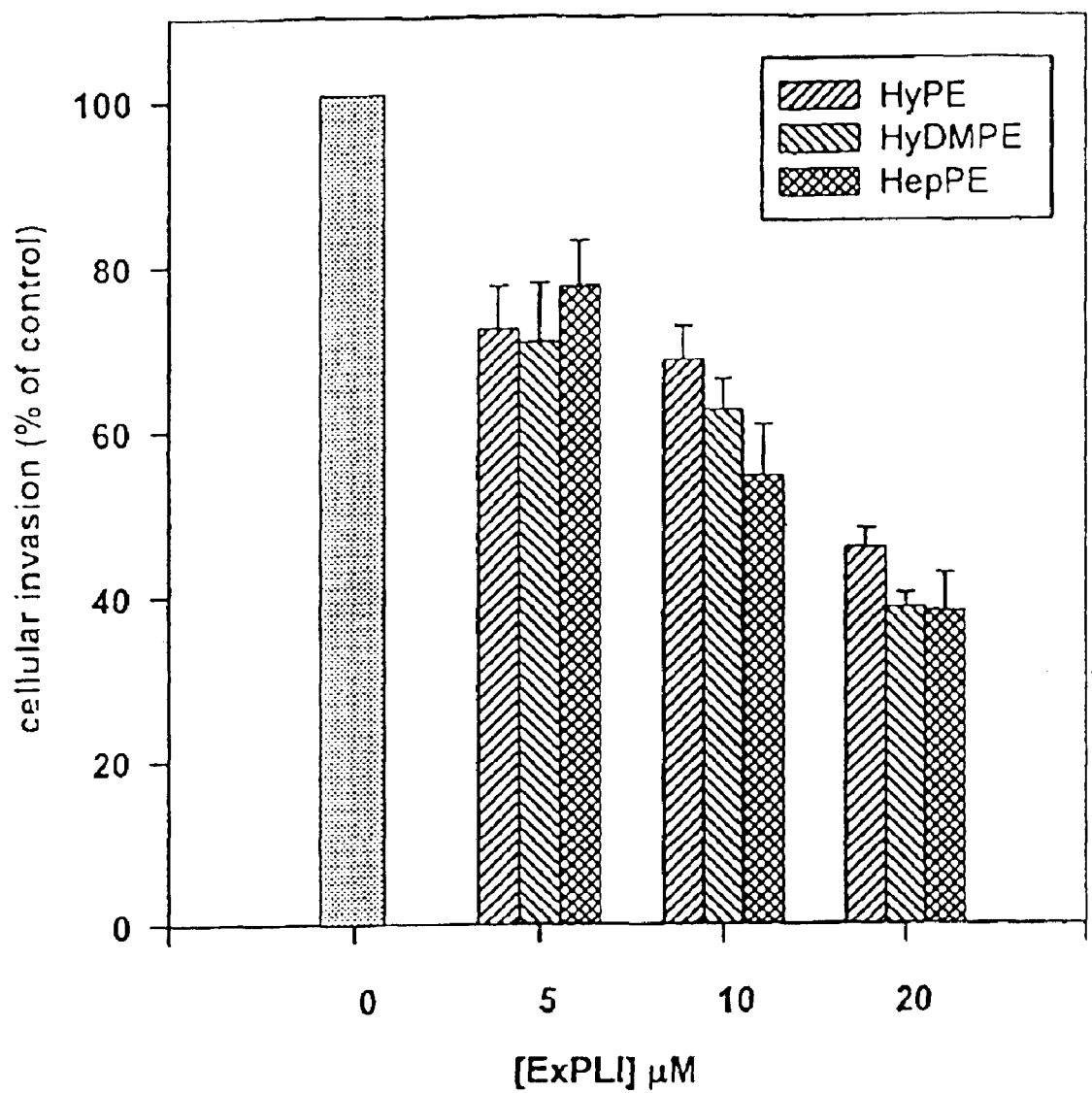

For showing the ability of the PL-conjugates to inhibit the invasion of tumor cells through basement membrane, the chemoattractant invasion assay was used (FIG. 29). For details, see Methods and Materials below.

Experiments 40–42

Figure 30:
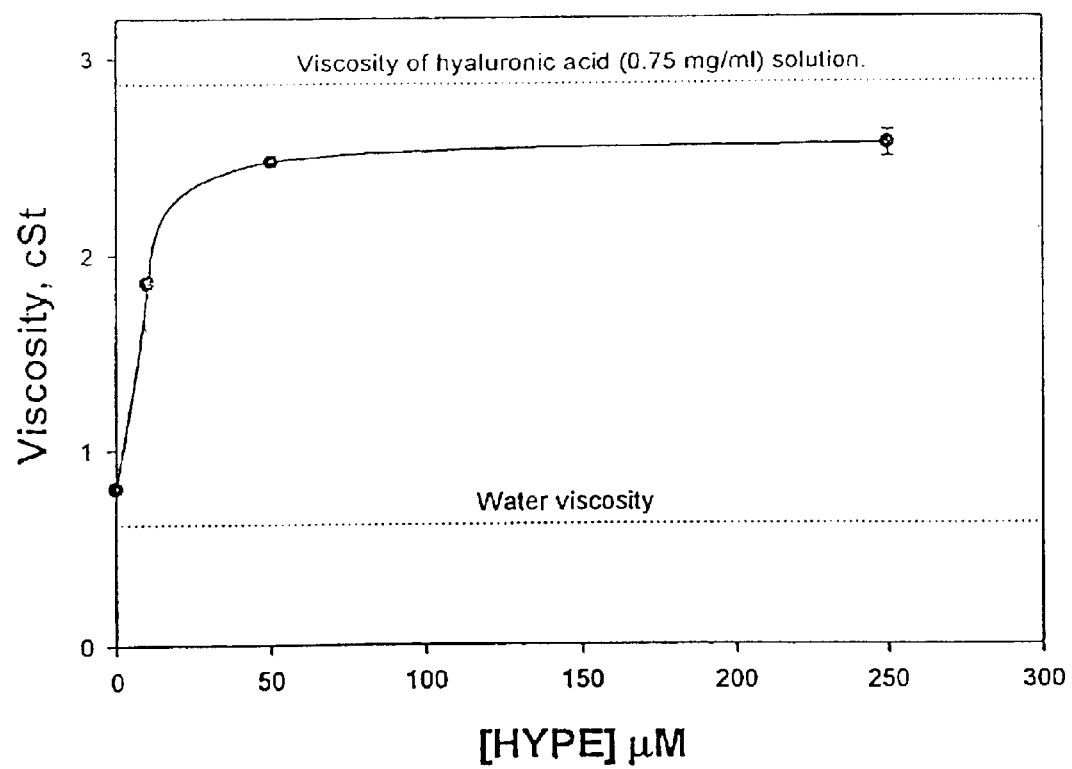
Figure 31:
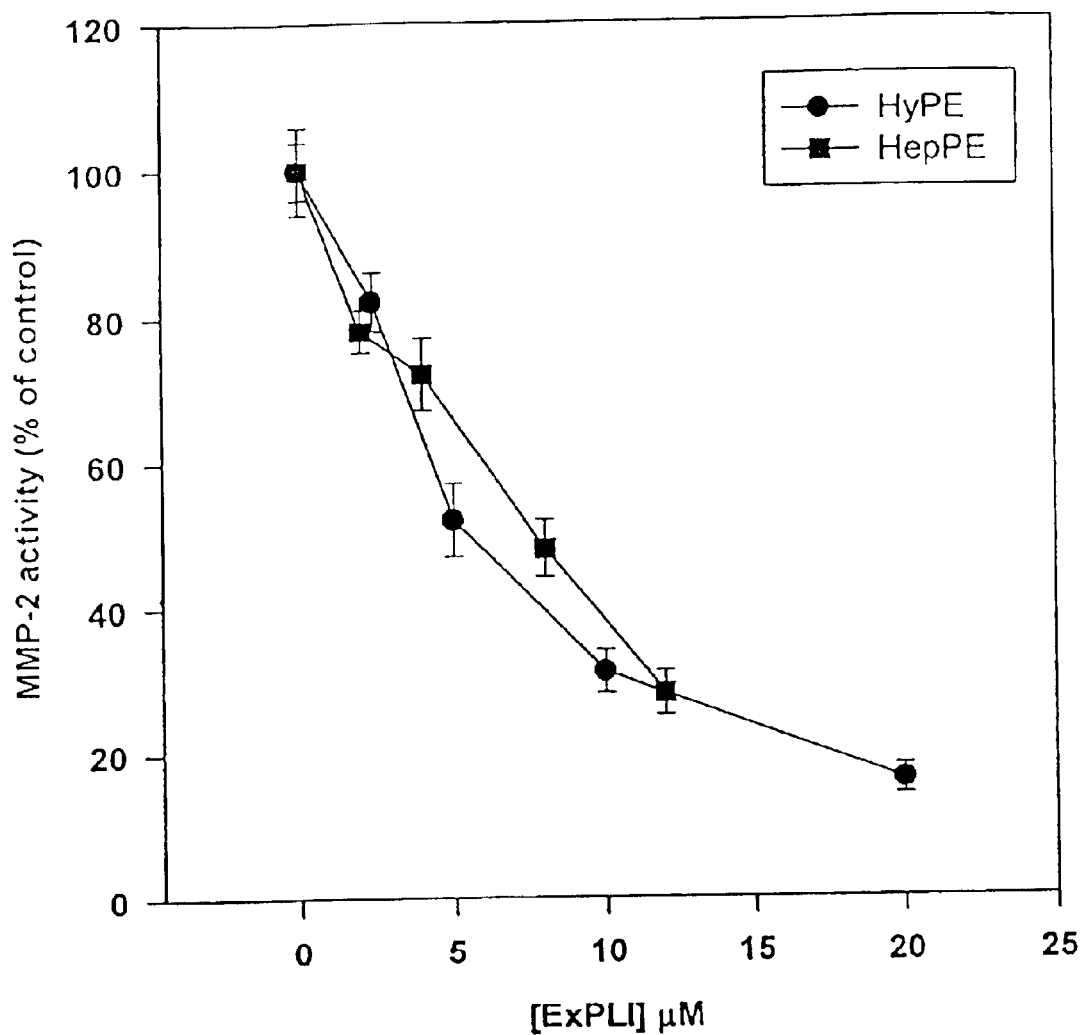
Figure 32:
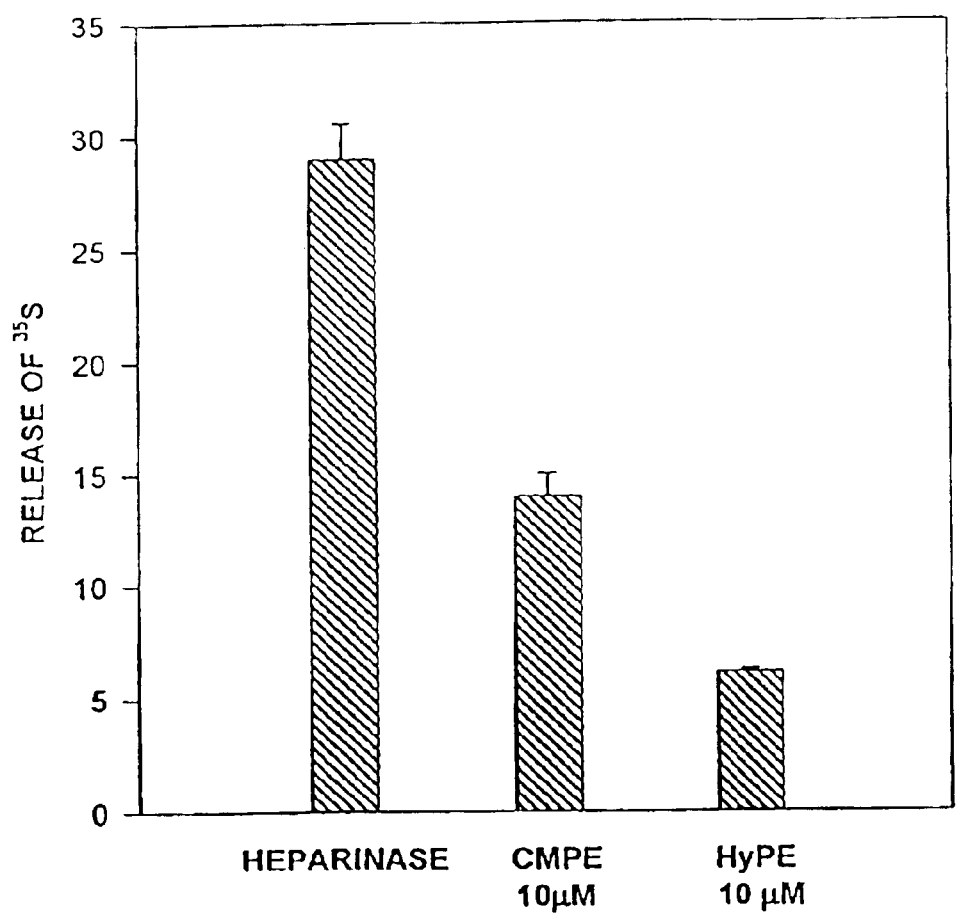

To demonstrate the ability of the PL-conjugates to act as agents which inhibit the expression or activity of tissue degrading enzymes. Hyaluronic acid (HyA) in PBS (0.75 mg/ml) was treated with hyaluronidase (15 U/ml) in the absence or presence of HYPE, at the indicated concentration for 1 h. Hyaluronic acid degradation was determined by the change in the viscosity of its solution (FIG. 30). Similar experiments with PL-conjugates were performed using an assay for collagenase activity and heparinase activity. HT-1080 (fibrosarcoma) cells were incubated for 24 h with HYPE at the indicated concentration. The culture medium was then collected and its collagenase activity was determined by a zymographic assay. Each datum is average of two plates (with an error of about 5%) (FIG. 31). BGM cells were labeled overnight with 50 µCi $^{35}SO_4^{2-}$ per well. The cells were washed 3 times with PBS before treating with 5 units of heparinase I in 200 µl PBS for 3 h. The medium was collected and its $^{35}S$ content was counted (FIG. 32). Experiments 30–33 above also demonstrate the anti-proliferative effects of the PL-conjugates, inhibiting the growth of different cell types ranging from fibroblasts to smooth muscle cells to endothelial cells of vascular origin. This demonstrated anti-angiogenesis potential of the PL-conjugates is particularly significant for the inhibition of tumor growth and spread.

Experiment 43

Figure 33:
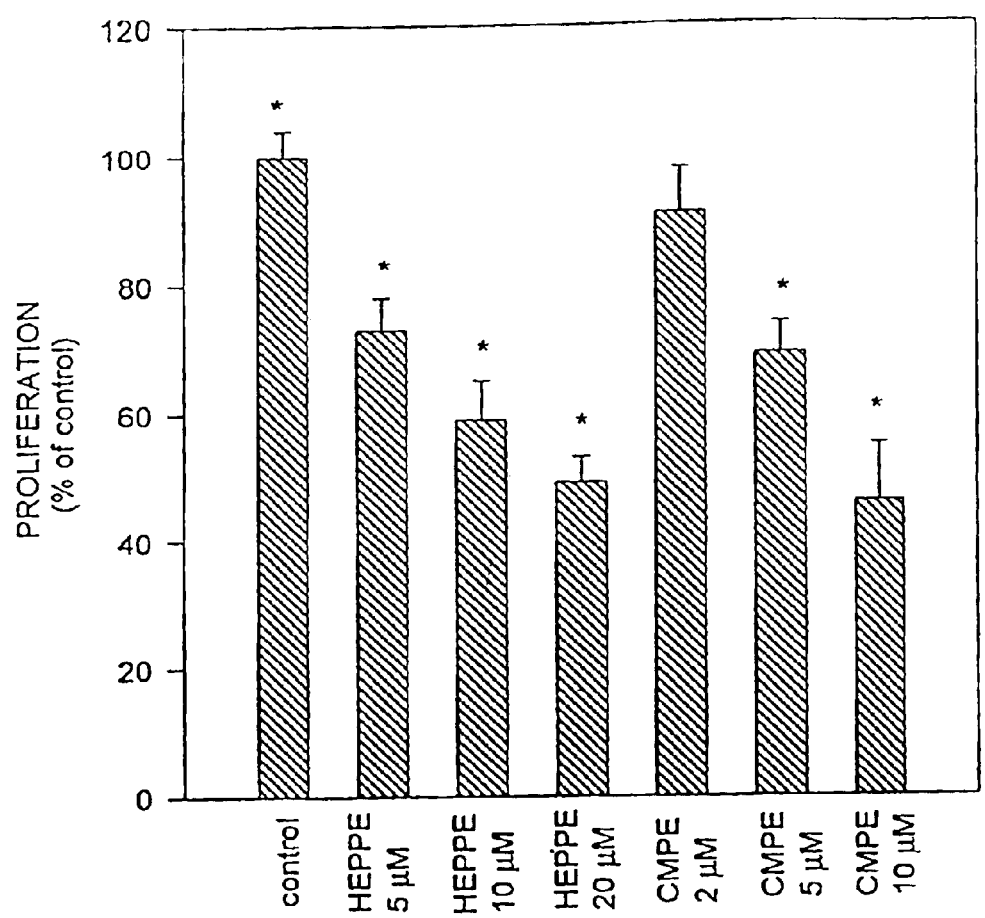

For the effect of PL-conjugates on proliferation of endothelial cells, bovine aortic endothelial cells were plated in culture dishes for 6 h, then washed to remove unattached cells. The remaining attached cells were incubated in the absence (control) or presence of PL-conjugates at the indicated concentration for 48 h. The cells were then washed, collected by trypsinization and counted in a Coulter counter. The results are mean±S.D. for 3 replications. *p<0.005 (FIG. 33).

These experiments demonstrate that administration of PL-conjugates are effective therapy in the treatment of cancer, by a plurality of mechanisms, including anti-proliferation, anti-invasiveness, and anti-angiogenesis.

EXAMPLE 9

Anti-Oxidant Therapy

The PL-conjugates are effective therapy for preventing oxidative damage. This is demonstrated in Experiments 45–47. The noxious effect of peroxide free radicals on living tissue is known as oxidative damage. When cell membranes are the targets for this damaging process, membrane dysfunction and instability result. Oxidative damage to blood proteins, particularly blood lipid proteins, results in their over-accumulation in cells lining the vasculature, thus contributing to atherogenesis. In fact, oxidative cell damage is a major mechanism attributed to the process of aging or senesence.

Oxidative damage to proteins or cell membranes is commonly assessed by exposing these tissues to hydrogen peroxide produced by the enzyme glucose oxidase (GO), in the absence or presence of additional membrane destabilizing agents, such as $PLA_2$, or by exposure to divalent cations, such as copper.

Experiments 44–47 demonstrate the ability of PL-conjugates to preserve cells from oxidative damage, as judged by the cells retention of both arachidonic acid and of low molecular weight intracellular substances.

Experiment 44

Figure 34:
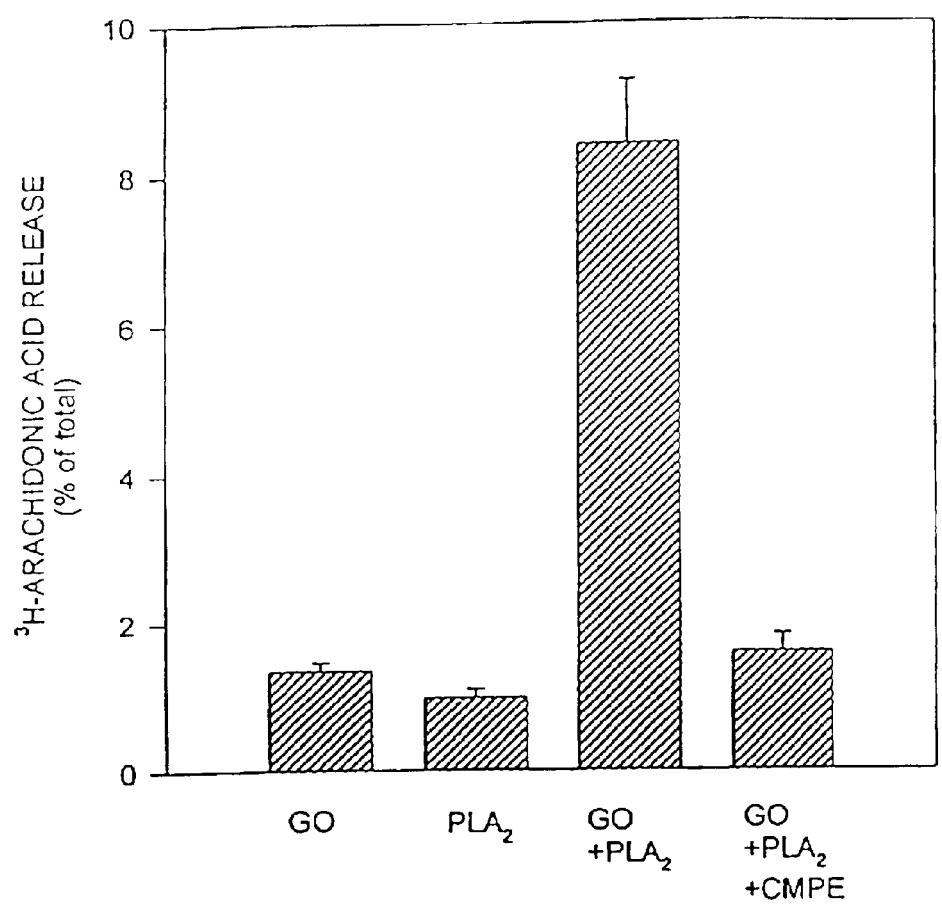

Confluent BGM (green monkey kidney epithelial cells) were labeled with $^3H$-arachidonic acid. The cells were treated with CMPE for 30 min prior to treatment with GO and $PLA_2$ (0.5 u/ml) (FIG. 34).

Experiment 45

Figure 35:
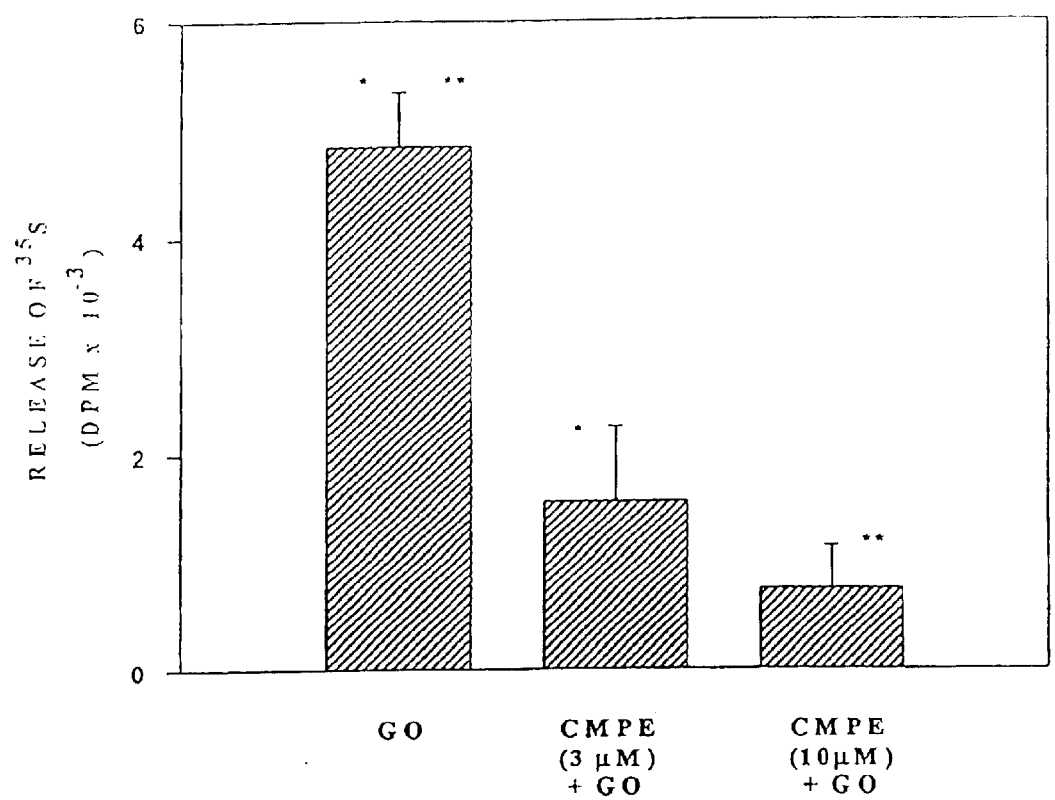

BGM cells were labeled with $^{35}SO_4$ overnight. The cells were washed with DMEM (containing 10 mg/ml BSA) 4 times with PBS. The cells were then incubated in DMEM supplemented with GO (an $H_2O_2$ generation) for 90, and the culture medium was collected and counted for $^{35}S$ radioactivity. For treatment with CMPE cells were incubated with CMPE at the indicated concentration for 30 min prior to introduction of GO. Each datum is MEAN±SEM for 5 replications. *p<0.005; **p<0.001 (FIG. 35).

Experiment 46

Figure 36:
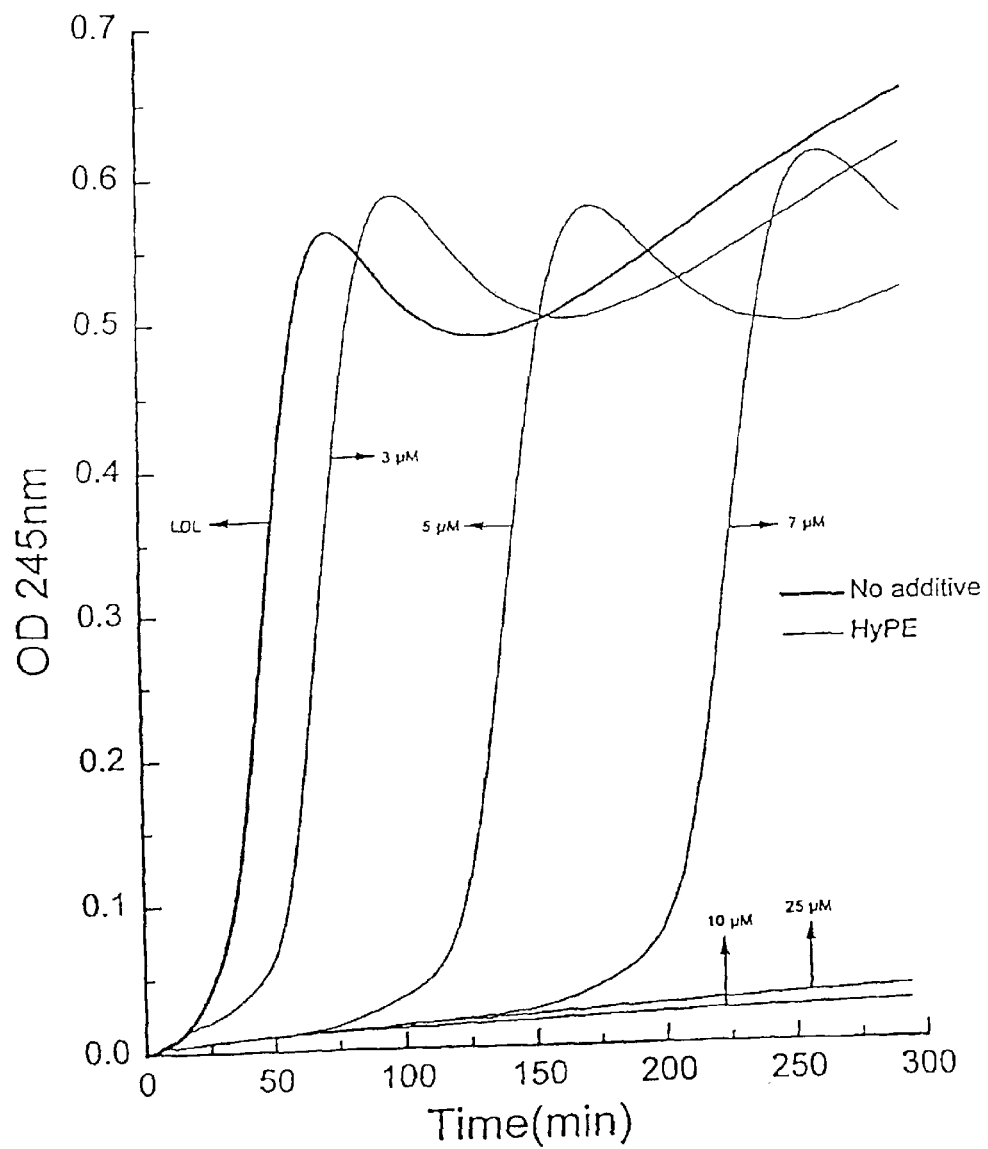

For demonstrating the ability of PL-conjugates to inhibit the oxidation of blood lipoprotein. LDL (0.1 µM) was incubated in the absence and presence of various concentrations of HYPE or HA at 37° C. At time zero 5 µM $CuCl_2$ was added to the dispersions and the mixtures were continuously monitored for oxidation products at 245 nm (FIG. 36). The absorbance at 245 (OD units) is depicted as a function of time (Shnitzer et al, Free Radical Biol Med 24; 1294–1303, 1998).

Experiment 47

Figure 37:
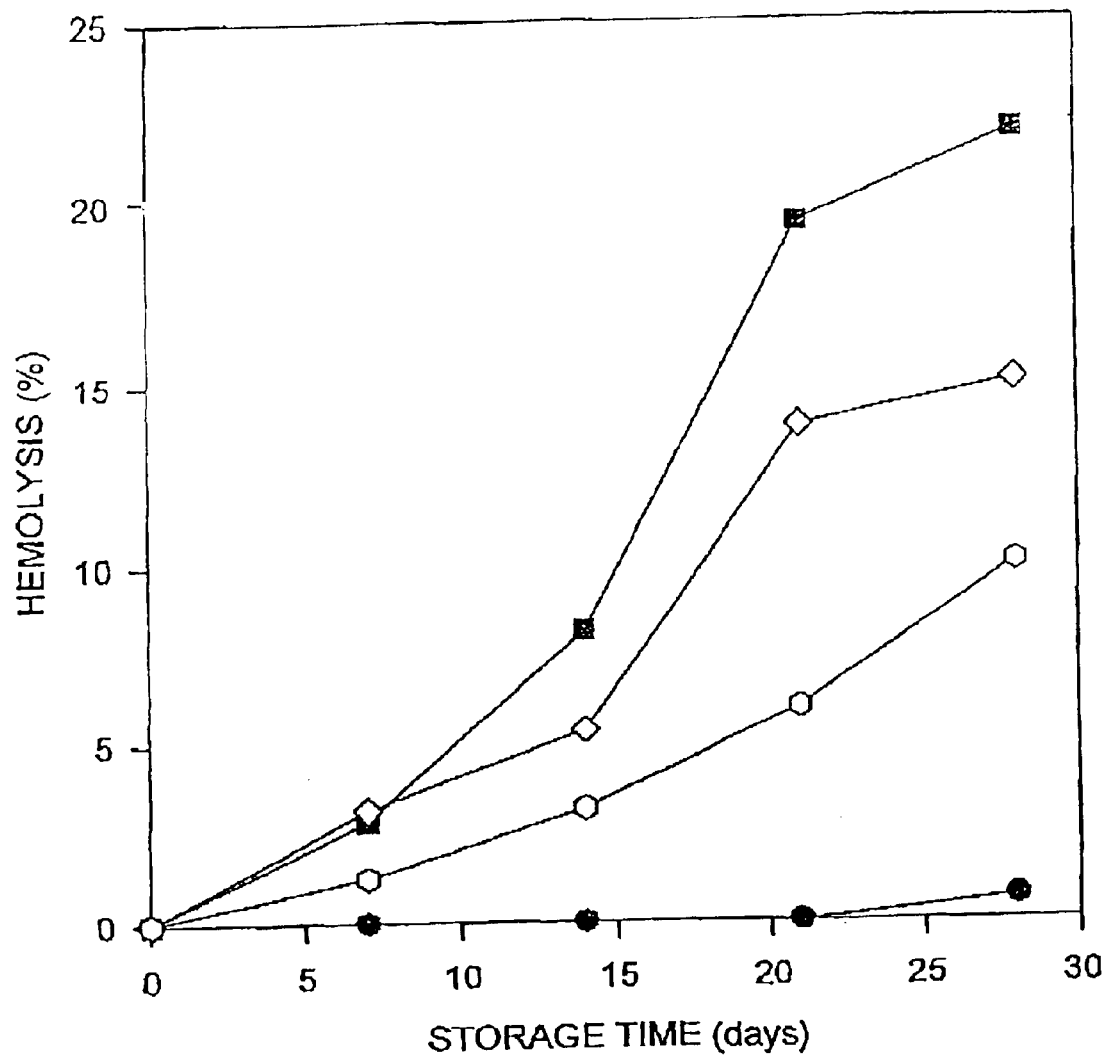

To demonstrate the protective effect of PL-conjugates on red blood cells under adverse, oxidizing storage conditions, namely light irradiation. Human RBC were treated with 2 µM P c4 (in 1 mM POPC, 4 mM cysteine, and 0.5 mM L-carnitine) and light-irradiation with 15 J/cm$^2$ in the absence or presence of PL-conjugates, as indicated (FIG. 37).

These experiments demonstrate that administration of PL-conjugates is effective therapy in the prevention of oxidative tissue damage, by a plurality of mechanisms, including inhibition of lipoprotein oxidation, inhibition of oxidized lipoprotein uptake (FIG. 28, FIG. 29), and by inhibiting arachidonic acid release and preserving the integrity of cell membranes, including red blood cell membranes, as described below.

EXAMPLE 10

Hemolysis

The PL-conjugates are effective therapy in the treatment and prevention of hemolysis. This is demonstrated in Experiments 48. Hemolysis, the breakdown of red blood cells (RBC), may be either a primary disease in itself, or a syndrome associated with another disease or physiological insult. A commonly accepted model for assessing the membrane-stabilizing effect of a drug is to incubate red blood cells in the presence of known membrane destabilizing agents and to detect for the release of hemoglobulin into the extracellular medium.

Experiment 48

For demonstration that PL-conjugates serve to maintain the stability of human red blood cells exposed to membrane-destroying enzymatic agents. Human RBC was washed in saline and suspended in Hanks buffer (pH-7.4). Hemolysis was induced in the absence or presence of PL-conjugate (10 µM), as indicated, by treatment with either streptolysin O (SLO) 5 U/ml, streptolysin S (SLS) 25 U/ml, or lysophosphatidylcholine lipase (lyso-PC) 5 µg/ml for 20 min. The cell membranes were spun and the hemoglobin content in the supernatant was determined by measuring the O.D. at 540 nm (table 14).

TABLE 14

Prevention of Hemolysis by HYPE, CMPE and HEPPE

| PJ-CONJUGATE | HEMOLYSIS (O.D. AT 540 nm) | | |
|---|---|---|---|
| | SLO | SLS | Lyso-PC |
| None | 1.000 | 1.000 | 1.000 |
| HA | 1.000 | 1.000 | 1.875 |
| HYPE-30 | 0.650 | 0.750 | 0.335 |
| HYPE-60 | 0.012 | 0.005 | 0.017 |
| HYPE-110 | 0.005 | 0.002 | 0.012 |
| CMPE-60 | 0.012 | 0.005 | 0.002 |
| CMPE-110 | 0.002 | | 0.002 |
| HEPPE | 0.002 | 1.100 | 0.002 |

These experiments demonstrate that the PL-conjugates are effective therapy in the treatment of hemolysis and of value as preservatives in blood product storage. Thus PL-conjugates are demonstrated to have utility in maintaining hematocrit and in blood-banking.

EXAMPLE 11

Sepsis

The PL-conjugates are effective therapy in the treatment of bacteremia with shock, otherwise known as sepsis. This is demonstrated in Experiments 49–50.

Tumor necrosis factor (TNF-α) is a major cytokine involved in the pathogenesis of septic shock, being released both locally and systemically to produce noxious and irreversible effects on tissue integrity and systemic hemodynamics. Exposure of cells to the bacterial lipopolysaccharide immunogen (LPS) is a comprises a commonly used model system for assaying the TNF-α response to septicemic conditions. In addition to TNF-α, other chemokines of relevance to the pathophysiology of septicemia and septic shock are MCP-1, ENA-78, Gro-α, and CX3C.

Experiment 49

Figure 38:
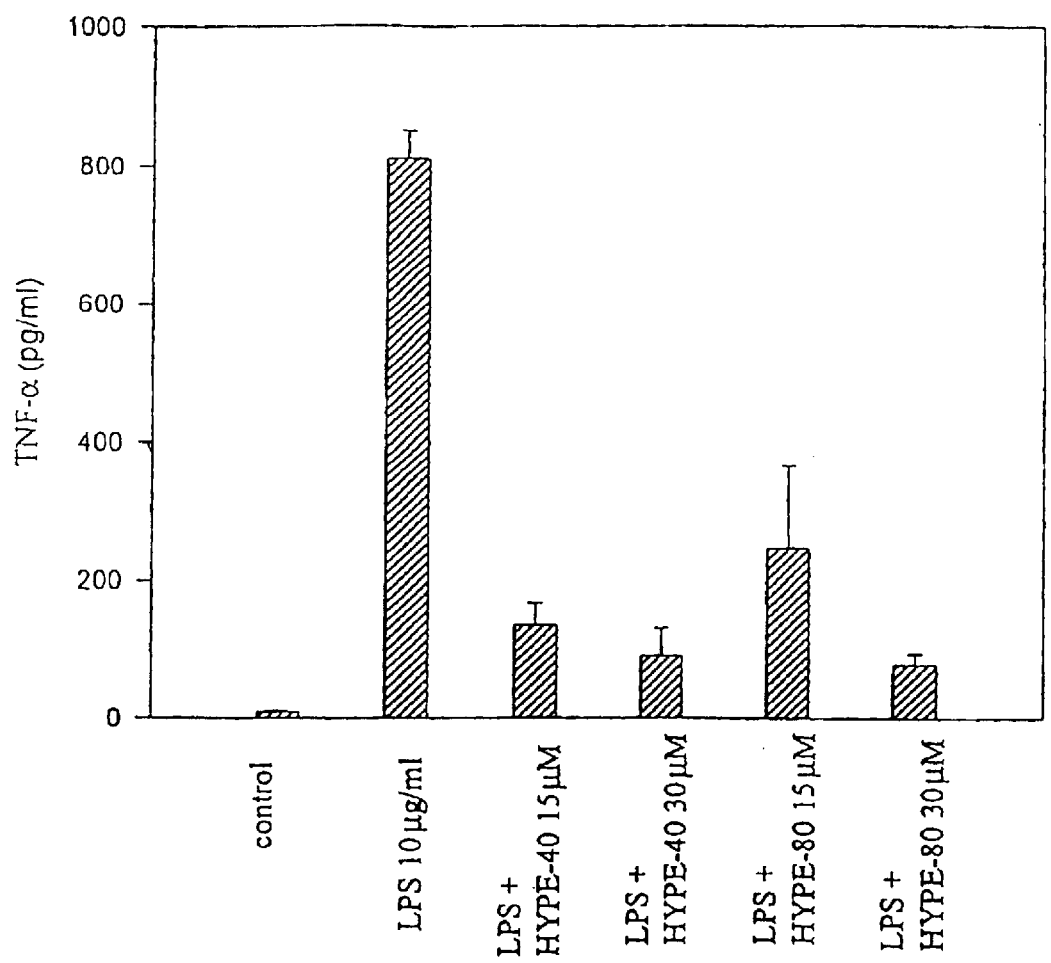
Figure 38A:
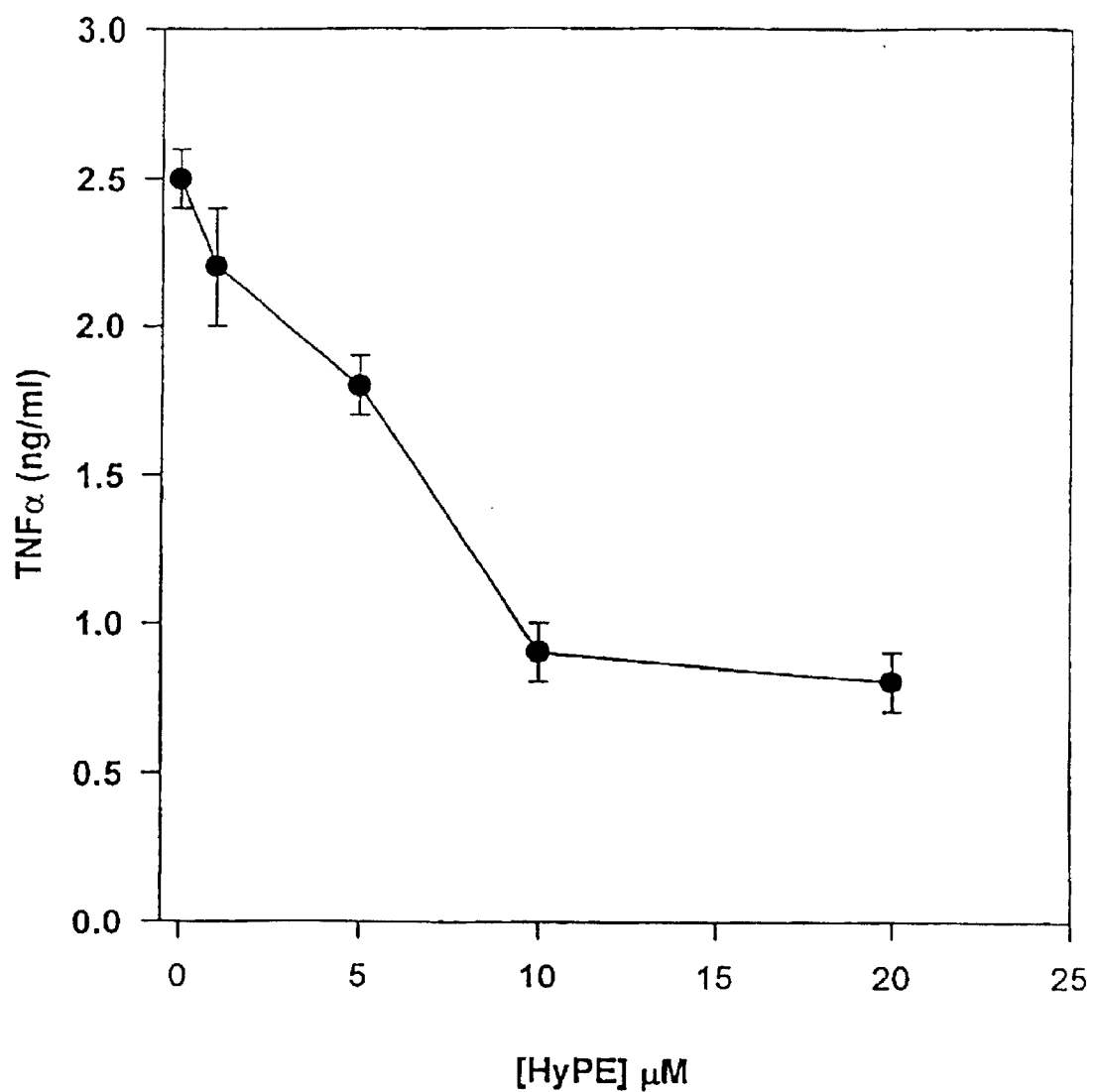

To exemplify the ability of PL-conjugates to inhibit elaboration of TNF-α in human tissue, fresh heparinized (12.5 U/ml) human venous blood from healthy blood donors was diluted 1:3 with medium RPMI-1640, supplemented with 200 mM glutamine, 200 U/ml penicillin and 200 U/ml streptomycin. Fractions (300 µl) of 1:3 diluted blood were distributed in 24 well Multidisk plates (Nunclon). Blood samples were pre-incubated (30 min at 37° C.) in a humidified atmosphere of 6% $CO_2$ with 100 µl of compound or solvent before being stimulated by the addition of 100 µl of lipopolysaccharide E. coli 026:B6 (LPS) at a final concentration of 100 ng/ml. After 6 h incubation, the 24 well plates were spun down (2000 rpm×10) and assayed for cytokine content by ELISA. The various HYPESs differ in their phosphate content (FIG. 38 and FIG. 38a).

Experiment 50

Figure 39:
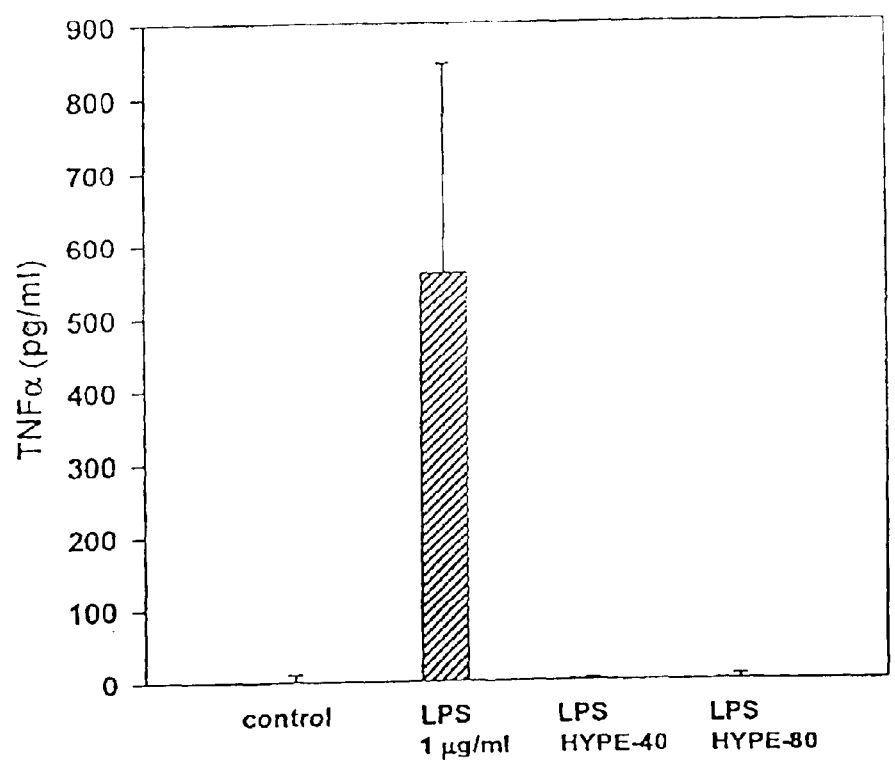

To demonstrate the ability of PL-conjugates to inhibit elaboration of TNF-α in mouse cells. Primary mouse peritoneal macrophages were treated with PL-conjugates at the indicated concentration for 30 min. Then LPS (1 µg/ml) was added to the culture either directly or after washing of the PL-conjugate. TNF was determined by ELISA (FIG. 39).

The effect of PL-conjugates on other chemokines, such as MCP-1, ENA-78, Gro-α, and CX3C, is demonstrated in Experiments 53 and 54 described below.

These experiments demonstrate that administration of the PL-conjugates is effective therapy in the treatment of sepsis. Additional support for the utility of PL-conjugates in the treatment of sepsis is shown in Experiments 15 and 16, above, demonstrating inhibition of nitric oxide production by PL-conjugates.

EXAMPLE 12

Acute Respiratory Distress Syndrome (ARDS)

The PL-conjugates are effective therapy in the treatment of acute respiratory distress syndrome (ARDS). This is demonstrated in Experiment 51 and 52. In ARDS four different chemokines associated with the pathophysiology of the condition are MCP-1, ENA-78, Gro-α, and CX3C and these are expressed in microvascular endothelial cells in response to stimulation by foreign antigens, for example LPS.

Experiment 51

Figure 40:
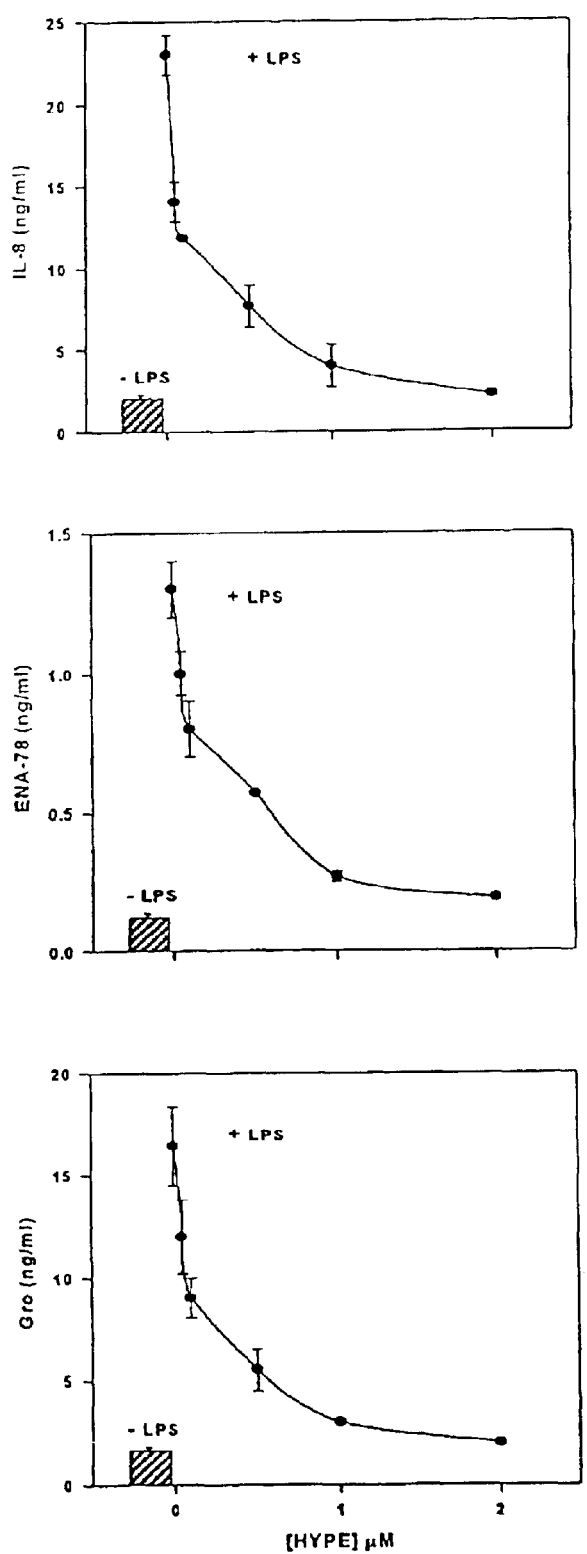

To show that the PL-conjugates inhibit chemokine elaboration in microvascular endothelial cells from human lung. HLMVEC were incubated for 24 h with 1 µg/ml LPS in the absence or presence of HYPE at the indicated concentrations. The level of the chemokines Gro-α, ENA-78, and MCP-1 accumulated in the culture medium was determined by ELISA. The secretion of ENA-78 and MCP-1 was blocked already at 10 µM of HYPE (FIG. 40).

Experiment 52

Figure 41:
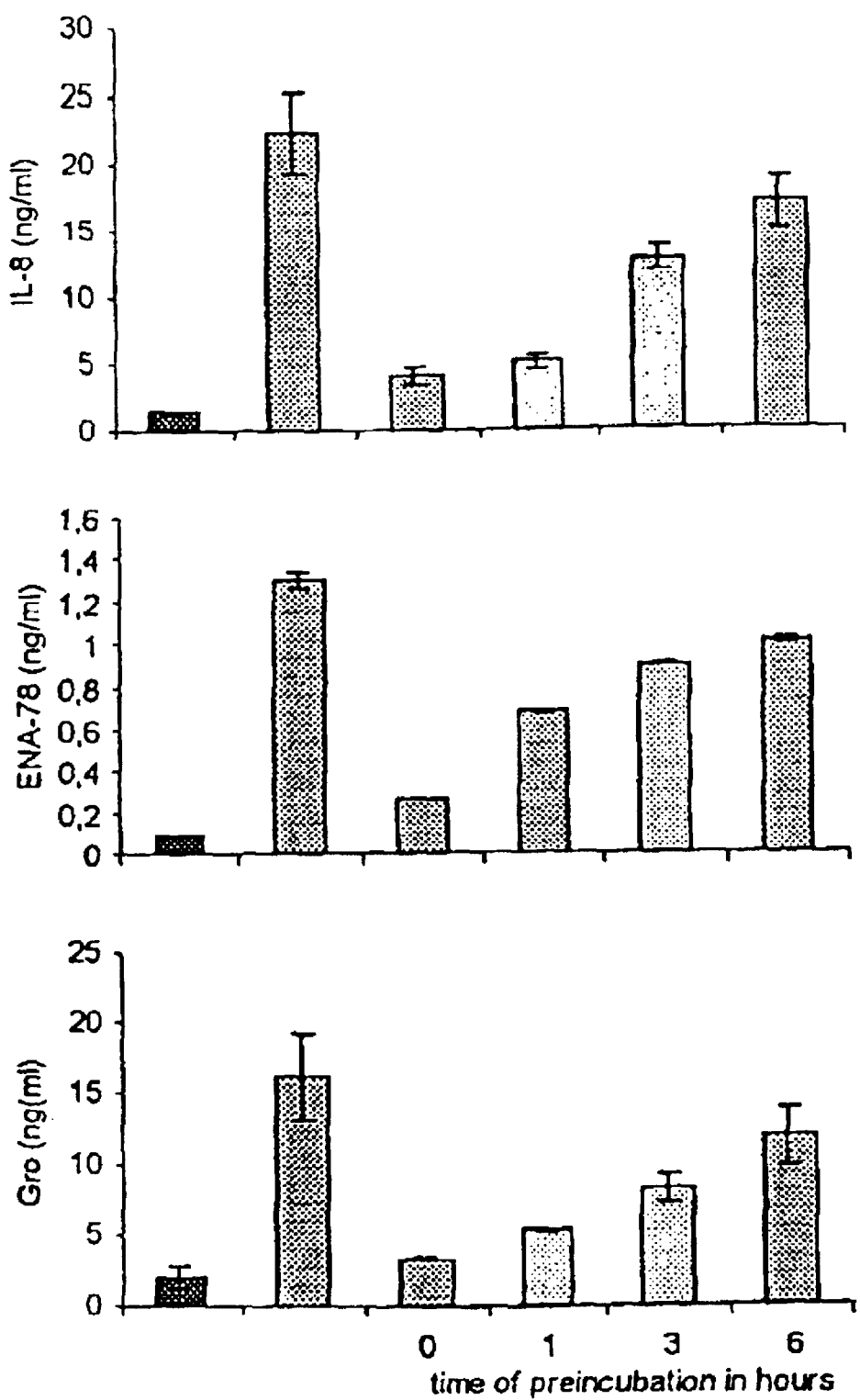
FIG. 41b. Effect of PL-Conjugates on Expression of NF-κβ
Figure 41A:
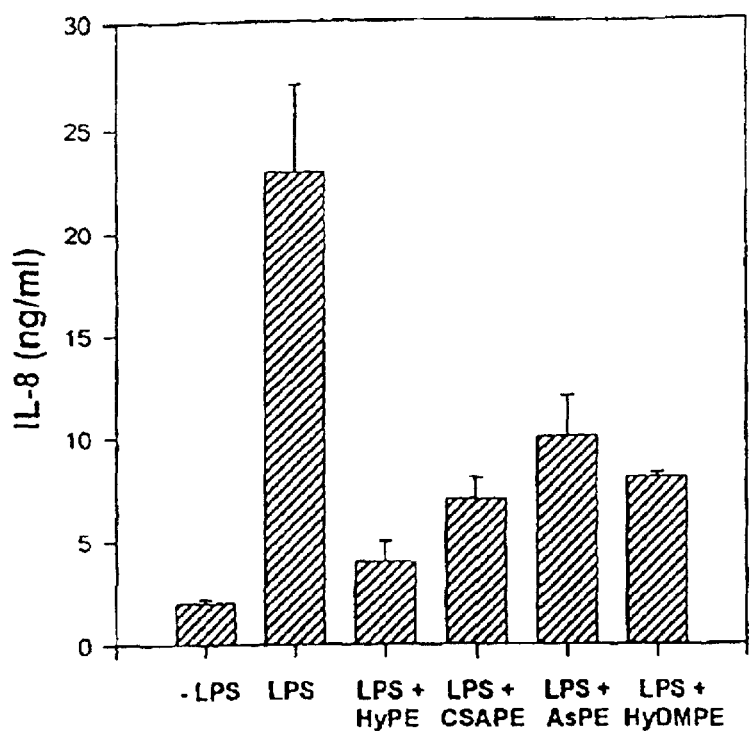
Figure 41A:
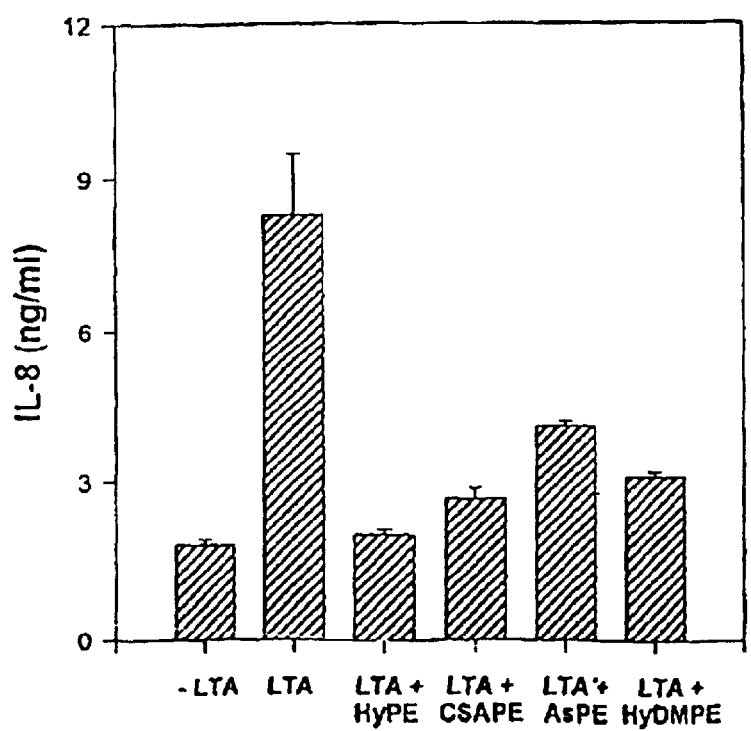
Figure 41B:
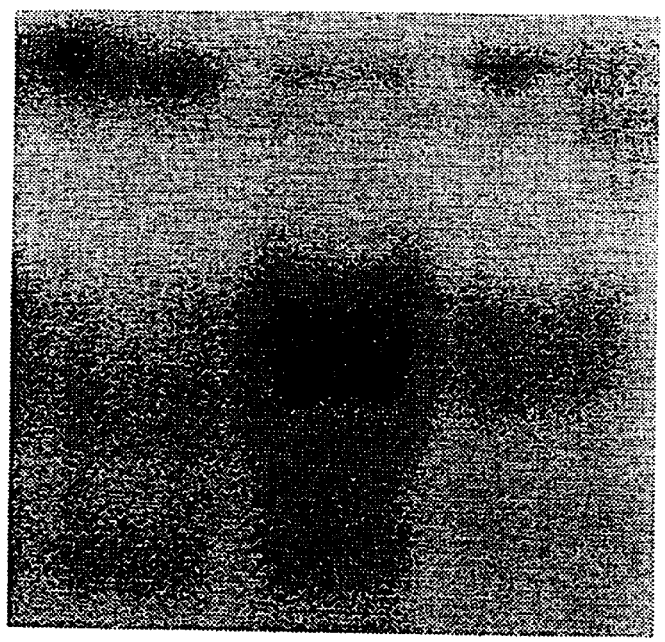

To demonstrate that the PL-conjugates inhibit chemokine elaboration in microvascular endothelial cells from human lung on the level of gene expression (FIG. 41, FIG. 41a and FIG. 41b).

In addition, Experiments 1–8 above demonstrate that PL-conjugates may be used for the treatment of obstructive respiratory disease, alleviating airway narrowing by a plurality of mechanisms, including inhibition of contraction and reduction of airway obstructing infiltrates.

These experiments demonstrate that the PL-conjugates are effective therapy in the treatment of ARDS.

EXAMPLE 13

Transplant Organ Rejection, Alloimmune, and Autoimmune Disease

The PL-conjugates are effective therapy in the treatment of autoimmune and alloimmune disease, including treatment for tissue transplantation. This is demonstrated in experiments 53–58 below. Alloimmune disease includes tissue damage due to the immune response when tissue, including blood products and whole organs, is transplanted from a donor to a recipient. This response is frequently directed against blood vessel tissue. Autoimmune disease may involve any organ via immune mediated destruction directly of the parenchyma or through the organ's vasculature. Two events dominant in either disease process are the proliferation of lymphocytes and immunological responses involving the MHC group of antigens. Commonly accepted demonstrations of the immunosuppressive effect of a drug are the ability to inhibit lymphocyte proliferation and the ability to inhibit the expression of the MHC group of antigens.

Experiments 53–55 demonstrate that the PL-conjugates suppress the expression of the human MHC antigen group, both at the basal level, and upon exposure to a stimulatory agent.

Experiment 53

Human proximal tubular endothelial cells (PTEC) cultured to confluency in human endothelial growth medium were incubated in control or IFNγ supplemented medium (10 ng/ml) in the absence or presence of HYPE (10 μM) for the indicated time. The cells were washed and then mobilized by trypsinization and incubated for 30 min with specific antibodies fluorescently labeled with FITC. The expression of MHC-1, MHC-2, and ICAM was determined by FACS and expressed as the median of the respective cell-associated fluorescence intensity (Table 15).

TABLE 15

Suppression of Major Histocompatibility Antigens and Interferon Stimulation by HYPE in Proximal Tubular Endothelial Cells
Median fluorescence intensity

|  | 24 h | 48 h | 72 h |
|---|---|---|---|
| MHC-1 |  |  |  |
| Medium | 63.21 | 74.99 | 103.66 |
| Medium + HYPE | 31.62 | 40.68 | 48.26 |
| IFN-γ | 268.96 | 375.16 | 399.54 |
| HYPE + IFN-γ | 77.04 | 71.05 | 80.58 |
| MHC-2 |  |  |  |
| Medium |  | 1.41 | 1.67 |
| Medium + HYPE |  | 1.48 | 1.74 |
| IFN-γ |  | 6.10 | 13.82 |
| HYPE + IFN-γ |  | 1.85 | 3.22 |
| ICAM-1 |  |  |  |
| Medium | 45.73 | 46.14 | 50.48 |
| Medium + HYPE | 38.89 | 46.14 | 33.68 |
| IFN-γ | 230.82 | 286.44 | 257.13 |
| HYPE + IFN-γ | 72.34 | 43.32 | 39.24 |

Experiment 54

Figure 42:
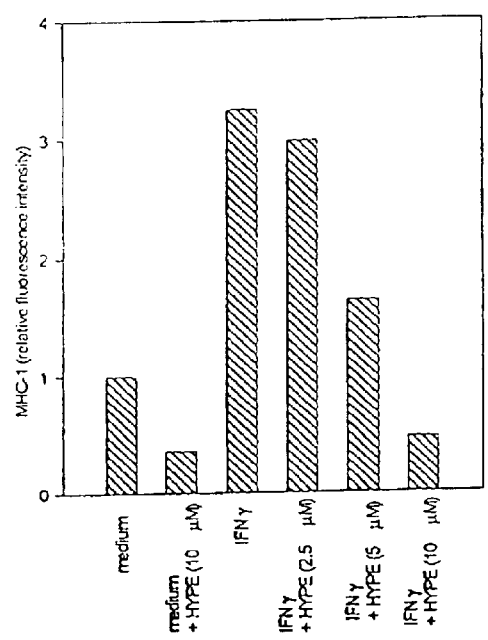
FIG. 42. Suppression of Major Histocompatability Antigens and Interferon Stimulation by HYPE in Proximal Tubular Endothelial Cells—Concentration Dependence FIG. 43. Suppression of Major Histocompatability Antigens and Interferon Stimulation by HYPE in Umbilical Vein Endothelial Cells FIG. 44. Inhibition of Lymphocyte Proliferation by CMPE in Autoimmune Disease FIG. 45. Suppression Leukocyte Adhesion in Ischemia/Reperfusion—Induced Vascular Injury by HYPE and HEPE FIG. 46. Suppression of Leukocyte Extravasation in Ischemia/Reperfusion—Induced Vascular Injury by HYPE and HEPE FIG. 47. Reduction of Retroviral (HIV) Titer by HYPE and HEPE FIG. 48. Reduction of Corneal Opacities by CMPE at the Immediate Post Provocation Phase in Hypersensitivity Conjunctivitis FIG. 49. Reduction of Corneal Opacities by CMPE at the Late Post Provocation Phase in Hypersensitivity Conjunctivitis FIG. 50. Cornea Prostaglandin and Leukotriene $B_4$ Levels in Hypersensitivity Conjunctivitis FIG. 51a. Effect of PL-Conjugates on Injection of HeLa Cels by Chlamydia FIG. 51b. Effect of PL-Conjugates on Injection of HeLa Cels by Chlamydia FIG. 52. Effect of PL-Conjugates on Chlamudia-Induced Apoptosis of HeLa Cells
Figure 42:
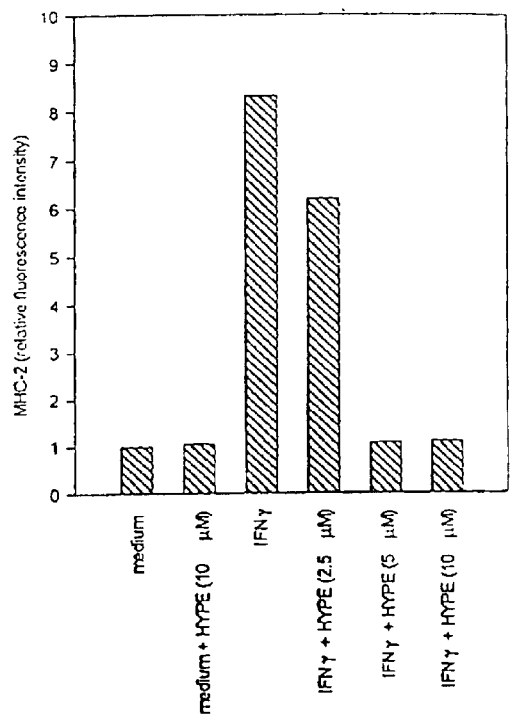

Proximal tubule epithelial cells were incubated for 72 h in culture medium (control) or stimulate with IFNγ (10 ng/ml) in the absence or presence of HYPE at the concentrations indicated in the Fig. The same procedure as in the previous Table was applied. The expression of MHC-1 was determined by FACS and expressed relative to that obtained with the control cells (FIG. 42).

Experiment 55

Figure 43:
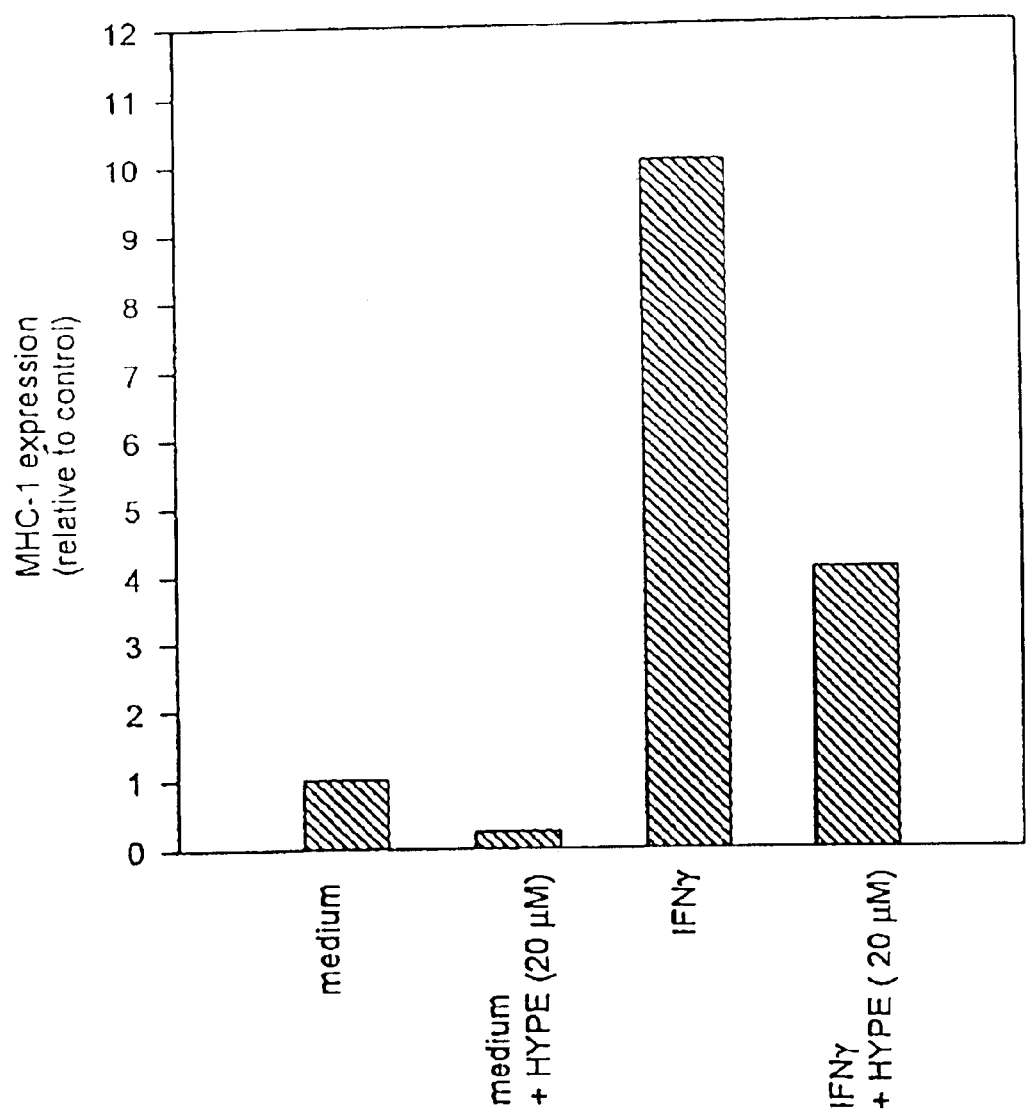

Human umbilical vein endothelial cells were incubated for 72 h in culture medium (control) or stimulated with INFγ, in the absence or presence of HYPE. The same procedure as in the previous Table was applied. The expression of MHC-1 was determined by FACS and expressed as the median of the respective cell-associated fluorescence intensity (FIG. 43).

Experiment 56

Figure 44:
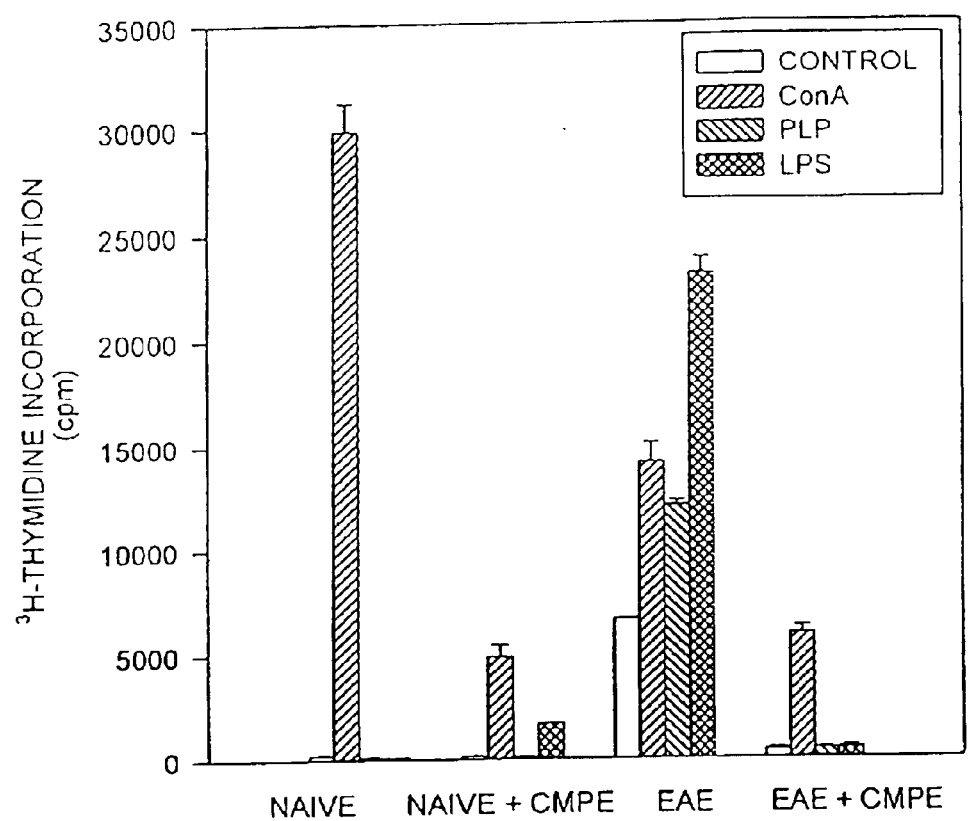

To demonstrate that the PL-conjugates inhibit the ability of lymphocytes from both healthy and diseased animals to proliferate in response to various stimulatory agent. Pooled lymph node cells (LNC) were prepared from three to four mice. The in vitro response of LNC was assayed in triplicate in a 96 well plate. LNC $2.5\times10^5$ were added to each well, together with Concanavalin A (Con A, 1 μg/ml), proteolipoprotein (PLP, 10 μg/ml), and LPS (50 μg/ml) in the presence or absence of CMPE (10 μM) for 96 h. During the final 18 h, 1 μCi/well $^3$[H]thymidine was added to each well, after which the plate was harvested onto a glass fiber filter, and counted by liquid scintillation (FIG. 44).

Experiments 57–58

Figure 45:
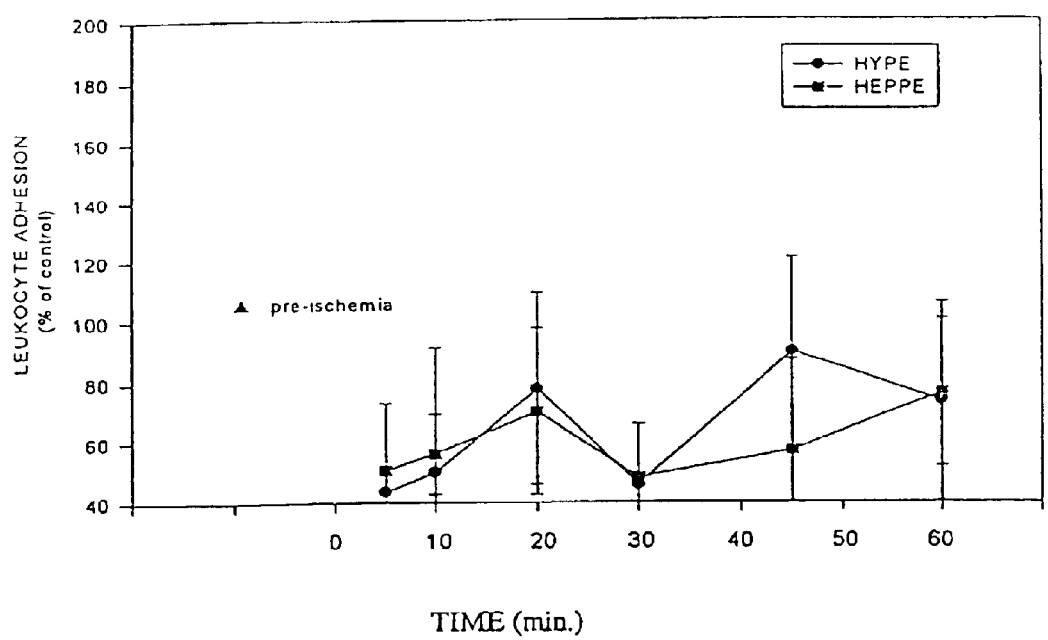
Figure 46:
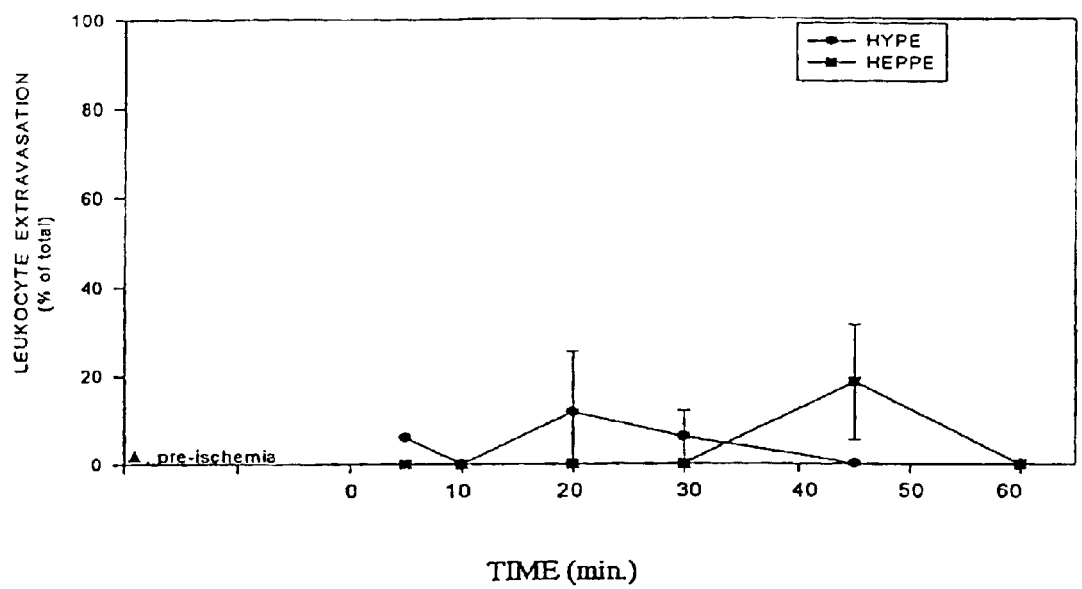

For demonstrating the efficacy of PL-conjugates in experimental protocols for stenosis/reperfusion. Administration of PL-conjugates significantly suppresses the ischemia/reperfusion induced adhesion and extravasation of leukocytes. Leukocytes were labeled in vivo by I.V. injection of rhodamine. Ischemia was applied to exposed cremaster muscle in rats (in situ) for 90 min., then blood flow was restored for reperfusion. The fluorescent-labeled leukocytes adherent to blood vessel walls (FIG. 45) and those extravasated to the extravascular space (FIG. 46) were videotaped and counted at the indicated time point during the reperfusion period. PL-conjugates (10 mg.100 g body weight) were injected I.V. 40 min. and 10 min. prior to induction of ischemia. Each datum in FIG. 32 is mean±SEM obtained from 5 rats with HYPE and 2 rats with HEPPE. $p<0.005$ for all treatments. In FIG. 31, with HYPE-treated rats at 5 min. and at 30 min. $p<0.005$, at 10 min. $p<0.01$, and at 60 min. $p<0.05$; with HEPPE-treated rats $p<0.01$ for all time points.

These experiments demonstrate that the administration of PL-conjugates are effective therapy in the treatment of alloimmune and autoimmune disease, by a plurality of immunosupressive mechanisms.

EXAMPLE 14

Viral Infection

The PL-conjugates are effective in the prophylaxis and treatment of viral infection, particularly the infections due to the human immunodeficiency virus (HIV). This is demonstrated in Experiment 59 below. The process of viral infection comprises stages in which free viral particles are able to enter host cells and produce signs of illness. A commonly accepted assay for anti-viral activity of a drug is to incubate a preparation of the viral agent in the presence of the drug, followed by testing for viral infection in a human cell line.

Experiment 59

Figure 47:
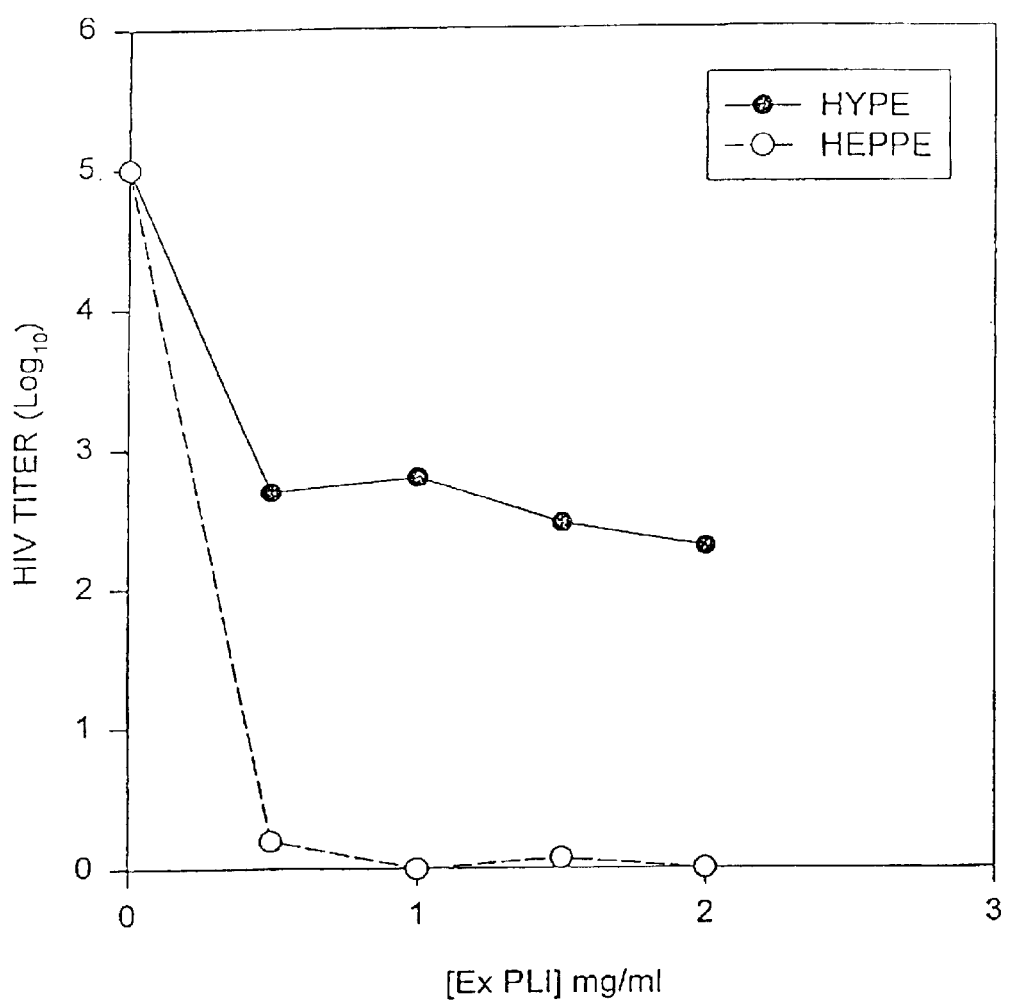

For demonstrating that PL-conjugates significantly inhibit the ability of the HIV agent to infect cells. Blood units were mixed with HIV and the indicated PL-conjugate for 30 min. The cells were then spun and the supernatant was examined for HIV infectivity on HT4–1022 cells as described by Margolis-Nunno et al (Transfusion, 36, 743–750, 1996). 1 mg/ml HEPE=50 μM; 1 mg/ml HYPE=30 μM (FIG. 47).

These experiments demonstrate that administration of PL-conjugates is effective therapy in the treatment of viral infection, particularly HIV, and useful in the eradication of viral particles from contaminated materials, including blood products.

EXAMPLE 15

Conjunctivitis

The PL-conjugates are effective in treatment of hypersensitivity conjunctivitis induced by the delayed-type hypersensitivity immune response. This is demonstrated in Experiment 60 below.

Experiment 60

Figure 48:
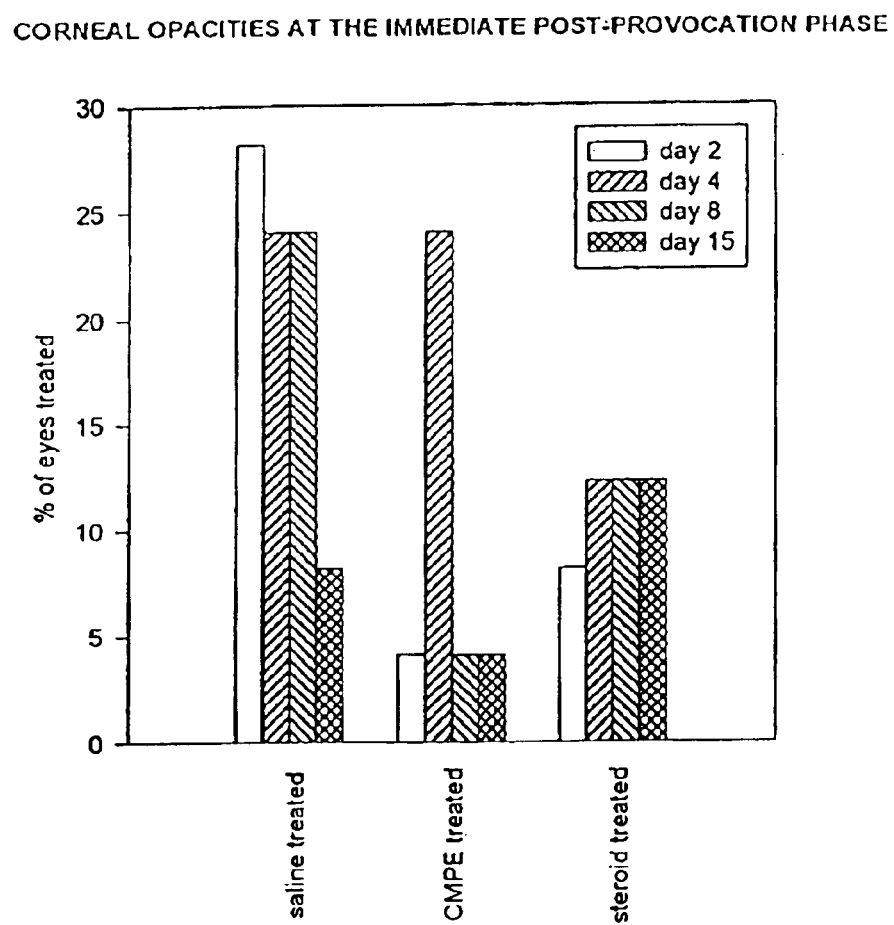
Figure 49:
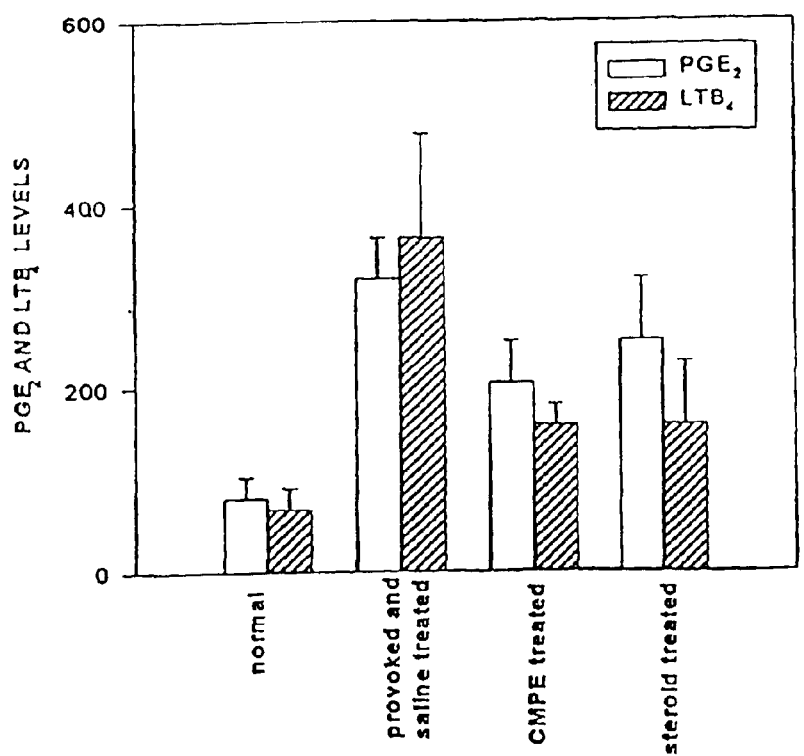
Figure 50:
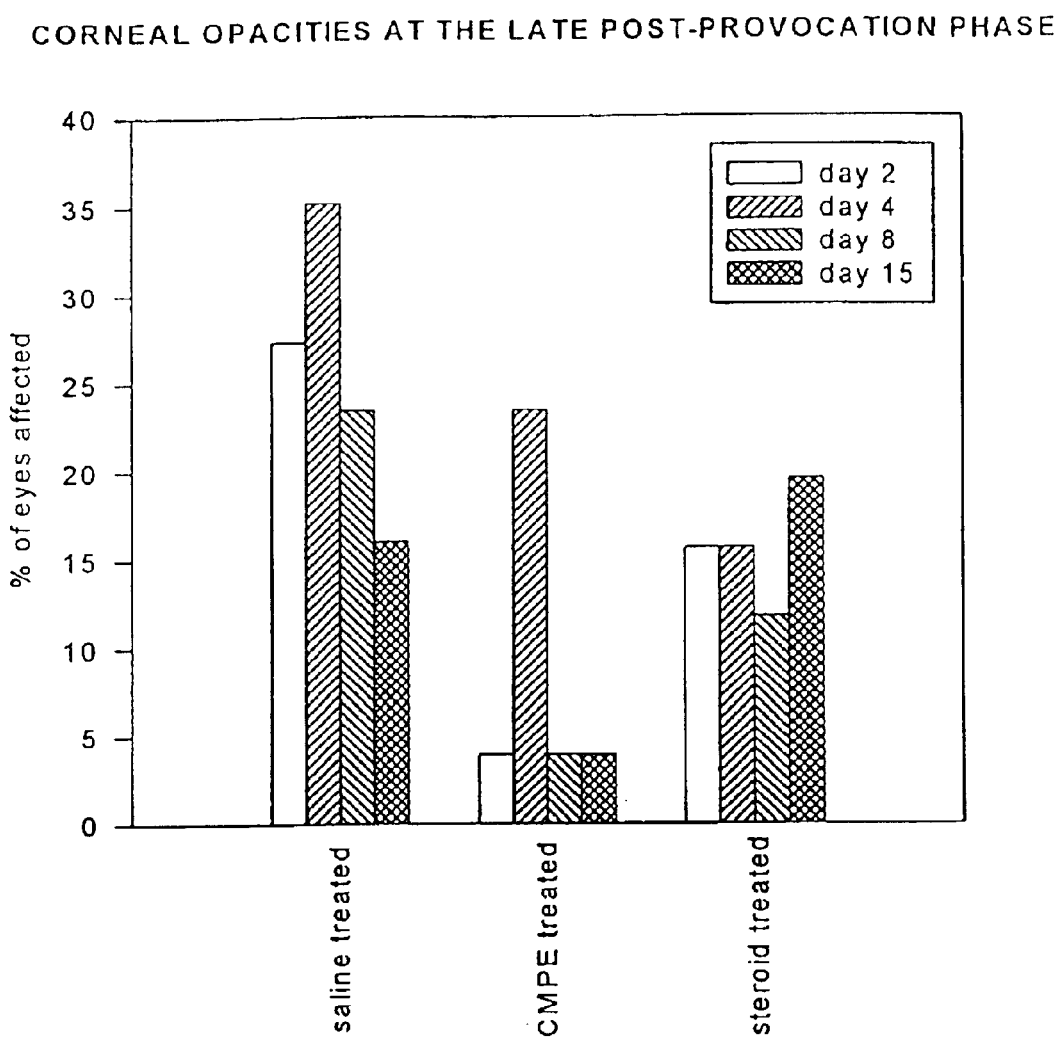

Guinea pigs were sensitized by two I.P. injections (one week between injections) with 10 mg ovalbumin dissolved in 0.5 ml PBS, supplemented with Freunds adjuvant. Three weeks after the original sensitization the first challenge was performed by dripping 5 mg ovalbumin dissolved in 25 ml PBS (FIG. 48) and repeated challenges were performed 3, 4, 5, and 6 days after the first challenge (FIG. 49). For treatment the drug (CMPE), suspended in PBS was dripped into the right eye of each animal on days 3, 4, 5, and 6 after the first challenge. Clinical evaluation of corneal opacity was done on days 5 and 6. Opthalmic levels of LTB4 and $PGE_2$ were determined by ELISA (FIG. 50). For comparison, the effect of steroid treatment was evaluated in parallel.

EXAMPLE 16

Acute Toxicity Tests

Experiment 61

The following compounds were tested: HyPE, CMPE, HeMPE, He SPE and CSAPE in tocixity assays using live mice. The compounds were injected I.P. at one dose of 1000, 500, and 200 mg/kg body weight. Toxicity was evaluated after one week by mortality, body weight, hematocrit, blood count (red and white cells), and visual examination of internal organs after sacrifice. These were compared to control, untreated mice. Each group (treated with each of the above compounds) included six mice.

Except for HePPE, no mortality and no significant change in the above criteria was induced by treateatment with the above compounds. In the group treated with HePPE (heparin-linked PE), 3 mice died within a week due to bleeding.

HyPE was also examined for long-term toxicity: a group of 6 mice recived a dose of 100 mg/kg body weight of HyPE, injected IP every other day (3 injection/week) for 30 weeks (total of 180 mg per 20 g mouse). Toxicity was evaluated as above. No mortaltiy, and no significant change in the above criteria was induced by this treatment.

EXAMPLE 17

Treatment of Chlamydia Infection

The PL-conjugates are effective in the prophylaxis and treatment of infection with intracellular bacterial parasites, particularly infections due to chlamydial species. This is demonstrated in Experiments 62 to 63 below.

Experiment 62

Figure 51:
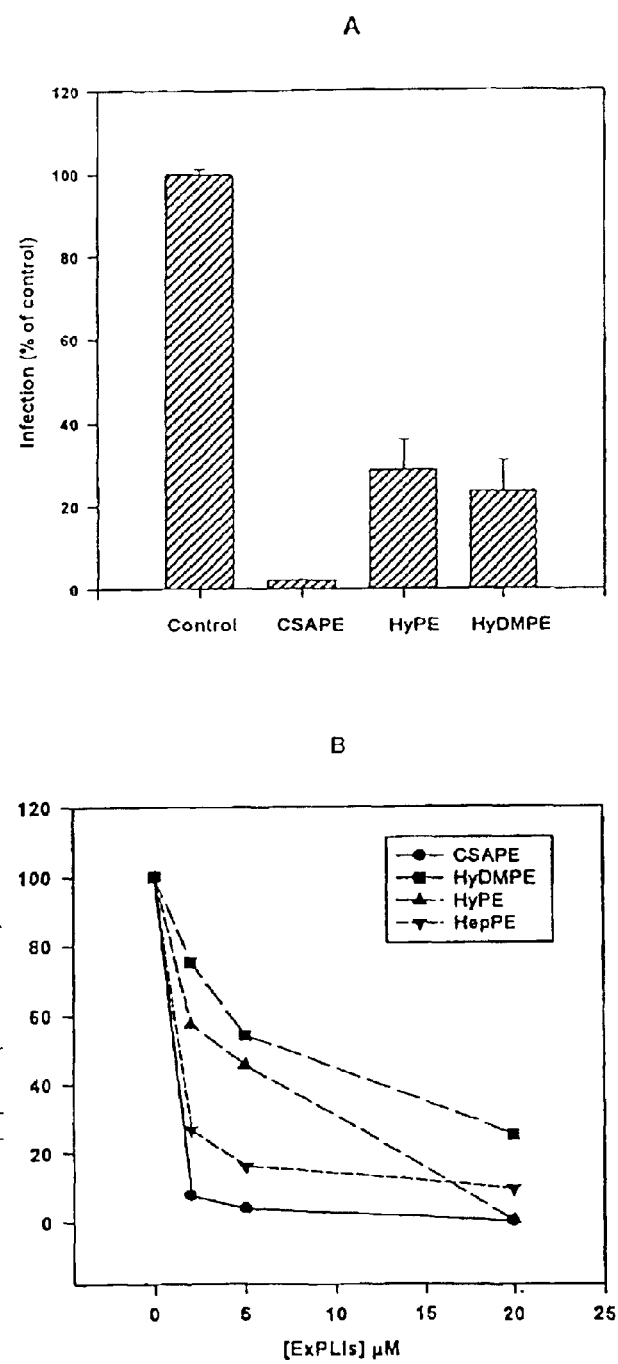

Human cervical adenocarcinoma cell line, HeLa 229 (ATCC, Manassas, Calif.), were cultured and incubated with the PL conjugates (20 micromolar) for 30 min, then incubated with *Chlamydia psittaci* (guinea pig inclusion conjunctivitis servovar) for 24 hr. Infected cells were detected by cytoflouyrometry (FACS) using FITC-conjugated anti-*Chiamydia* antibody (FIG. 51*a*).

Experiment 63

Dose response of the PL-conjugates inhibitory effect on infection of HeLa cells by *Chlamydia* was determined (FIG. 51*b*): HeLa cells were treated with the PL-conjugates at the indicated concentration, and infected with *Chlamydia* as in Experiment 62.

Experiment 64

Figure 52:
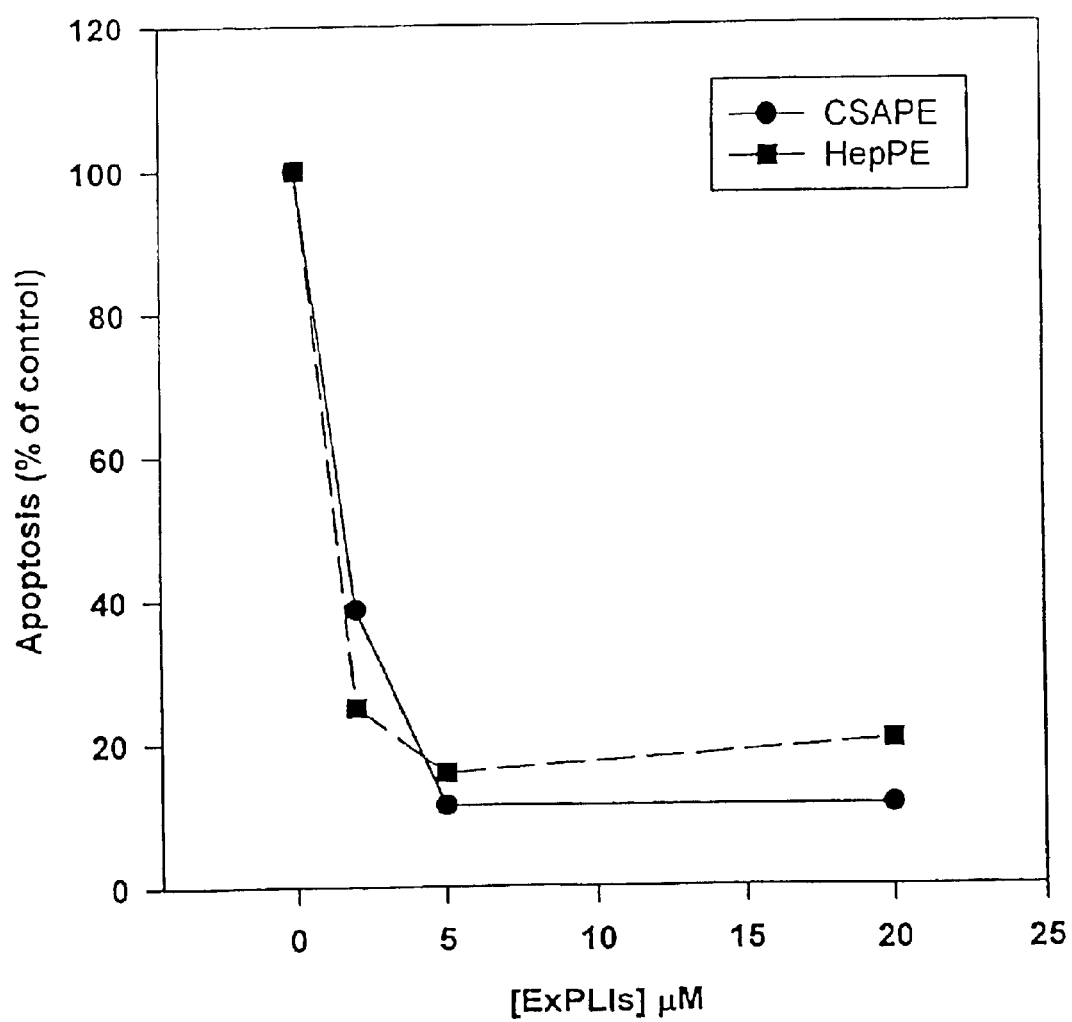

HeLa cells were treated with PL-conjugates and infected with *Chlamydia psittacia* as in Experiment 62. Fpr determination of apoptosis, detergent-permeabilized cells were stained with propidium idodide, and their fluorescence was measured by cytofluorometry (FIG. 52).

Materials and Methods

TNBS-induced Colitis (TNBS) Sigma, St. Louis, Mo.) was rectally administered (25 mg in 1 ml of 50% EtOH) to Hebrew University Sabra rats (200–250 g) after 24 h of food-fasting and the course of the disease was monitored for 2 days, according to our preliminary experiments and previous reports [ ]. In the PL-conjugate treated group, the rats were treated I.P. with 20 mg of CMPE (in 1 ml saline, to obtain about 10 μM in body fluid) at the following time points: 18 h and 0.5 h prior to, as well as 3 h, 18 h and 36 h after TNBS administration. Control, untreated rats received 1 ml of the vehicle (saline) I.P. at the same time points. The rats who survived this process were sacrificed and 10 cm segments of the distal colon were examined for macroscopic histological damage, and dissected longitudinally into two parts. One part was fixed in 10% formalin and used for histological examination, and the other part was subjected to determination of myeloperoxidase (MPO) activity. For indomethacin-induced small intestine injury, indomethacin (Sigma, St Louis, Mo.) a cyclooxygenase inhibitor used for induction of experimental gut injury in animal models (30, 31), was administered I.P. (6 mg in 1 ml of 1% $NaHCO_3$) to rats weighing (200–250 g) and the development and the course of the disease was monitored for 5 days, according to our preliminary experiments and the previous reports [29, 30]. In the CMPE-treated group, the drug (20 mg in 1 ml saline) was given I.P. 1 h prior to and 6 h, 24 h and 48 h after indomethacin administration. Control, untreated rats received 1 ml of the vehicle (saline) at the same time points. The rats who survived this process were sacrificed and examined for macroscopic and histological damage from the duodenum to the cecum. 20 cm of the jejunum were taken for examination of histological damage. Macroscopic scoring of intestinal damage, from 0 (no damage) to 5 (maximal damage) was assessed by a naked-eye examination for areas of mucosal discoloration, erosion, exudation, ulceration, bowel wall thickening and percentage of damaged area. Histological scoring of intestinal damage is the average of microscopic evaluation of five criteria, ranging from 0 (no damage) to 5 (maximal damage): extent of necrotic area, depth of necrosis, white cell infiltration intensity and extent, and fibrosis. Intestinal permeability was evaluated by determining the level of inulin-fluorescein (InF1, Sigma St. Louis, Mo.) in the plasma, following its rectal or oral administration [32]. In a preceding study we have found that while inF1 does not permeate the intestine of normal rats it is readily absorbed in the sick rats; with colitis the intestinal permeability, as measured by InF1 in plasma, reaches its peak at 12 h after administration of TNBS, while in small intestinal injury the peak appears at 72 h after injection of indomethacin [32]. Accordingly, in rats induced with colonic injury, InF1 (4 mg in 0.2 ml saline) was given rectally 12 h after administration of TNBS, and a blood sample (0.5 ml) was taken 2 h later from the tail vein of the ether-anaesthetized rats [32]. In rats with small intestinal injury the same amount of InF1 was given orally 72 h after administration of indomethacin, and blood samples were taken 3 h later [32]. For determination of blood level of InF1, the plasma was separated by centrifugation and the fluorescence intensity was determined at 488 nm (excitation) and 517 nm (emission), as previously described [32]. Myeloperoxidase activity in tissue homogenate was determined spectroscopically by o-dianisidine/$H_2O_2$ reaction [19, 33]. Due to the high mortality rate among the control rats, the determinations of MPO, intestinal permeability and historical damage was limited to the rats who survived the experiment's course. This introduced a methodological problem, since it is likely that the rats which died had the most sever damage, but these could not be included in the comparison between treated and untreated animals. This drawback was taken into consideration when analyzing the data of MPO activity and InF1 permeation, as described in Results. Statistical analysis: The results are expressed as mean±SEM, and difference between the various treatment was examined for significance by the Student t-test.

Colitis Induced in Mice by Dextran-sulfate

Three groups of mice (n=12) were included. Colitis was induced by 4% dextran sulfate sodium salt (DSS) (ICN, MW 36,000–44,000) in the drinking water. Hyaluronic acid-linked phosphatidylethanolamine (HyPE), 80 µg/g body weight, was given orally (by gastric intubation). In Group 1 (DSS), feeding (free drinking) with 4% dextran sulfate sodium (DSS) dissolved in tap water for 7 days followed by plain water for 7 days and treatment was with oral administration of solvent (PBS). In Group 2 (DSS+HyPE), feeding was with 4% dextran sulfate sodium (DSS) dissolved in tap water for 7 days followed by plain water for 7 days and treatment was with oral administration HyPE (2×80 µg/g; orally from a stock solution of 8 mg/ml in PBS, pH=8). Group 3 (healthy control) received plain water for 14 days. Drinking water was ad libitum. The body weight was determined daily (control body weight on the first day of the experiment before treatment is started; final body weight on the day of sacrifice. Dextran treatment was continued until the mean decrease in body weight of the dextran/solvent containing dextran was changed once after three days; water and water+dextran consumption was determined after 3 the end of the dextran supplementation period. Hemoccult (hemo FEC®, Boehringer Mannheim), presence of gross blood (blood clot around the anus (and on day 6 if not positive on previous day) and on day 10.

| Criteria for scoring Disease Activity Index* | | | |
|---|---|---|---|
| Score | Weight Loss (%) | Stool consistency | Occult blood or gross bleeding |
| 0 | None | Normal | Negative |
| 1 | 1–5 | Loose stool | Negative |
| 2 | 5–10 | Loose stool | Hemoccult positive |
| 3 | 10–15 | Diarrhea | Hemoccult positive |
| 4 | >15 | Diarrhea | Gross bleeding |

*Disease Activity Index = (combined score of weight loss, stool consistency and bleeding)/3
Normal stools = well formed pellets; loose stools = pasty stool that does not stick to anus; diarrhea = liquid stools that stick to the anus (Murray et al., 1993).

For hematology and macroscopy, the animals were anaesthetized with pentobarbital (90 mg/kg) whereafter the abdomen was opened. 0.5 ml of blood was taken from the abdominal aorta and collected in Microtainer® tubes with $K_2$ EDTA for hematological determination. For determination of colon length, the colon was excised from colo-caecal junction to anus, flushed with saline, placed on a non-absorbent surface and the colon length measured with a ruler. For histology, the distal colon is placed in neutral buffered formaldehyde for at least 3 days. Each segment is cut into 4 transverse parts and routinely processed before embedding in paraffin. The Crypt scoring method (Murray et al., 1993) was as follows: grade: 0=intact crypt, 1=loss of bottom ⅓ of crypts, 2=loss of bottom ⅔, 3=loss of entire crypt but surface epithelium remains, 4=complete erosion of mucous. % area involvement: 1=1–25%, 2=25–50%, 3=51–75%, 4=76–100%. The grade value score is multiplied by the % involvement score (maximum score=16). The injury scoring method (WBC in tissue, Muray et al., 1993) was as follows: grade: 0=none, 1=minor, 2=moderate, 3=extensive. % area involvement: 1=1–25%, 2=25–50%, 3=51–75%, 4=76–100%. The injury score is multiplied by the % involvement score for each of the four sections (maximum score=12). Number of lymph 'nodes'32 number of accumulations of lymph cells (per section), including normal lymph nodes: every group of lymphoid cells containing more than 20 cells grouped together, were considered as one single accumulation. Okayasu et al., Gastoenterology, 98, 694 (1990). Murthy et al. Dig Dis Sci, 38, 1722 (1993).

EAE-scoring of disease severity was performed through daily observation of the experimental animals based upon the following scale:

| Clinical signs | Grade |
|---|---|
| None | 0 |
| Tail weakness | 1 |
| Hind limb weakness and impaired rolling | 2 |
| Hind limb paraplegia | 3 |
| Hind limb paraplegia and fore limb weakness | 4 |
| Quadriplegia and incontinence | 5 |
| Death | 6 |

Delayed-type Hypersensitivity Reaction

Female balb/c mice, 8–12 weeks old, were sensitized by topical application of 50 µL 2% oxazolone in DMSO:saline/ 1:18 to the shaved stomach on Day 0, and challenged six days later (day 6) by topical application of the oxalozone solution to both ears on both sides (5 µL per side). The PL-conjugate to be tested was administered by the modes outlined below at the dose indicated it the corresponding Table, from day 0 until day 6. The hypersensitivity response was evaluated 24 hours after the challenge with the antigen by measuring the swelling of the ears (using a micrometer) and comparing the results to the measurements taken in the same mouse before treatment.

Release of Arachidonic and Oleic Acid from Macrophages

For macrophages, murine P388$D_1$ cells were pre-labeled with [$^3$H]oleic acid and treated for 30 min with the PL-conjugate, the incubated for 20 h in either the presence (●) or absence (○) of LPS for 20 h (FIG. 19). Iscove's modified Dulbecco's medium (endotoxin <0.05 ng/ml) was from Whittaker Bioproducts (Walkersville, Md.). Fetal bovine serum was from Hyclone Labs. (Logan, Utah). Non-essential amino acids were from Irvine Scientific (Santa Ana, Calif.). [9,10-$^3$H]Oleic acid (specific activity 55 Ci/mmol) was from New England Nuclear (Boston, Mass.). LPS (*E. coli* 0111:B4) was from Sigma (ST. Louis, Mo.). P388D1 cells (MAB) clone (5, 6) were maintained at 37° C. in a humidified atmosphere at 90% air and 10% $CO_2$ in iscove's modified Dulbecco's medium supplemented with 10% fetal bovine serum, 2mM glutamine, 100 units/ml penicillin, 100 µg/ml streptomycin and non-essential amino acids. P388D$_1$ cells were plated at 10$^6$ per well, allowed to adhere overnight, and used for experiments the following day. All experiments were conducted in serum-free Iscove's modified Dulbecco's medium. Radiolabeling of the P388D$_1$ cells with [$^3$H]OA was achieved by including 5 µCi/ml [3H] OA during the overnight adherence period (20 h). Labeled OA that had not been incorporated into cellular lipids was removed by washing the cells six times with serum-free medium containing 1 mg/ml albumin. For measurement of extracellular [$^3$H]oleic acid release the cells were placed in serum-free medium for 30 min before the addition of LPS or exogenous PL-conjugate for different periods of time in the presence of 0.5 mg/ml bovine serum albumin. The supernatants were removed, cleared of detached cells by centrifugation, and assayed for radioactivity by liquid scintillation counting. LPS-stimulated OA release is expressed by subtracting the basal rate observed in the absence of agonist and inhibitor. These background values were in the range of 1000–2000 cpm. Each set of experiments was repeated at least three times with similar results. Unless otherwise indicated, the data presented are from representative experiments.

Tumor Cell Invasion Assay

For the chemoattractant invasion assay polyvinylpyrrolidone-free polycarbonate fibers, 8 µM pore size, were coated with 25 µg of a mixture of basement membrane components (Matrigel) and placed in modified Boyden chambers. The cells (2×10$^5$) were released from their culture dishes by a short exposure to EDTA (1 mM), centrifuged, re-suspended in 0.1% BSA/DMEM, and placed in the upper compartment of the Boyden chamber. Fibroblast conditioned medium was placed in the lower compartment as a source of chemoattractants. After incubation for 6 h at 37 C, the cells on the lower surface of the filter were stained with Diff-Quick (American Scientific Products) and were quantitated with an image analyzer (Optomax V) attached to an Olympus CK2 microscope. The data are expressed relative to the area occupied by untreated cells on the lower surface of the filter. (Albini et al., A Rapid In Vitro Assay for Quantitating the Invasive Potential of Tumor Cells. Cancer Res. 47:3239–3245, 1987).

What we claim is:

1. A phosphatidylethanolamine conjugate according to the formula

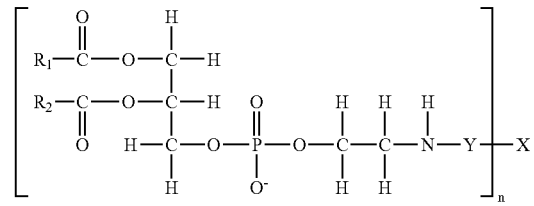

wherein
R$_1$ is a linear, saturated, mono-unsaturated, or poly-unsaturated, alkyl chain ranging in length from 2 to 30 carbon atoms;
R$_2$ is a linear, saturated, mono-unsaturated, or poly-unsaturated, alkyl chain ranging in length from 2 to 30 carbon atoms;
Y is either nothing or a spacer group ranging in length from 2 to 30 atoms, wherein said spacer comprises —CO-alkylene-NH—, —CO-alkylene-CO— or a combination thereof; and
X is either a physiologically acceptable monomer, dimer, or oligomer, wherein n is unity, or a physiologically acceptable polymer, wherein n is a number from 1 to 1,000, wherein x is a glycosaminoglycan;
wherein if Y is nothing the phosphatidylethanolamine is directly linked to X via a carboxylic group.

2. The compound according to claim 1 wherein the glycosaminoglycan is hyaluronic acid, heparin, heparan sulfate, chondrotin sulfate, keratin, keratan sulfate, dermatan sulfate or a derivative thereof.

3. The compound according to claim 1 wherein the glycosamininoglycan is di- and trisaccharide unit monomers of glycosaminoglycans.

4. The compound according to claim 3, wherein the chondrotin sulfate is chondrotin-6-sulfate, chondroitin-4-sulfate or a derivative thereof.

5. The compound according to claim 1, wherein the glycosaminoglycan is hyaluronic acid.

* * * * *